(12) United States Patent
Donovan et al.

(10) Patent No.: US 11,242,325 B2
(45) Date of Patent: Feb. 8, 2022

(54) PEGYLATED PRODRUGS OF PHENOLIC TRPV1 AGONISTS

(71) Applicant: CONCENTRIC ANALGESICS, INC., San Francisco, CA (US)

(72) Inventors: John F. Donovan, San Francisco, CA (US); Craig Husfeld, San Francisco, CA (US)

(73) Assignee: CONCENTRIC ANALGESICS, INC., San Francisco, CA (US)

( * ) Notice: Subject to any disclaimer, the term of this patent is extended or adjusted under 35 U.S.C. 154(b) by 26 days.

(21) Appl. No.: 16/895,735

(22) Filed: Jun. 8, 2020

(65) Prior Publication Data
US 2020/0299245 A1 Sep. 24, 2020

Related U.S. Application Data

(62) Division of application No. 16/522,564, filed on Jul. 25, 2019, now Pat. No. 10,717,712.

(60) Provisional application No. 62/711,361, filed on Jul. 27, 2018.

(51) Int. Cl.
*C07D 241/04* (2006.01)

(52) U.S. Cl.
CPC .................. *C07D 241/04* (2013.01)

(58) Field of Classification Search
CPC ..................................................... C07D 241/04
See application file for complete search history.

(56) References Cited

U.S. PATENT DOCUMENTS

| | | | |
|---|---|---|---|
| 3,598,122 A | 8/1971 | Zaffaroni et al. | |
| 3,598,123 A | 8/1971 | Zaffaroni | |
| 3,710,795 A | 1/1973 | Higuchi et al. | |
| 3,731,683 A | 5/1973 | Zaffaroni et al. | |
| 3,742,951 A | 7/1973 | Zaffaroni et al. | |
| 3,814,097 A | 6/1974 | Ganderton et al. | |
| 3,921,636 A | 11/1975 | Zaffaroni | |
| 3,972,995 A | 8/1976 | Tsuk et al. | |
| 3,993,072 A | 11/1976 | Zaffaroni | |
| 3,993,073 A | 11/1976 | Zaffaroni | |
| 3,996,934 A | 12/1976 | Zaffaroni | |
| 4,031,894 A | 6/1977 | Urquhart et al. | |
| 4,060,084 A | 11/1977 | Chandrasekaran et al. | |
| 4,069,307 A | 1/1978 | Higuchi et al. | |
| 4,077,407 A | 3/1978 | Theeuwes et al. | |
| 4,151,273 A | 4/1979 | Chiou et al. | |
| 4,201,211 A | 5/1980 | Chandrasekaran et al. | |
| 4,229,447 A | 10/1980 | Porter | |
| 4,230,105 A | 10/1980 | Harwood | |
| 4,292,299 A | 9/1981 | Suzuki et al. | |
| 4,292,303 A | 9/1981 | Keith et al. | |
| 4,327,725 A | 5/1982 | Cortese et al. | |
| 4,343,789 A | 8/1982 | Kawata et al. | |
| 4,476,116 A | 10/1984 | Anik | |
| 4,596,795 A | 6/1986 | Pitha | |
| 4,624,848 A | 11/1986 | Lee | |
| 4,755,386 A | 7/1988 | Hsiao et al. | |
| 4,812,590 A | 3/1989 | Saari | |
| 4,871,549 A | 10/1989 | Ueda et al. | |
| 4,935,368 A | 6/1990 | Kotani et al. | |
| 4,968,509 A | 11/1990 | Radebaugh et al. | |
| 5,011,692 A | 4/1991 | Fujioka et al. | |
| 5,017,381 A | 5/1991 | Maruyama et al. | |
| 5,094,782 A | 3/1992 | Chen et al. | |
| 5,116,817 A | 5/1992 | Anik | |
| 5,229,135 A | 7/1993 | Philippon et al. | |
| 5,260,068 A | 11/1993 | Chen | |
| 5,260,069 A | 11/1993 | Chen | |
| 5,281,420 A | 1/1994 | Kelm et al. | |
| 5,336,168 A | 8/1994 | Sibalis | |
| 5,340,591 A | 8/1994 | Nakano et al. | |
| 5,456,923 A | 10/1995 | Nakamichi et al. | |
| 5,461,140 A | 10/1995 | Heller et al. | |
| 5,508,040 A | 4/1996 | Chen | |
| 5,516,527 A | 5/1996 | Curatolo | |
| 5,567,441 A | 10/1996 | Chen | |
| 5,622,721 A | 4/1997 | Dansereau et al. | |
| 5,665,378 A | 9/1997 | Davis et al. | |
| 5,686,105 A | 11/1997 | Kelm et al. | |
| 5,700,410 A | 12/1997 | Nakamichi et al. | |
| 5,700,485 A | 12/1997 | Berde et al. | |
| 5,723,269 A | 3/1998 | Akagi et al. | |
| 5,739,136 A | 4/1998 | Ellinwood, Jr. et al. | |
| 5,837,280 A | 11/1998 | Kenealy et al. | |

(Continued)

FOREIGN PATENT DOCUMENTS

| EP | 1201649 A1 | 5/2002 |
|---|---|---|
| EP | 2774915 A1 | 9/2014 |

(Continued)

OTHER PUBLICATIONS

Hunt, et al., Disubstituted Pyrimidines as Lck Inhibitors, Bioorganic & Med. Chem. Letters, 19, 5440-5443, (2009). (Year: 2009).*
Apfelbaum et al. Postoperative Pain Experience: Results from a National Survey Suggest Postoperative Pain Continues to Be Undermanaged. Anesth Analg 97:534-540 (2003).
Bley. Recent developments in transient receptor potential vanilloid receptor 1 agonist-based therapies. Expert Opin Investig Drugs. 13(11):1445-1456 (2004).
Caterina et al. The vanilloid receptor: a molecular gateway to the pain pathway. Annu Rev Neurosci. 24:487-517 (2001).
Chou et al. Management of Postoperative Pain: A Clinical Practice Guideline From the American Pain Society, the American Society of Regional Anesthesia and Pain Medicine, and the American Society of Anesthesiologists' Committee on Regional Anesthesia, Executive Committee, and Administrative Council. J Pain 17(2):131-157 (2016).

(Continued)

*Primary Examiner* — Erich A Leeser
(74) *Attorney, Agent, or Firm* — Wilson Sonsini Goodrich & Rosati

(57) ABSTRACT

Described herein are compounds, pharmaceutical compositions and medicaments that include such compounds, and methods of using such compounds to modulate transient receptor potential vanilloid 1 receptor (TRPV1) activity.

18 Claims, 3 Drawing Sheets

(56) References Cited

U.S. PATENT DOCUMENTS

| | | | |
|---|---|---|---|
| 5,837,284 | A | 11/1998 | Mehta et al. |
| 5,840,329 | A | 11/1998 | Bai |
| 5,858,401 | A | 1/1999 | Bhalani et al. |
| 5,869,090 | A | 2/1999 | Rosenbaum |
| 5,962,532 | A | 10/1999 | Campbell et al. |
| 5,977,175 | A | 11/1999 | Lin |
| 6,083,518 | A | 7/2000 | Lindahl |
| 6,391,452 | B1 | 5/2002 | Antonsen et al. |
| 6,465,014 | B1 | 10/2002 | Moroni et al. |
| 6,667,048 | B1 | 12/2003 | Lambert et al. |
| 6,923,983 | B2 | 8/2005 | Morgan et al. |
| 6,929,801 | B2 | 8/2005 | Klose et al. |
| 6,932,983 | B1 | 8/2005 | Straub et al. |
| 6,946,144 | B1 | 9/2005 | Jordan |
| 6,960,563 | B2 | 11/2005 | Egbaria et al. |
| 7,632,519 | B2 | 12/2009 | Jamieson et al. |
| 7,632,539 | B2 | 12/2009 | Miyake |
| 7,943,666 | B2 | 5/2011 | Singh et al. |
| 8,217,005 | B2 | 7/2012 | Jenkins et al. |
| 8,367,733 | B2 | 2/2013 | Burch et al. |
| 8,420,600 | B2 | 4/2013 | Burch et al. |
| 8,497,237 | B2 | 7/2013 | Jenkins et al. |
| 8,569,228 | B2 | 10/2013 | Jenkins et al. |
| 8,685,916 | B2 | 4/2014 | Jenkins et al. |
| 8,802,681 | B2 | 8/2014 | Jenkins et al. |
| 9,040,032 | B2 | 5/2015 | Jenkins et al. |
| 9,139,612 | B2 | 9/2015 | Jenkins et al. |
| 9,238,020 | B2 | 1/2016 | Jenkins et al. |
| 9,359,316 | B1 | 6/2016 | Husfeld et al. |
| 10,717,712 | B2 | 7/2020 | Donovan et al. |
| 2004/0013734 | A1 | 1/2004 | Babcock et al. |
| 2004/0156931 | A1 | 8/2004 | Burch et al. |
| 2006/0240097 | A1 | 10/2006 | Jamieson et al. |
| 2008/0020996 | A1 | 1/2008 | Singh et al. |
| 2008/0193481 | A1 | 8/2008 | Bundle et al. |
| 2010/0152434 | A1 | 6/2010 | Peterson |
| 2010/0227921 | A1 | 9/2010 | Franklin et al. |
| 2011/0243884 | A1 | 10/2011 | O'Shea et al. |
| 2011/0262359 | A1 | 10/2011 | Jenkins et al. |
| 2011/0262360 | A1 | 10/2011 | Jenkins et al. |
| 2012/0232066 | A1 | 9/2012 | Jenkins et al. |
| 2012/0270847 | A1 | 10/2012 | Franklin et al. |
| 2013/0035635 | A1 | 2/2013 | Rau et al. |
| 2013/0079364 | A1 | 3/2013 | Jenkins et al. |
| 2013/0089504 | A1 | 4/2013 | Jenkins et al. |
| 2015/0119423 | A1 | 4/2015 | Kandula et al. |
| 2016/0136153 | A1 | 5/2016 | Jenkins |
| 2017/0100390 | A1 | 4/2017 | Jenkins |
| 2017/0159100 | A1 | 6/2017 | Hasserodt et al. |
| 2017/0260131 | A1 | 9/2017 | Husfeld et al. |
| 2019/0055272 | A1 | 2/2019 | Husfeld et al. |
| 2019/0216787 | A1 | 7/2019 | Donovan et al. |
| 2019/0284132 | A1 | 9/2019 | Husfeld et al. |

FOREIGN PATENT DOCUMENTS

| | | |
|---|---|---|
| KR | 101478520 B1 | 1/2015 |
| WO | WO-2006116485 A2 | 11/2006 |
| WO | WO-2011133149 A1 | 10/2011 |
| WO | WO-2011133150 A1 | 10/2011 |
| WO | WO-2012098557 A1 | 7/2012 |
| WO | WO-2013175376 A2 | 11/2013 |
| WO | WO-2016086063 A1 | 6/2016 |
| WO | WO-2017147146 A1 | 8/2017 |
| WO | WO-2017205534 A1 | 11/2017 |
| WO | WO-2020023793 A1 | 1/2020 |
| WO | WO-2020023794 A1 | 1/2020 |

OTHER PUBLICATIONS

Gan et al. Incidence, patient satisfaction, and perceptions of postsurgical pain: results from a US national survey. Curr Med Res Opin 30(1):149-160 (2014).
Gao et al. Uses of Chromatography in Fine Chemical Industry. China Petrochemical Press. (p. 443) (Nov. 30, 1997).
Gomes et al. Cyclization-activated Prodrugs. Molecules 12:2484-2506 (2007).
Huang et al. Capsaicin and its analogues: structure-activity relationship study. Cur Med Chem 20:2661-2672 (2013).
Hunt et al. Disubstituted pyrimidines as Lck inhibitors. Bioorg Med Chem Lett. 19(18):5440-3 (2009).
Kehlet et al. Persistent postsurgical pain: risk factors and prevention. Lancet 367(9522):1618-1625 (2006).
Kirkpatrick et al. In vitro and in vivo assessment of the abuse potential of PF614, a novel BIO-MD™ prodrug of oxycodone. J Opiod Manag 13(1):39-49 (2017).
Li et al. Transient Receptor Potential Ion Channels: Physiological Functions and Diseases. Hubei Science & Technology Press (pp. 129-130) (Nov. 30, 2007).
Liberman et al. Pharmaceutical Dosage Forms. 2nd Ed. 1:209-214 (1990).
Lu et al. Basic and Clinical Aspects of Visceral Pain. People's Military Medical Press (p. 306) (Aug. 31, 2013).
Mei et al. Handbook of Chinese Licensed Pharmacists. Hubei Science & Technology Press (pp. 530-531) (Jan. 31, 2002).
Milewski et al. In vitro permeation of a pegylated naltrexone prodrug across microneedle-treated skin. J Control Release 146(1):37-44 (2010).
PCT/US2015/62531 International Search Report and Written Opinion dated Jan. 27, 2016.
PCT/US2017/034318 International Search Report and Written Opinion dated Aug. 23, 2017.
PCT/US2019/043517 International Search Report and Written Opinion dated Oct. 9, 2019.
PCT/US2019/043518 International Search Report and Written Opinion dated Oct. 24, 2019.
Pogatzki-Zahn et al. Room for improvement: unmet needs in postoperative pain management. Expert Rev. Neurother. 12(5):587-600 (2012).
Saari et al. Cyclization-activated prodrugs. Basic carbamates of 4-hydroxyanisole. J Med Chem 33(1):97-101 (1990).
Singh et al. Encyclopedia of Pharmaceutical Technology. 2nd Ed. pp. 754-757 (2002).
Stella et al. Prodrug strategies to overcome poor water solubility. Advanced Drug Delivery Reviews 59:677-694 (2007).
Swanson et al. Identification and biological evaluation of 4-(3-trifluoromethylpyridin-2-yl)piperazine-1-carboxylic acid (5-trifluoromethylpyridin-2-yl)amide, a high affinity TRPV1 (VR1) vanilloid receptor antagonist. J Med Chem 48(6):1857-1872 (2005).
U.S. Appl. No. 14/743,375 Office Action dated Jan. 22, 2016.
U.S. Appl. No. 15/529,076 Office Action dated Apr. 3, 2018.
U.S. Appl. No. 15/529,076 Office Action dated Jul. 11, 2019.
U.S. Appl. No. 15/529,076 Office Action dated Mar. 13, 2020.
U.S. Appl. No. 15/529,076 Office Action dated Oct. 29, 2018.
U.S. Appl. No. 16/303,082 Office Action dated Feb. 18, 2020.
U.S. Appl. No. 90/000,238 Supplemental Examination Certificate dated Nov. 15, 2017.
U.S. Appl. No. 96/000,238 Reasons For No Substantial New Question of Patentability dated Nov. 15, 2017.
Zawilska et al. Prodrugs: A challenge for the drug development. Pharmacological Reports 65:1-14 (2013).

* cited by examiner

PEGYLATED PRODRUGS OF PHENOLIC TRPV1 AGONISTS

CROSS-REFERENCE

This application is a Divisional application of U.S. application Ser. No. 16/522,564, filed Jul. 25, 2019, which claims the benefit of U.S. Provisional Application Ser. No. 62/711,361 filed Jul. 27, 2018, which are hereby incorporated by reference in their entirety.

BACKGROUND OF THE INVENTION

Described herein are compounds, pharmaceutical compositions and medicaments that include such compounds, and methods of using such compounds to modulate the transient receptor potential vanilloid 1 receptor (TRPV1) activity.

SUMMARY OF THE INVENTION

In one aspect, described herein is a compound having the structure of Formula (I):

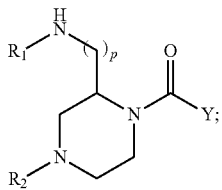

Formula (I)

wherein:

Y is a phenolic TRPV1 agonist, wherein the hydrogen atom of the phenolic hydroxyl group is replaced by a covalent bond to

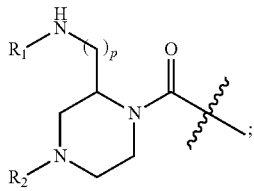

$R_1$ is hydrogen or $C_1$-$C_6$alkyl;
$R_2$ is —$(CH_2CH_2O)_nR_3$, —$C(O)(CH_2)_mO(CH_2CH_2O)_nR_3$, —$C(O)O(CH_2CH_2O)_nR_3$, —$C(O)N(R_4)(CH_2CH_2O)_nR_3$, —$C(O)R_5$, —$C(O)OR_5$, or —$C(O)N(R_4)(R_5)$;
$R_3$ is hydrogen or $C_1$-$C_6$alkyl;
$R_4$ is hydrogen or $C_1$-$C_6$alkyl;
$R_5$ is $C_1$-$C_{50}$alkyl;
m is 1-10;
n is 1-50; and
p is 1-9;
or a pharmaceutically acceptable salt, pharmaceutically acceptable solvate, or hydrate thereof.

In some embodiments is a compound of Formula (I), wherein $R_2$ is —$(CH_2CH_2O)_nR_3$, —$C(O)(CH_2)_mO(CH_2CH_2O)_nR_3$, —$C(O)O(CH_2CH_2O)_nR_3$, or —$C(O)N(R_4)(CH_2CH_2O)_nR_3$. In some embodiments is a compound of Formula (I), wherein $R_2$ is —$C(O)(CH_2)_mO(CH_2CH_2O)_nR_3$. In some embodiments is a compound of Formula (I), wherein m is 1-5. In some embodiments is a compound of Formula (I), wherein m is 2. In some embodiments is a compound of Formula (I), wherein $R_2$ is —$(CH_2CH_2O)_nR_3$. In some embodiments is a compound of Formula (I), wherein $R_2$ —$C(O)O(CH_2CH_2O)_nR_3$. In some embodiments is a compound of Formula (I), wherein $R_2$ is —$C(O)N(R_4)(CH_2CH_2O)_nR_3$. In some embodiments is a compound of Formula (I), wherein $R_4$ is hydrogen. In some embodiments is a compound of Formula (I), wherein $R_4$ is $C_1$-$C_6$alkyl. In some embodiments is a compound of Formula (I), wherein $R_3$ is hydrogen. In some embodiments is a compound of Formula (I), wherein $R_3$ is $C_1$-$C_6$alkyl. In some embodiments is a compound of Formula (I), wherein $R_3$ is —$CH_3$. In some embodiments is a compound of Formula (I), wherein n is 1-30. In some embodiments is a compound of Formula (I), wherein n is 2-20. In some embodiments is a compound of Formula (I), wherein n is 2-12. In some embodiments is a compound of Formula (I), wherein n is 4-10. In some embodiments is a compound of Formula (I), wherein $R_2$ is —$C(O)R_5$. In some embodiments is a compound of Formula (I), wherein $R_2$ is —$C(O)OR_5$. In some embodiments is a compound of Formula (I), wherein $R_2$ is —$C(O)N(R_4)(R_5)$. In some embodiments is a compound of Formula (I), wherein $R_5$ is $C_1$-$C_{25}$alkyl. In some embodiments is a compound of Formula (I), wherein $R_5$ is $C_1$-$C_{10}$alkyl. In some embodiments is a compound of Formula (I), wherein $R_5$ is $C_1$-$C_5$alkyl. In some embodiments is a compound of Formula (I), wherein $R_5$ is —$CH_3$. In some embodiments is a compound of Formula (I), wherein $R_1$ is $C_1$-$C_6$alkyl. In some embodiments is a compound of Formula (I), wherein $R_1$ is $C_1$-$C_3$alkyl. In some embodiments is a compound of Formula (I), wherein $R_1$ is —$CH_3$. In some embodiments is a compound of Formula (I), wherein $R_1$ is —$CH_2CH_3$. In some embodiments is a compound of Formula (I), wherein $R_1$ is hydrogen. In some embodiments is a compound of Formula (I), wherein p is 1. In some embodiments is a compound of Formula (I), wherein p is 2.

In some embodiments is a compound of Formula (I), wherein Y is

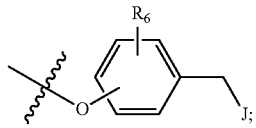

$R_6$ is independently selected from hydrogen, halogen, —CN, —$NH_2$, —$NH(CH_3)$, —$N(CH_3)_2$, —OH, —$CO_2H$, —$C(O)OC_1$-$C_6$alkyl, —$C(O)NH_2$, —$C(O)NH(C_1$-$C_6$alkyl), —$C(O)N(C_1$-$C_6$alkyl)$_2$, —$SO_2NH_2$, —$SO_2NH(C_1$-$C_6$alkyl), —$SO_2N(C_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone; J is —$NHC(O)R_7$ or —$C(O)OR_7$; and $R_7$ is $C_1$-$C_{12}$alkyl optionally substituted with one or more groups selected from halogen, —CN, —$NH_2$, —$NH(CH_3)$, —$N(CH_3)_2$, —OH, —$CO_2H$, —$C(O)OC_1$-$C_6$alkyl, —$C(O)NH_2$, —$C(O)NH(C_1$-$C_6$alkyl), —$C(O)N(C_1$-$C_6$alkyl)$_2$, —$SO_2NH_2$, —$SO_2NH(C_1$-$C_6$alkyl), —$SO_2N(C_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone. In another embodiment is a compound of Formula (I), wherein J is —NHC(O)$R_7$. In another embodiment is a compound of Formula (I), wherein J is —C(O)O$R_7$. In another embodiment is a compound of Formula (I), wherein $R_7$ is unsubstituted $C_1$-$C_{12}$alkyl. In another embodiment is a compound of Formula (I), wherein $R_6$ is $C_1$-$C_6$alkoxy. In some embodiments is a compound of Formula (I), wherein Y is

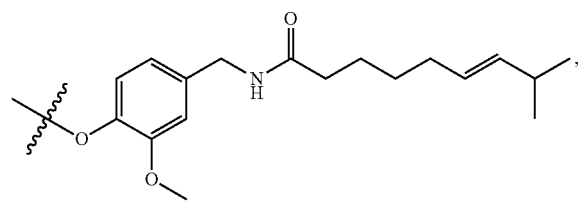 [SMILES: *Oc1ccc(CNC(=O)CCCC/C=C/C(C)C)cc1OC]

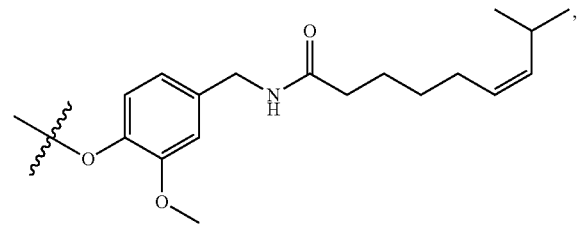

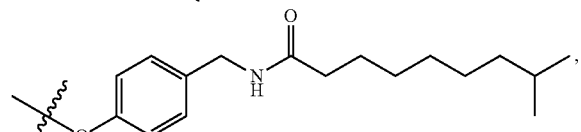

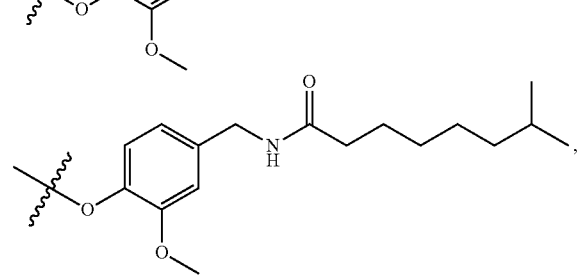

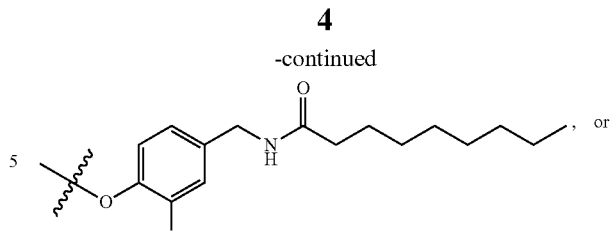, or

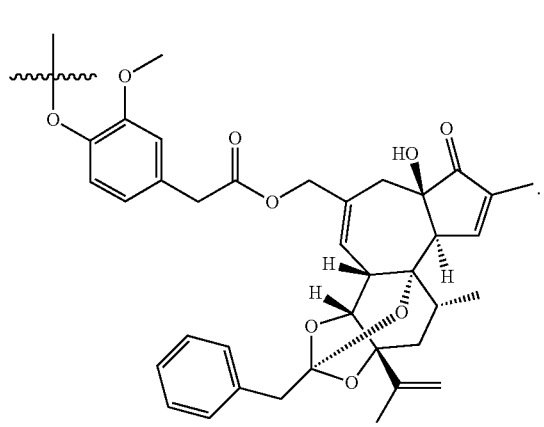

In some embodiments is a compound of Formula (I), wherein Y is

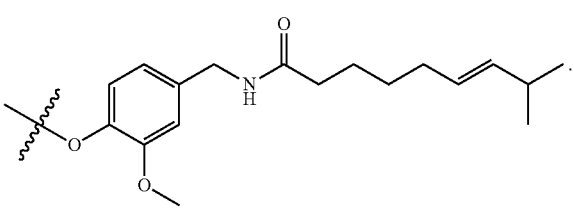

In some embodiments is a compound, or a pharmaceutically acceptable salt, pharmaceutically acceptable solvate, or hydrate thereof, having the structure:

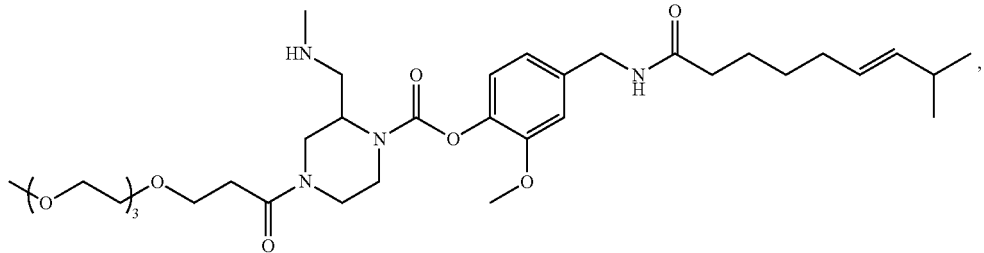

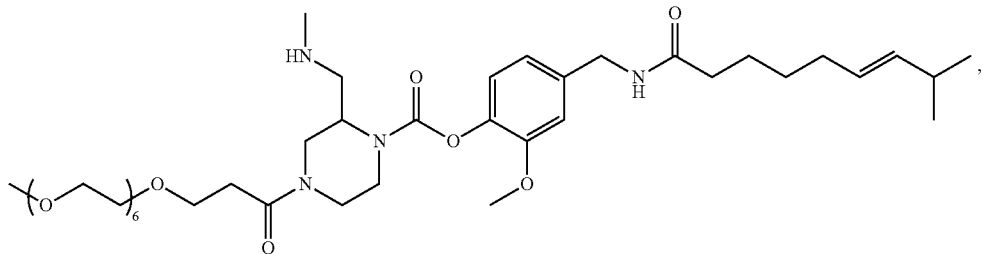

-continued

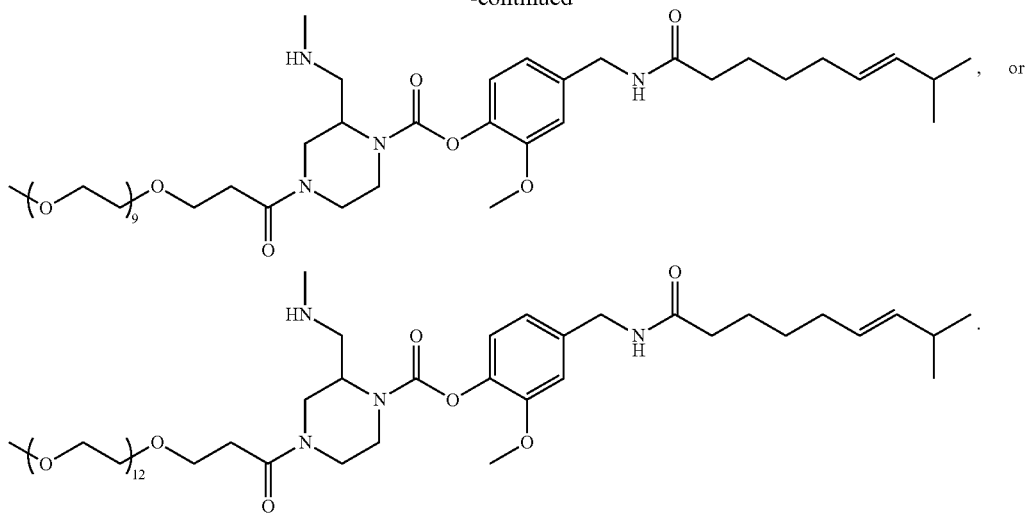

In some embodiments is a compound, or a pharmaceutically acceptable salt, pharmaceutically acceptable solvate, or hydrate thereof, having the structure:

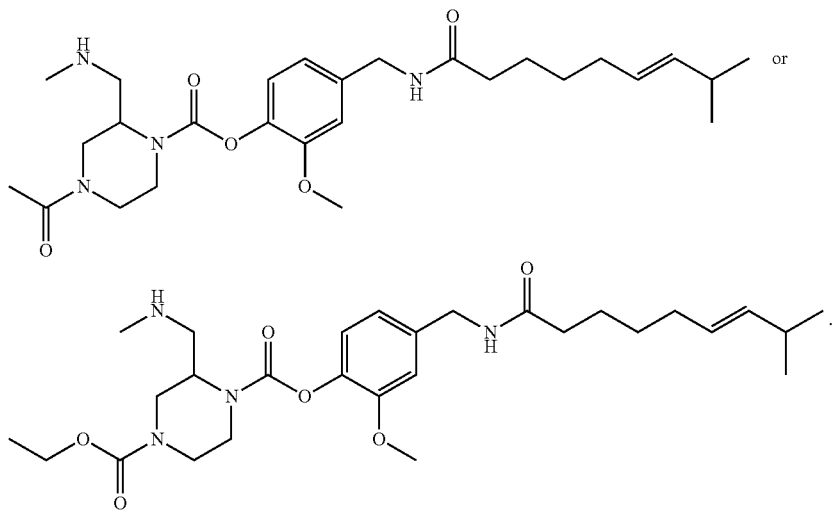

In another aspect is a pharmaceutical composition comprising a compound of Formula (I), or a pharmaceutically acceptable salt, pharmaceutically acceptable solvate, or hydrate thereof, and a pharmaceutically acceptable diluent, excipient or binder.

In another aspect is a pharmaceutical composition comprising a compound of Formula (I), or a pharmaceutically acceptable salt, pharmaceutically acceptable solvate, or hydrate thereof, and a pharmaceutically acceptable diluent, excipient or binder. In some embodiments, the pharmaceutical composition is formulated for intravenous injection, epidural injection, subcutaneous injection, intramuscular injection, intraperitoneal injection, perineural injection, neuraxial injection, intra-articular injection, oral administration, or topical administration.

In another aspect is a method of treating pain in a subject, comprising administering to the subject a therapeutically effective amount of a compound of Formula (I), or a pharmaceutically acceptable salt, pharmaceutically acceptable solvate, or hydrate thereof. In some embodiments is a method of treating pain in a subject, comprising administering to the subject a therapeutically effective amount of a compound of Formula (I), or a pharmaceutically acceptable salt, pharmaceutically acceptable solvate, or hydrate thereof, wherein the pain is associated with cancer.

DETAILED DESCRIPTION

Figure 1:
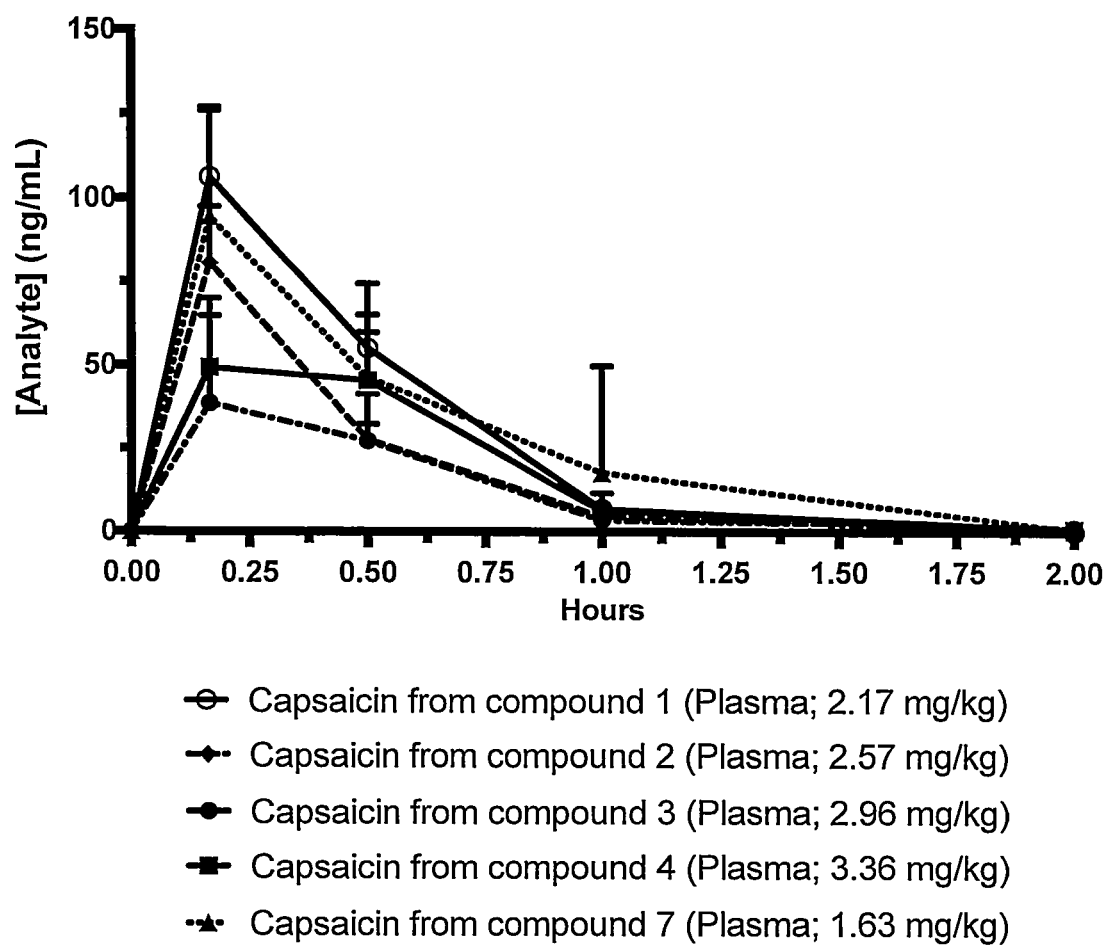
FIG. 1 shows the plasma concentration (ng/mL) time course of capsaicin following epidural dosing of compounds 1, 2, 3, 4, and 7 in rats.

Capsaicin, the main ingredient responsible for the hot pungent taste of chili peppers, is an alkaloid found in the Capsicum family. Capsaicin (8-methyl-N-vanillyl-6-nonenamide) is a highly selective agonist for transient receptor potential vanilloid 1 receptor (TRPV1; formerly known as vanilloid receptor 1 (VR1)), a ligand-gated, non-selective cation channel. TRPV1 is preferentially expressed on small-diameter sensory neurons, especially those A- and C-fibers which specialize in the detection of painful or noxious sensations. TRPV1 responds to noxious stimuli including capsaicin, heat, and extracellular acidification, and will integrate simultaneous exposures to these stimuli. (Caterina M J, Julius D. The vanilloid receptor: a molecular gateway to the pain pathway. *Annu Rev Neurosci.* 2001. 24:487-517).

TRPV1 agonists, such as capsaicin, have been shown to diminish pain in various settings, but there are problems associated with their use. The initial effects of TRPV1-expressing (capsaicin-sensitive) nociceptors activation are burning sensations, hyperalgesia, allodynia, and erythema. However, after prolonged exposure to low-concentration capsaicin or single exposures to high-concentration capsaicin or other TRPV1 agonists, the small-diameter sensory axons become less sensitive to a variety of stimuli, including capsaicin or thermal stimuli. This prolonged exposure is also characterized by reduced pain responses. These later-stage effects of capsaicin are frequently referred to as "desensitization" and are the rationale for the development of capsaicin formulations for the treatment of various pain syndromes and other conditions. (Bley, K. R. Recent developments in transient receptor potential vanilloid receptor 1 agonist-based therapies. *Expert Opin Investig Drugs.* 2004. 13(11): 1445-1456).

In addition, capsaicin and other TRPV1 agonists have very limited water solubility, are extremely potent irritants requiring special equipment when handling and, due to their limited water solubility, are not readily mixed with common drugs that are procured as aqueous solutions. Therefore, the use of non-aqueous formulations is necessary to deliver substantial quantities of capsaicin or other TRPV1 agonists. These formulations are frequently not aligned with current practices/procedures, especially with respect to sterile aqueous solutions used in surgery. Additionally, due to the potent ability of capsaicin to cause irritation, it would be preferable to utilize a water-soluble prodrug of capsaicin that minimizes capsaicin's activity until the prodrug reaches the desired site of activity.

In some embodiments described herein are prodrugs suitable for parenteral dosing having aqueous solution state stability at pHs suitable for parenteral administration (e.g. pH 4.5±1.0) to provide a reasonable time window for the holding/manipulation of dose formulations of the prodrugs prior to administration (e.g. 0-4 hours) without substantial conversion to the active drug, including but not limited to capsaicin. Described herein are prodrugs of capsaicin that demonstrate stability in aqueous solutions at appropriate pH for parenteral administration including, but not limited to, pH 4.5.

Lastly, the introduction of various length PEG moieties to the prodrugs provides an opportunity to modulate the physiochemical and pharmacokinetic properties of the prodrug and their resulting cyclic urea upon conversion. In some embodiments, tuning the pharmacokinetic profile of the prodrugs and the resulting cyclic urea involves reduced CSF penetration of the cyclic ureas following epidural administration of the prodrugs.

Thus, in some embodiments, it would be desirable to provide TRPV1 agonist prodrugs with: 1) increased water solubility (relative to capsaicin) and, in turn, it would be desirable to provide TRPV1 agonist prodrugs that are soluble in commonly used aqueous/sterile injectable formulations to an intended site of action, 2) the potential for reduced or delayed pungency associated with the administration of TRPV1 agonists and 3) have the ability to be delivered in a rapid manner (half-life of delivery of TRPV1 agonist in less than 30 min, or more preferably in less than 15 min), 4) desirable, aqueous solution state stability for the prodrugs, especially at pH's that are suitable for parenteral administration (e.g. pH 4.5±1.0) and finally 5) prodrugs and their resultant cyclic ureas that demonstrate modified pharmacokinetic profiles over non-PEGylated prodrugs and their resultant cyclic ureas (e.g. reduced CSF exposure of the prodrug and the corresponding cyclic urea). Additionally, in some embodiments, it would be desirable to deliver another pharmacologically active compound(s) along with a capsaicin prodrug or other TRPV1 agonist prodrug including, but not limited to, a local anesthetic agent.

Accordingly, the compounds described herein are directed to novel water-soluble prodrugs of TRPV1 agonists and their methods of synthesis and use. These TRPV1 agonist prodrugs rapidly convert to the active parent compound when exposed to physiological conditions. The compounds described herein have significantly higher hydrophilicity/water solubility than their parent drugs (e.g. capsaicin) and, hence, are better able to be incorporated into aqueous formulations. Described herein is a method of increasing the water solubility of capsaicin, its analogs and other TRPV1 agonists, by modifying the prodrug molecule's chemical structure with hydrophilic moieties (e.g. PEG moiety). In some embodiments described herein, the introduction of basic moieties capable of being protonated under acidic conditions increases the solubility of the TRPV1 prodrug. The prodrugs described herein are designed such that the parent drug is released, via cyclization-release reactions, under well-defined rates after the prodrug has been delivered to the body and/or is exposed to physiological conditions. The chemical-release kinetics of the parent drug may impart two important properties: (a) potentially reduced and/or delayed pungency due to the avoidance of the rapid delivery of a bolus dose of the TRPV1 agonist and (b) rapid or delayed release of the parent TRPV1 agonist from the prodrug for tuning of specific pharmacological activity/results. In some embodiments, such structural modifications eliminate the reliance on special requirements for formulations or delivery devices in order to 1) accommodate the very low water solubility of many TRPV1 agonists/capsaicinoids and 2) reduce the acute pungency associated with the administration of TRPV1 agonists. Additionally, water-soluble prodrugs are desired when co-delivering other medications, especially when administering multiple sterile agents via injection.

Additionally, in some embodiments, PEG moieties have been introduced to modulate both the physiochemical and pharmacokinetic properties of the prodrugs and their resultant cyclization-released cyclic ureas. The introduction of the PEG moieties allows for the potential to modulate the pharmacokinetics of both the prodrugs and their resultant cyclic ureas, due to the ability to: 1) modify the overall size and polarity and 2) increase the molecular weights from the "base" (e.g. non-PEGylated) prodrugs/cyclic ureas. As the size or length of the PEG groups increase, there is a corresponding influence on the solubility of the prodrugs in aqueous media. Along with an impact on the aqueous solubility, an increase of the attached PEG chain length can modulate the ability of the prodrug and cyclic ureas to access certain biological barriers (e.g. the blood-brain barrier or into CSF) and, hence, modify their pharmacokinetic properties.

Capsaicin, capsaicinoids or other TRPV1 agonist prodrugs described herein are chemically modified to control the rate at which the capsaicin, capsaicinoid, or other TRPV1 agonist is bioavailable through a pH controlled, intramolecular cyclization-release reaction. In some embodiments, the TRPV1 agonist prodrugs described herein have prolonged stability at pH levels suitable for making pharmaceutical formulations, but convert rapidly in vivo (under physiological conditions) in a well-controlled manner. After parenteral administration, the compounds of Formula (I) or (II) are converted to the parent drug (TRPV1 agonist) via a temperature and pH regulated cyclization-release reaction. The rate at which the prodrug converts is dictated by the cyclization-release reaction, which can be modified by the addition of buffers. In some embodiments, a buffer could provide a time window where turnover to parent drug is significantly delayed until the return of physiological conditions. In embodiments described herein, the parent drug is released by an amine-based intramolecular cyclization:

Cyclization Release of Compound 1 through 8

[Structure of prodrug compound]

Compound 1 (R═C(O)-C2-PEG3-OMe)
Compound 2 (R═C(O)-C2-PEG6-OMe)
Compound 3 (R═C(O)-C2-PEG9-OMe)
Compound 4 (R═C(O)-C2-PEG12-OMe)
Compound 5 (R═H)
Compound 6 (R═Me)
Compound 7 (R═Ac)
Compound 8 (R═C(O)OEt)

↓ Cyclization Release

[Structure of Capsaicin]

Capsaicin

+

[Structure of cyclic urea]

Cyclic urea of Compound 1 (R═C(O)-C2-PEG3-OMe)
Cyclic urea of Compound 2 (R═C(O)-C2-PEG6-OMe)
Cyclic urea of Compound 3 (R═C(O)-C2-PEG9-OMe)
Cyclic urea of Compound 4 (R═C(O)-C2-PEG12-OMe)
Cyclic urea of Compound 5 (R═H)
Cyclic urea of Compound 6 (R═Me)
Cyclic urea of Compound 7 (R═Ac)
Cyclic urea of Compound 8 (R═C(O)OEt)

In some embodiments, the cyclization rate ($t_{1/2}$) of a compound of Formula (I) or (II) at 37° C., pH 7.4, is between 10 seconds and 10 hours. In some embodiments, the cyclization rate ($t_{1/2}$) at 37° C., pH 7.4, is between 10 seconds and 1 hour. In some embodiments, the cyclization rate ($t_{1/2}$) at 37° C., pH 7.4, is between 10 seconds and 30 minutes. In some embodiments, the cyclization rate ($t_{1/2}$) at 37° C., pH 7.4, is between 1 minute and 10 hours. In some embodiments, the cyclization rate ($t_{1/2}$) at 37° C., pH 7.4, is between 1 minute and 30 minutes. In some embodiments, the cyclization rate ($t_{1/2}$) at 37° C., pH 7.4, is between 2 minutes and 30 minutes. In some embodiments, the cyclization rate ($t_{1/2}$) at 37° C., pH 7.4, is between 5 minutes and 30 minutes. In some embodiments, the cyclization rate ($t_{1/2}$) at 37° C., pH 7.4, is between 2 minutes and 15 minutes. In some embodiments, the cyclization rate ($t_{1/2}$) at 37° C., pH 7.4, is between 5 minutes and 15 minutes. In some embodiments, the cyclization rate ($t_{1/2}$) at 37° C., pH 7.4, is between 15 minutes and 2 hours. In some embodiments, the cyclization rate ($t_{1/2}$) at 37° C., pH 7.4, is between 15 minutes and 1.5 hours. In some embodiments, the cyclization rate ($t_{1/2}$) at 37° C., pH 7.4, is between 15 minutes and 1 hour. In some embodiments, the cyclization rate ($t_{1/2}$) at 37° C., pH 7.4, is between 30 minutes and 2 hours. In some embodiments, the cyclization rate ($t_{1/2}$) at 37° C., pH 7.4, is between 30 minutes and 1.5 hours. In some embodiments, the cyclization rate ($t_{1/2}$) at 37° C., pH 7.4, is between 30 minutes and 1 hour. In some embodiments, the cyclization rate ($t_{1/2}$) at 37° C., pH 7.4, is between 1 hour and 4 hours. In some embodiments, the cyclization rate ($t_{1/2}$) at 37° C., pH 7.4, is between 1 hour and 3 hours. In some embodiments, the cyclization rate ($t_{1/2}$) at 37° C., pH 7.4, is between 1 hour and 2 hours. In some embodiments, the cyclization rate ($t_{1/2}$) at 37° C., pH 7.4, is between 2 hours and 10 hours. In some embodiments, the cyclization rate ($t_{1/2}$) at 37° C., pH 7.4, is between 2 hours and 6 hours. In some embodiments, the cyclization rate ($t_{1/2}$) at 37° C., pH 7.4, is between 2 hours and 4 hours. In some embodiments, the cyclization rate ($t_{1/2}$) at 37° C., pH 7.4, is between 2 hours and 3 hours. In some embodiments, the cyclization rate ($t_{1/2}$) at 37° C., pH 7.4, is between 3 hours and 5 hours. In some embodiments, the cyclization rate ($t_{1/2}$) at 37° C., pH 7.4, is between 4 hours and 6 hours. In some embodiments, the cyclization rate ($t_{1/2}$) at 37° C., pH 7.4, is between 5 hours and 7 hours. In some embodiments, the cyclization rate ($t_{1/2}$) at 37° C., pH 7.4, is between 6 hours and 8 hours. In some embodiments, the cyclization rate ($t_{1/2}$) at 37° C., pH 7.4, is between 7 hours and 9 hours. In some embodiments, the cyclization rate ($t_{1/2}$) at 37° C., pH 7.4, is between 8 hours and 10 hours.

Compounds

In another embodiment, described herein is a compound having the structure of Formula (I):

Formula (I)

wherein:

Y is a phenolic TRPV1 agonist, wherein the hydrogen atom of the phenolic hydroxyl group is replaced by a covalent bond to $R_1$ is hydrogen or $C_1$-$C_6$alkyl;
$R_2$ is —$(CH_2CH_2O)_nR_3$, —$C(O)(CH_2)_mO(CH_2CH_2O)_nR_3$, —$C(O)O(CH_2CH_2O)_nR_3$, —$C(O)N(R_4)(CH_2CH_2O)_nR_3$, —$C(O)R_5$, —$C(O)OR_5$, or —$C(O)N(R_4)(R_5)$;
$R_3$ is hydrogen or $C_1$-$C_6$alkyl;
$R_4$ is hydrogen or $C_1$-$C_6$alkyl;
$R_5$ is $C_1$-$C_{50}$alkyl;
m is 1-10;
n is 1-50; and
p is 1-9;
or a pharmaceutically acceptable salt, pharmaceutically acceptable solvate, or hydrate thereof.

In some embodiments is a compound of Formula (I), wherein $R_2$ is —$(CH_2CH_2O)_nR_3$, —$C(O)(CH_2)_mO(CH_2CH_2O)_nR_3$, —$C(O)O(CH_2CH_2O)_nR_3$, or —$C(O)N(R_4)(CH_2CH_2O)_nR_3$.

In some embodiments is a compound of Formula (I), wherein $R_2$ is —$(CH_2CH_2O)_nR_3$. In some embodiments is a compound of Formula (I), wherein $R_2$ is —$(CH_2CH_2O)_nR_3$ and $R_3$ is hydrogen. In some embodiments is a compound of Formula (I), wherein $R_2$ is —$(CH_2CH_2O)_nR_3$ and $R_3$ is $C_1$-$C_6$alkyl. In some embodiments is a compound of Formula (I), wherein $R_2$ is —$(CH_2CH_2O)_nR_3$ and $R_3$ is $C_1$-$C_3$alkyl. In some embodiments is a compound of Formula (I), wherein $R_2$ is —$(CH_2CH_2O)_nR_3$ and $R_3$ is —$CH_3$. In some embodiments is a compound of Formula (I), wherein $R_2$ is —$(CH_2CH_2O)_nR_3$ and $R_3$ is —$CH_2CH_3$.

In some embodiments is a compound of Formula (I), wherein $R_2$ is —$C(O)(CH_2)_mO(CH_2CH_2O)_nR_3$. In some embodiments is a compound of Formula (I), wherein $R_2$ is —$C(O)(CH_2)_mO(CH_2CH_2O)_nR_3$ and $R_3$ is hydrogen. In some embodiments is a compound of Formula (I), wherein $R_2$ is —$C(O)(CH_2)_mO(CH_2CH_2O)_nR_3$ and $R_3$ is $C_1$-$C_6$alkyl. In some embodiments is a compound of Formula (I), wherein $R_2$ is —$C(O)(CH_2)_mO(CH_2CH_2O)_nR_3$ and $R_3$ is $C_1$-$C_3$alkyl. In some embodiments is a compound of Formula (I), wherein $R_2$ is —$C(O)(CH_2)_mO(CH_2CH_2O)_nR_3$ and $R_3$ is —$CH_3$. In some embodiments is a compound of Formula (I), wherein $R_2$ is —$C(O)(CH_2)_mO(CH_2CH_2O)_nR_3$ and $R_3$ is —$CH_2CH_3$.

In some embodiments is a compound of Formula (I), wherein $R_2$ is —$C(O)O(CH_2CH_2O)_nR_3$. In some embodiments is a compound of Formula (I), wherein $R_2$ is —$C(O)O(CH_2CH_2O)_nR_3$ and $R_3$ is hydrogen. In some embodiments is a compound of Formula (I), wherein $R_2$ is —$C(O)O(CH_2CH_2O)_nR_3$ and $R_3$ is $C_1$-$C_6$alkyl. In some embodiments is a compound of Formula (I), wherein $R_2$ is —$C(O)O(CH_2CH_2O)_nR_3$ and $R_3$ is $C_1$-$C_3$alkyl. In some embodiments is a compound of Formula (I), wherein $R_2$ is —$C(O)O(CH_2CH_2O)_nR_3$ and $R_3$ is —$CH_3$. In some embodiments is a compound of Formula (I), wherein $R_2$ is —$C(O)O(CH_2CH_2O)_nR_3$ and $R_3$ is —$CH_2CH_3$.

In some embodiments is a compound of Formula (I), wherein $R_2$ is —$C(O)N(R_4)(CH_2CH_2O)_nR_3$. In some embodiments is a compound of Formula (I), wherein $R_2$ is —$C(O)N(R_4)(CH_2CH_2O)_nR_3$ and $R_3$ is hydrogen. In some embodiments is a compound of Formula (I), wherein $R_2$ is —$C(O)N(R_4)(CH_2CH_2O)_nR_3$, $R_3$ is hydrogen, and $R_4$ is hydrogen. In some embodiments is a compound of Formula (I), wherein $R_2$ is —$C(O)N(R_4)(CH_2CH_2O)_nR_3$, $R_3$ is hydrogen, and $R_4$ is $C_1$-$C_6$alkyl. In some embodiments is a compound of Formula (I), wherein $R_2$ is —$C(O)N(R_4)(CH_2CH_2O)_nR_3$ and $R_3$ is $C_1$-$C_6$alkyl. In some embodiments is a compound of Formula (I), wherein $R_2$ is —$C(O)N(R_4)(CH_2CH_2O)_nR_3$, $R_3$ is $C_1$-$C_6$alkyl, and $R_4$ is hydrogen. In some embodiments is a compound of Formula (I), wherein $R_2$ is —$C(O)N(R_4)(CH_2CH_2O)_nR_3$, $R_3$ is $C_1$-$C_6$alkyl, and $R_4$ is $C_1$-$C_6$alkyl. In some embodiments is a compound of Formula (I), wherein $R_2$ is —$C(O)N(R_4)(CH_2CH_2O)_nR_3$ and $R_3$ is $C_1$-$C_3$alkyl. In some embodiments is a compound of Formula (I), wherein $R_2$ is —$C(O)N(R_4)(CH_2CH_2O)_nR_3$, $R_3$ is $C_1$-$C_3$alkyl, and $R_4$ is hydrogen. In some embodiments is a compound of Formula (I), wherein $R_2$ is —$C(O)N(R_4)(CH_2CH_2O)_nR_3$, $R_3$ is $C_1$-$C_3$alkyl, and $R_4$ is $C_1$-$C_6$alkyl. In some embodiments is a compound of Formula (I), wherein $R_2$ is —$C(O)N(R_4)(CH_2CH_2O)_nR_3$ and $R_3$ is —$CH_3$. In some embodiments is a compound of Formula (I), wherein $R_2$ is —$C(O)N(R_4)(CH_2CH_2O)_nR_3$, $R_3$ is —$CH_3$, and $R_4$ is hydrogen. In some embodiments is a compound of Formula (I), wherein $R_2$ is —$C(O)N(R_4)(CH_2CH_2O)_nR_3$, $R_3$ is —$CH_3$, and $R_4$ is $C_1$-$C_6$alkyl. In some embodiments is a compound of Formula (I), wherein $R_2$ is —$C(O)N(R_4)(CH_2CH_2O)_nR_3$ and $R_3$ is —$CH_2CH_3$. In some embodiments is a compound of Formula (I), wherein $R_2$ is —$C(O)N(R_4)(CH_2CH_2O)_nR_3$, $R_3$ is —$CH_2CH_3$, and $R_4$ is hydrogen. In some embodiments is a compound of Formula (I), wherein $R_2$ is —$C(O)N(R_4)(CH_2CH_2O)_nR_3$, $R_3$ is —$CH_2CH_3$, and $R_4$ is $C_1$-$C_6$alkyl.

In some embodiments is a compound of Formula (I), wherein $R_2$ is —$C(O)R_5$. In some embodiments is a compound of Formula (I), wherein $R_2$ is —$C(O)R_5$ and $R_5$ is $C_1$-$C_{45}$alkyl. In some embodiments is a compound of Formula (I), wherein $R_2$ is —$C(O)R_5$ and $R_5$ is $C_1$-$C_{40}$alkyl. In some embodiments is a compound of Formula (I), wherein $R_2$ is —$C(O)R_5$ and $R_5$ is $C_1$-$C_{35}$alkyl. In some embodiments is a compound of Formula (I), wherein $R_2$ is —$C(O)R_5$ and $R_5$ is $C_1$-$C_{30}$alkyl. In some embodiments is a compound of Formula (I), wherein $R_2$ is —$C(O)R_5$ and $R_5$ is $C_1$-$C_{25}$alkyl. In some embodiments is a compound of Formula (I), wherein $R_2$ is —$C(O)R_5$ and $R_5$ is $C_1$-$C_{20}$alkyl. In some embodiments is a compound of Formula (I), wherein $R_2$ is —$C(O)R_5$ and $R_5$ is $C_1$-$C_{15}$alkyl. In some embodiments is a compound of Formula (I), wherein $R_2$ is —$C(O)R_5$ and $R_5$ is $C_1$-$C_{10}$alkyl. In some embodiments is a compound of Formula (I), wherein $R_2$ is —C(O)$R_5$ and $R_5$ is $C_1$-$C_5$alkyl. In some embodiments is a compound of Formula (I), wherein $R_2$ is —C(O)$R_5$ and $R_5$ is —CH$_2$CH$_3$. In some embodiments is a compound of Formula (I), wherein $R_2$ is —C(O)$R_5$ and $R_5$ is —CH$_3$.

In some embodiments is a compound of Formula (I), wherein $R_2$ is —C(O)O$R_5$. In some embodiments is a compound of Formula (I), wherein $R_2$ is —C(O)O$R_5$ and $R_5$ is $C_1$-$C_{45}$alkyl. In some embodiments is a compound of Formula (I), wherein $R_2$ is —C(O)O$R_5$ and $R_5$ is $C_1$-$C_{40}$alkyl. In some embodiments is a compound of Formula (I), wherein $R_2$ is —C(O)O$R_5$ and $R_5$ is $C_1$-$C_{35}$alkyl. In some embodiments is a compound of Formula (I), wherein $R_2$ is —C(O)O$R_5$ and $R_5$ is $C_1$-$C_{30}$alkyl. In some embodiments is a compound of Formula (I), wherein $R_2$ is —C(O)O$R_5$ and $R_5$ is $C_1$-$C_{25}$alkyl. In some embodiments is a compound of Formula (I), wherein $R_2$ is —C(O)O$R_5$ and $R_5$ is $C_1$-$C_{20}$alkyl. In some embodiments is a compound of Formula (I), wherein $R_2$ is —C(O)O$R_5$ and $R_5$ is $C_1$-$C_{15}$alkyl. In some embodiments is a compound of Formula (I), wherein $R_2$ is —C(O)O$R_5$ and $R_5$ is $C_1$-$C_{10}$alkyl. In some embodiments is a compound of Formula (I), wherein $R_2$ is —C(O)O$R_5$ and $R_5$ is $C_1$-$C_5$alkyl. In some embodiments is a compound of Formula (I), wherein $R_2$ is —C(O)O$R_5$ and $R_5$ is —CH$_2$CH$_3$. In some embodiments is a compound of Formula (I), wherein $R_2$ is —C(O)O$R_5$ and $R_5$ is —CH$_3$.

In some embodiments is a compound of Formula (I), wherein $R_2$ is —C(O)N($R_4$)($R_5$). In some embodiments is a compound of Formula (I), wherein $R_2$ is —C(O)N($R_4$)($R_5$), $R_4$ is H, and $R_5$ is $C_1$-$C_{45}$alkyl. In some embodiments is a compound of Formula (I), wherein $R_2$ is —C(O)N($R_4$)($R_5$), $R_4$ is H, and $R_5$ is $C_1$-$C_{40}$alkyl. In some embodiments is a compound of Formula (I), wherein $R_2$ is —C(O)N($R_4$)($R_5$), $R_4$ is H, and $R_5$ is $C_1$-$C_{35}$alkyl. In some embodiments is a compound of Formula (I), wherein $R_2$ is —C(O)N($R_4$)($R_5$), $R_4$ is H, and $R_5$ is $C_1$-$C_{30}$alkyl. In some embodiments is a compound of Formula (I), wherein $R_2$ is-C(O)N($R_4$)($R_5$), $R_4$ is H, and $R_5$ is $C_1$-$C_{25}$alkyl. In some embodiments is a compound of Formula (I), wherein $R_2$ is —C(O)N($R_4$)($R_5$), $R_4$ is H, and $R_5$ is $C_1$-$C_{20}$alkyl. In some embodiments is a compound of Formula (I), wherein $R_2$ is —C(O)N($R_4$)($R_5$), $R_4$ is H, and $R_5$ is $C_1$-$C_{15}$alkyl. In some embodiments is a compound of Formula (I), wherein $R_2$ is —C(O)N($R_4$)($R_5$), $R_4$ is H, and $R_5$ is $C_1$-$C_{10}$alkyl. In some embodiments is a compound of Formula (I), wherein $R_2$ is —C(O)N($R_4$)($R_5$), $R_4$ is H, and $R_5$ is $C_1$-$C_5$alkyl. In some embodiments is a compound of Formula (I), wherein $R_2$ is —C(O)N($R_4$)($R_5$), $R_4$ is H, and $R_5$ is —CH$_2$CH$_3$. In some embodiments is a compound of Formula (I), wherein $R_2$ is —C(O)N($R_4$)($R_5$), $R_4$ is H, and $R_5$ is —CH$_3$.

In some embodiments is a compound of Formula (I), wherein $R_2$ is —C(O)N($R_4$)($R_5$), $R_4$ is $C_1$-$C_6$alkyl, and $R_5$ is $C_1$-$C_{45}$alkyl. In some embodiments is a compound of Formula (I), wherein $R_2$ is —C(O)N($R_4$)($R_5$), $R_4$ is $C_1$-$C_6$alkyl, and $R_5$ is $C_1$-$C_{40}$alkyl. In some embodiments is a compound of Formula (I), wherein $R_2$ is —C(O)N($R_4$)($R_5$), $R_4$ is $C_1$-$C_6$alkyl, and $R_5$ is $C_1$-$C_{35}$alkyl. In some embodiments is a compound of Formula (I), wherein $R_2$ is —C(O)N($R_4$)($R_5$), $R_4$ is $C_1$-$C_6$alkyl, and $R_5$ is $C_1$-$C_{30}$alkyl. In some embodiments is a compound of Formula (I), wherein $R_2$ is —C(O)N($R_4$)($R_5$), $R_4$ is $C_1$-$C_6$alkyl, and $R_5$ is $C_1$-$C_{25}$alkyl. In some embodiments is a compound of Formula (I), wherein $R_2$ is —C(O)N($R_4$)($R_5$), $R_4$ is $C_1$-$C_6$alkyl, and $R_5$ is $C_1$-$C_{20}$alkyl. In some embodiments is a compound of Formula (I), wherein $R_2$ is —C(O)N($R_4$)($R_5$), $R_4$ is $C_1$-$C_6$alkyl, and $R_5$ is $C_1$-$C_{15}$alkyl. In some embodiments is a compound of Formula (I), wherein $R_2$ is —C(O)N($R_4$)($R_5$), $R_4$ is $C_1$-$C_6$alkyl, and $R_5$ is $C_1$-$C_{10}$alkyl. In some embodiments is a compound of Formula (I), wherein $R_2$ is —C(O)N($R_4$)($R_5$), $R_4$ is $C_1$-$C_6$alkyl, and $R_5$ is $C_1$-$C_5$alkyl. In some embodiments is a compound of Formula (I), wherein $R_2$ is —C(O)N($R_4$)($R_5$), $R_4$ is $C_1$-$C_6$alkyl, and $R_5$ is —CH$_2$CH$_3$. In some embodiments is a compound of Formula (I), wherein $R_2$ is —C(O)N($R_4$)($R_5$), $R_4$ is $C_1$-$C_6$alkyl, and $R_5$ is —CH$_3$. In some embodiments is a compound of Formula (I), wherein $R_2$ is —C(O)N($R_4$)($R_5$), $R_4$ is —CH$_3$, and $R_5$ is —CH$_2$CH$_3$. In some embodiments is a compound of Formula (I), wherein $R_2$ is —C(O)N($R_4$)($R_5$), $R_4$ is —CH$_3$, and $R_5$ is —CH$_3$.

In some embodiments is a compound of Formula (I), wherein m is 1-5. In some embodiments is a compound of Formula (I), wherein m is 2-10. In some embodiments is a compound of Formula (I), wherein m is 4-10. In some embodiments is a compound of Formula (I), wherein m is 2-8. In some embodiments is a compound of Formula (I), wherein m is 2-6. In some embodiments is a compound of Formula (I), wherein m is 2-4. In some embodiments is a compound of Formula (I), wherein m is 1. In some embodiments is a compound of Formula (I), wherein m is 2. In some embodiments is a compound of Formula (I), wherein m is 3. In some embodiments is a compound of Formula (I), wherein m is 4. In some embodiments is a compound of Formula (I), wherein m is 5. In some embodiments is a compound of Formula (I), wherein m is 6. In some embodiments is a compound of Formula (I), wherein m is 7. In some embodiments is a compound of Formula (I), wherein m is 8. In some embodiments is a compound of Formula (I), wherein m is 9. In some embodiments is a compound of Formula (I), wherein m is 10.

In some embodiments is a compound of Formula (I), wherein n is 1-45. In some embodiments is a compound of Formula (I), wherein n is 1-40. In some embodiments is a compound of Formula (I), wherein n is 1-35. In some embodiments is a compound of Formula (I), wherein n is 1-30. In some embodiments is a compound of Formula (I), wherein n is 1-25. In some embodiments is a compound of Formula (I), wherein n is 1-20. In some embodiments is a compound of Formula (I), wherein n is 2-20. In some embodiments is a compound of Formula (I), wherein n is 2-16. In some embodiments is a compound of Formula (I), wherein n is 2-12. In some embodiments is a compound of Formula (I), wherein n is 2-10. In some embodiments is a compound of Formula (I), wherein n is 4-10. In some embodiments is a compound of Formula (I), wherein n is 1. In some embodiments is a compound of Formula (I), wherein n is 2. In some embodiments is a compound of Formula (I), wherein n is 3. In some embodiments is a compound of Formula (I), wherein n is 4. In some embodiments is a compound of Formula (I), wherein n is 5. In some embodiments is a compound of Formula (I), wherein n is 6. In some embodiments is a compound of Formula (I), wherein n is 7. In some embodiments is a compound of Formula (I), wherein n is 8. In some embodiments is a compound of Formula (I), wherein p is 9. In some embodiments is a compound of Formula (I), wherein n is 10. In some embodiments is a compound of Formula (I), wherein n is 11. In some embodiments is a compound of Formula (I), wherein p is 12. In some embodiments is a compound of Formula (I), wherein n is 13. In some embodiments is a compound of Formula (I), wherein n is 14. In some embodiments is a compound of Formula (I), wherein p is 15. In some embodiments is a compound of Formula (I), wherein n is 16.

In some embodiments is a compound of Formula (I), wherein p is 1. In some embodiments is a compound of Formula (I), wherein p is 2. In some embodiments is a compound of Formula (I), wherein p is 3. In some embodiments is a compound of Formula (I), wherein p is 4. In some embodiments is a compound of Formula (I), wherein p is 5. In some embodiments is a compound of Formula (I), wherein p is 6. In some embodiments is a compound of Formula (I), wherein p is 7. In some embodiments is a compound of Formula (I), wherein p is 8. In some embodiments is a compound of Formula (I), wherein p is 9.

In some embodiments is a compound of Formula (I), wherein $R_1$ is hydrogen. In some embodiments is a compound of Formula (I), wherein $R_1$ is $C_1$-$C_6$alkyl. In some embodiments is a compound of Formula (I), wherein $R_1$ is $C_1$-$C_3$alkyl. In some embodiments is a compound of Formula (I), wherein $R_1$ is —$CH_3$. In some embodiments is a compound of Formula (I), wherein $R_1$ is —$CH_2CH_3$.

In some embodiments is a compound of Formula (I), wherein p is 1 and $R_1$ is hydrogen. In some embodiments is a compound of Formula (I), wherein p is 1 and $R_1$ is $C_1$-$C_6$alkyl. In some embodiments is a compound of Formula (I), wherein p is 1 and $R_1$ is $C_1$-$C_3$alkyl. In some embodiments is a compound of Formula (I), wherein p is 1 and $R_1$ is —$CH_3$. In some embodiments is a compound of Formula (I), wherein p is 1 and $R_1$ is —$CH_2CH_3$. In some embodiments is a compound of Formula (I), wherein p is 2 and $R_1$ is hydrogen. In some embodiments is a compound of Formula (I), wherein p is 2 and $R_1$ is $C_1$-$C_6$alkyl. In some embodiments is a compound of Formula (I), wherein p is 2 and $R_1$ is $C_1$-$C_3$alkyl. In some embodiments is a compound of Formula (I), wherein p is 2 and $R_1$ is —$CH_3$. In some embodiments is a compound of Formula (I), wherein p is 2 and $R_1$ is —$CH_2CH_3$.

In some embodiments is a compound of Formula (I), wherein Y is

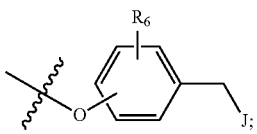

$R_6$ is independently selected from hydrogen, halogen, —CN, —$NH_2$, —NH($CH_3$), —N($CH_3$)$_2$, —OH, —$CO_2$H, —C(O)O$C_1$-$C_6$alkyl, —C(O)$NH_2$, —C(O)NH($C_1$-$C_6$alkyl), —C(O)N($C_1$-$C_6$alkyl)$_2$, —$SO_2NH_2$, —$SO_2$NH($C_1$-$C_6$alkyl), —$SO_2$N($C_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone; J is —NHC(O)$R_7$ or —C(O)O$R_7$; and $R_7$ is $C_1$-$C_{12}$alkyl optionally substituted with one or more groups selected from halogen, —CN, —$NH_2$, —NH($CH_3$), —N($CH_3$)$_2$, —OH, —$CO_2$H, —C(O)O$C_1$-$C_6$alkyl, —C(O)$NH_2$, —C(O)NH($C_1$-$C_6$alkyl), —C(O)N($C_1$-$C_6$alkyl)$_2$, —$SO_2NH_2$, —$SO_2$NH($C_1$-$C_6$alkyl), —$SO_2$N($C_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone.

In some embodiments is a compound of Formula (I), wherein Y is

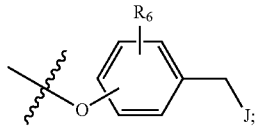

$R_6$ is independently selected from hydrogen, halogen, —CN, —$NH_2$, —NH($CH_3$), —N($CH_3$)$_2$, —OH, —$CO_2$H, —C(O)O$C_1$-$C_6$alkyl, —C(O)$NH_2$, —C(O)NH($C_1$-$C_6$alkyl), —C(O)N($C_1$-$C_6$alkyl)$_2$, —$SO_2NH_2$, —$SO_2$NH($C_1$-$C_6$alkyl), —$SO_2$N($C_1$-$C_6$alkyl)$_2$, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone; J is —NHC(O)$R_7$; and $R_7$ is $C_1$-$C_{12}$alkyl optionally substituted with one or more groups selected from halogen, —CN, —$NH_2$, —NH($CH_3$), —N($CH_3$)$_2$, —OH, —$CO_2$H, —C(O)O$C_1$-$C_6$alkyl, —C(O)$NH_2$, —C(O)NH($C_1$-$C_6$alkyl), —C(O)N($C_1$-$C_6$alkyl)$_2$, —$SO_2NH_2$, —$SO_2$NH($C_1$-$C_6$alkyl), —$SO_2$N($C_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone. In some embodiments is a compound of Formula (I), wherein Y is

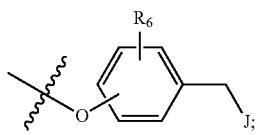

$R_6$ is independently selected from hydrogen, halogen, —CN, —$NH_2$, —NH($CH_3$), —N($CH_3$)$_2$, —OH, —$CO_2$H, —C(O)O$C_1$-$C_6$alkyl, —C(O)$NH_2$, —C(O)NH($C_1$-$C_6$alkyl), —C(O)N($C_1$-$C_6$alkyl)$_2$, —$SO_2NH_2$, —$SO_2$NH($C_1$-$C_6$alkyl), —$SO_2$N($C_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone; J is —C(O)O$R_7$; and $R_7$ is $C_1$-$C_{12}$alkyl optionally substituted with one or more groups selected from halogen, —CN, —$NH_2$, —NH($CH_3$), —N($CH_3$)$_2$, —OH, —$CO_2$H, —C(O)O$C_1$-$C_6$alkyl, —C(O)$NH_2$, —C(O)NH($C_1$-$C_6$alkyl), —C(O)N($C_1$-$C_6$alkyl)$_2$, —$SO_2NH_2$, —$SO_2$NH($C_1$-$C_6$alkyl), —$SO_2$N($C_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone.

In some embodiments is a compound of Formula (I), wherein Y is

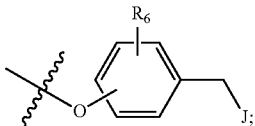

$R_6$ is $C_1$-$C_6$alkoxy; J is —NHC(O)$R_7$ or —C(O)O$R_7$; and $R_7$ is $C_1$-$C_{12}$alkyl optionally substituted with one or more groups selected from halogen, —CN, —NH$_2$, —NH(CH$_3$), —N(CH$_3$)$_2$, —OH, —CO$_2$H, —C(O)OC$_1$-$C_6$alkyl, —C(O)NH$_2$, —C(O)NH(C$_1$-$C_6$alkyl), —C(O)N(C$_1$-$C_6$alkyl)$_2$, —SO$_2$NH$_2$, —SO$_2$NH(C$_1$-$C_6$alkyl), —SO$_2$N(C$_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone. In some embodiments is a compound of Formula (I), wherein Y is

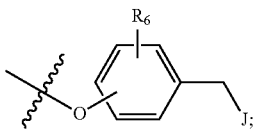

$R_6$ is $C_1$-$C_6$alkoxy; J is —NHC(O)$R_7$; and $R_7$ is $C_1$-$C_{12}$alkyl optionally substituted with one or more groups selected from halogen, —CN, —NH$_2$, —NH(CH$_3$), —N(CH$_3$)$_2$, —OH, —CO$_2$H, —C(O)OC$_1$-$C_6$alkyl, —C(O)NH$_2$, —C(O)NH(C$_1$-$C_6$alkyl), —C(O)N(C$_1$-$C_6$alkyl)$_2$, —SO$_2$NH$_2$, —SO$_2$NH(C$_1$-$C_6$alkyl), —SO$_2$N(C$_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone. In some embodiments is a compound of Formula (I), wherein Y is

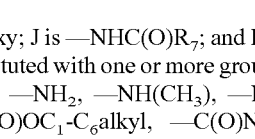

$R_6$ is $C_1$-$C_6$alkoxy; J is —C(O)O$R_7$; and $R_7$ is $C_1$-$C_{12}$alkyl optionally substituted with one or more groups selected from halogen, —CN, —NH$_2$, —NH(CH$_3$), —N(CH$_3$)$_2$, —OH, —CO$_2$H, —C(O)OC$_1$-$C_6$alkyl, —C(O)NH$_2$, —C(O)NH(C$_1$-$C_6$alkyl), —C(O)N(C$_1$-$C_6$alkyl)$_2$, —SO$_2$NH$_2$, —SO$_2$NH(C$_1$-$C_6$alkyl), —SO$_2$N(C$_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfoxide, $C_1$-$C_6$alkylsulfone, and $C_6$-$C_{10}$arylsulfone.

In some embodiments is a compound of Formula (I), wherein Y is

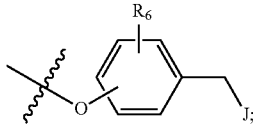

$R_6$ is independently selected from hydrogen, halogen, —CN, —NH$_2$, —NH(CH$_3$), —N(CH$_3$)$_2$, —OH, —CO$_2$H, —C(O)OC$_1$-$C_6$alkyl, —C(O)NH$_2$, —C(O)NH(C$_1$-$C_6$alkyl), —C(O)N(C$_1$-$C_6$alkyl)$_2$, —SO$_2$NH$_2$, —SO$_2$NH(C$_1$-$C_6$alkyl), —SO$_2$N(C$_1$-$C_6$alkyl)$_2$, $C_1$-$C_6$alkyl, $C_3$-$C_8$cycloalkyl, $C_1$-$C_6$fluoroalkyl, $C_1$-$C_6$heteroalkyl, $C_1$-$C_6$alkoxy, $C_1$-$C_6$fluoroalkoxy, $C_2$-$C_9$heterocycloalkyl, $C_6$-$C_{10}$aryl, $C_1$-$C_9$heteroaryl, $C_6$-$C_{10}$aryloxy, $C_1$-$C_6$alkylthio, $C_6$-$C_{10}$arylthio, $C_1$-$C_6$alkylsulfoxide, $C_6$-$C_{10}$arylsulfone, and $C_6$-$C_{10}$arylsulfone; J is —NHC(O)$R_7$ or —C(O)O$R_7$; and $R_7$ is unsubstituted $C_1$-$C_{12}$alkyl. In some embodiments is a compound of Formula (I), wherein Y is

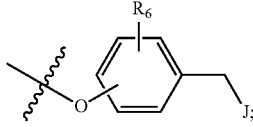

$R_6$ is $C_1$-$C_6$alkoxy; J is —NHC(O)$R_7$ or —C(O)O$R_7$; and $R_7$ is unsubstituted $C_1$-$C_{12}$alkyl. In some embodiments is a compound of Formula (I), wherein Y is

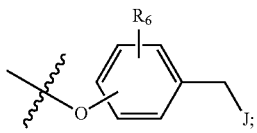

$R_6$ is $C_1$-$C_6$alkoxy; J is —NHC(O)$R_7$; and $R_7$ is unsubstituted $C_1$-$C_{12}$alkyl. In some embodiments is a compound of Formula (I), wherein Y is

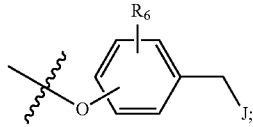

$R_6$ is $C_1$-$C_6$alkoxy; J is —C(O)O$R_7$; and $R_7$ is unsubstituted $C_1$-$C_{12}$alkyl.

In some embodiments is a compound of Formula (I), wherein Y is

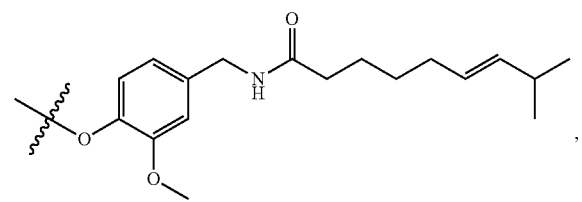

-continued
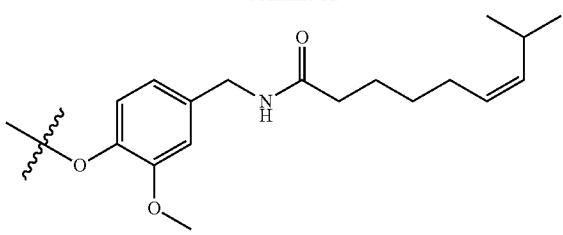
,
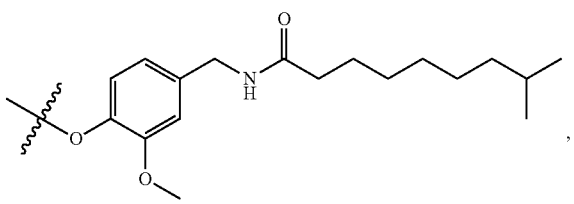
,
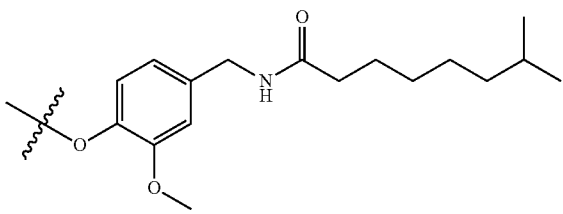
,
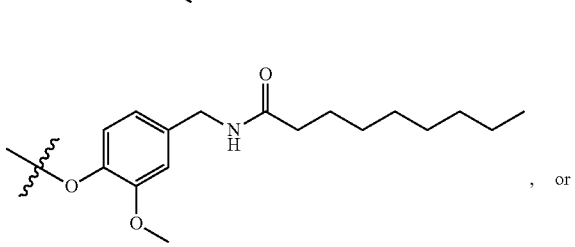
, or
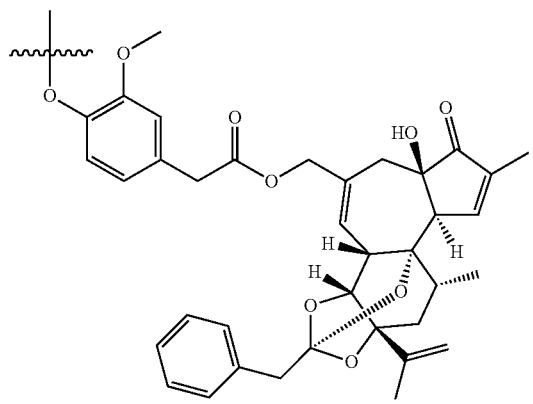
In some embodiments is a compound of Formula (I), wherein Y is
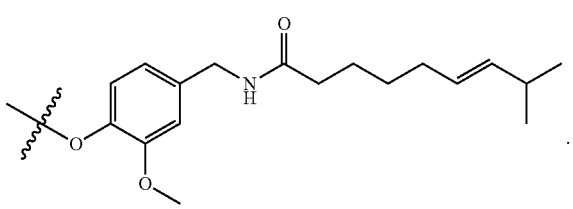 [SMILES: *Oc1ccc(CNC(=O)CCCC/C=C/C(C)C)cc1OC]
,
In some embodiments is a compound of Formula (I), wherein Y is
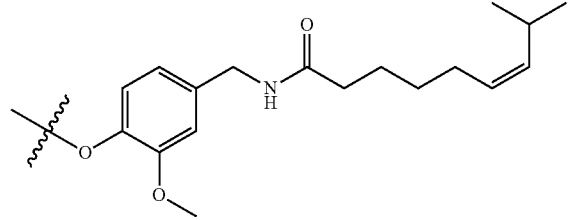
,
In some embodiments is a compound of Formula (I), wherein Y is
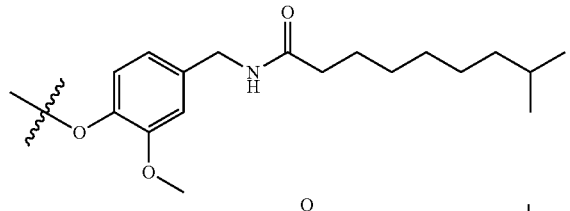
,
In some embodiments is a compound of Formula (I), wherein Y is
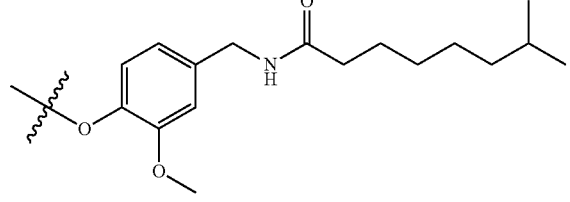
,
In some embodiments is a compound of Formula (I), wherein Y is
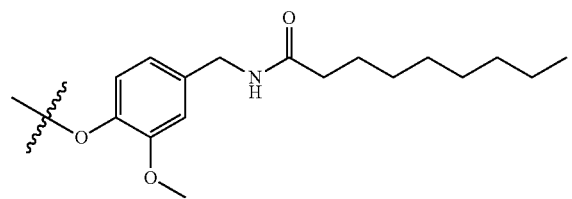
In some embodiments is a compound of Formula (I), wherein Y is
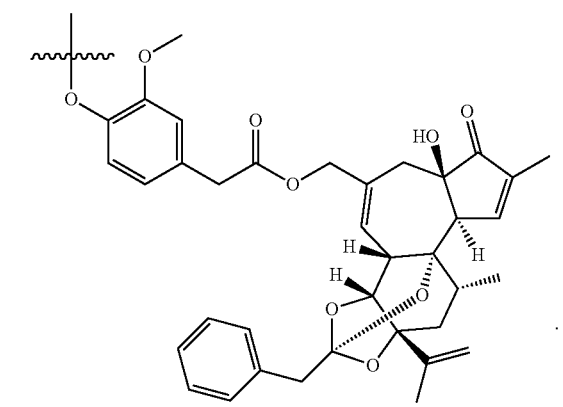 [SMILES: *Oc1ccc(CC(=O)OCC2=C[C@H]3[C@H]4O[C@@]5(Cc6ccccc6)O[C@@]3([C@H](C)C[C@]4(C(=C)C)O5)[C@@H]3C=C(C)C(=O)[C@@]3(O)C2)cc1OC]

In another embodiment, described herein is a compound having the structure of Formula (II):

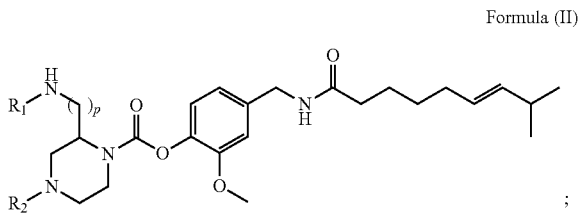

Formula (II)

wherein:
R$_1$ is hydrogen or C$_1$-C$_6$alkyl;
R$_2$ is —(CH$_2$CH$_2$O)$_n$R$_3$, —C(O)(CH$_2$)$_m$O(CH$_2$CH$_2$O)$_n$R$_3$, —C(O)O(CH$_2$CH$_2$O)$_n$R$_3$, —C(O)N(R$_4$)(CH$_2$CH$_2$O)$_n$R$_3$, —C(O)R$_5$, —C(O)OR$_5$, or —C(O)N(R$_4$)(R$_5$);
R$_3$ is hydrogen or C$_1$-C$_6$alkyl;
R$_4$ is hydrogen or C$_1$-C$_6$alkyl;
R$_5$ is C$_1$-C$_{50}$alkyl;
m is 1-10;
n is 1-50; and
p is 1-9;
or a pharmaceutically acceptable salt, pharmaceutically acceptable solvate, or hydrate thereof.

In some embodiments is a compound of Formula (II), wherein R$_2$ is —(CH$_2$CH$_2$O)$_n$R$_3$, —C(O)(CH$_2$)$_m$O(CH$_2$CH$_2$O)$_n$R$_3$, —C(O)O(CH$_2$CH$_2$O)$_n$R$_3$, or —C(O)N(R$_4$)(CH$_2$CH$_2$O)$_n$R$_3$.

In some embodiments is a compound of Formula (II), wherein R$_2$ is —(CH$_2$CH$_2$O)$_n$R$_3$. In some embodiments is a compound of Formula (II), wherein R$_2$ is —(CH$_2$CH$_2$O)$_n$R$_3$ and R$_3$ is hydrogen. In some embodiments is a compound of Formula (II), wherein R$_2$ is —(CH$_2$CH$_2$O)$_n$R$_3$ and R$_3$ is C$_1$-C$_6$alkyl. In some embodiments is a compound of Formula (II), wherein R$_2$ is —(CH$_2$CH$_2$O)$_n$R$_3$ and R$_3$ is C$_1$-C$_3$alkyl. In some embodiments is a compound of Formula (II), wherein R$_2$ is —(CH$_2$CH$_2$O)$_n$R$_3$ and R$_3$ is —CH$_3$. In some embodiments is a compound of Formula (II), wherein R$_2$ is —(CH$_2$CH$_2$O)$_n$R$_3$ and R$_3$ is —CH$_2$CH$_3$.

In some embodiments is a compound of Formula (II), wherein R$_2$ is —C(O)(CH$_2$)$_m$O(CH$_2$CH$_2$O)$_n$R$_3$. In some embodiments is a compound of Formula (II), wherein R$_2$ is —C(O)(CH$_2$)$_m$O(CH$_2$CH$_2$O)$_n$R$_3$ and R$_3$ is hydrogen. In some embodiments is a compound of Formula (II), wherein R$_2$ is —C(O)(CH$_2$)$_m$O(CH$_2$CH$_2$O)$_n$R$_3$ and R$_3$ is C$_1$-C$_6$alkyl. In some embodiments is a compound of Formula (II), wherein R$_2$ is —C(O)(CH$_2$)$_m$O(CH$_2$CH$_2$O)$_n$R$_3$ and R$_3$ is C$_1$-C$_3$alkyl. In some embodiments is a compound of Formula (II), wherein R$_2$ is —C(O)(CH$_2$)$_m$O(CH$_2$CH$_2$O)$_n$R$_3$ and R$_3$ is —CH$_3$. In some embodiments is a compound of Formula (II), wherein R$_2$ is —C(O)(CH$_2$)$_m$O(CH$_2$CH$_2$O)$_n$R$_3$ and R$_3$ is —CH$_2$CH$_3$.

In some embodiments is a compound of Formula (II), wherein R$_2$ is —C(O)O(CH$_2$CH$_2$O)$_n$R$_3$. In some embodiments is a compound of Formula (II), wherein R$_2$ is —C(O)O(CH$_2$CH$_2$O)$_n$R$_3$ and R$_3$ is hydrogen. In some embodiments is a compound of Formula (II), wherein R$_2$ is —C(O)O(CH$_2$CH$_2$O)$_n$R$_3$ and R$_3$ is C$_1$-C$_6$alkyl. In some embodiments is a compound of Formula (II), wherein R$_2$ is —C(O)O(CH$_2$CH$_2$O)$_n$R$_3$ and R$_3$ is C$_1$-C$_3$alkyl. In some embodiments is a compound of Formula (II), wherein R$_2$ is —C(O)O(CH$_2$CH$_2$O)$_n$R$_3$ and R$_3$ is —CH$_3$. In some embodiments is a compound of Formula (II), wherein R$_2$ is —C(O)O(CH$_2$CH$_2$O)$_n$R$_3$ and R$_3$ is —CH$_2$CH$_3$.

In some embodiments is a compound of Formula (II), wherein R$_2$ is —C(O)N(R$_4$)(CH$_2$CH$_2$O)$_n$R$_3$. In some embodiments is a compound of Formula (II), wherein R$_2$ is —C(O)N(R$_4$)(CH$_2$CH$_2$O)$_n$R$_3$ and R$_3$ is hydrogen. In some embodiments is a compound of Formula (II), wherein R$_2$ is —C(O)N(R$_4$)(CH$_2$CH$_2$O)$_n$R$_3$, R$_3$ is hydrogen, and R$_4$ is hydrogen. In some embodiments is a compound of Formula (II), wherein R$_2$ is —C(O)N(R$_4$)(CH$_2$CH$_2$O)$_n$R$_3$, R$_3$ is hydrogen, and R$_4$ is C$_1$-C$_6$alkyl. In some embodiments is a compound of Formula (II), wherein R$_2$ is —C(O)N(R$_4$)(CH$_2$CH$_2$O)$_n$R$_3$ and R$_3$ is C$_1$-C$_6$alkyl. In some embodiments is a compound of Formula (II), wherein R$_2$ is —C(O)N(R$_4$)(CH$_2$CH$_2$O)$_n$R$_3$, R$_3$ is C$_1$-C$_6$alkyl, and R$_4$ is hydrogen. In some embodiments is a compound of Formula (II), wherein R$_2$ is —C(O)N(R$_4$)(CH$_2$CH$_2$O)$_n$R$_3$, R$_3$ is C$_1$-C$_6$alkyl, and R$_4$ is C$_1$-C$_6$alkyl. In some embodiments is a compound of Formula (II), wherein R$_2$ is —C(O)N(R$_4$)(CH$_2$CH$_2$O)$_n$R$_3$ and R$_3$ is C$_1$-C$_3$alkyl. In some embodiments is a compound of Formula (II), wherein R$_2$ is —C(O)N(R$_4$)(CH$_2$CH$_2$O)$_n$R$_3$, R$_3$ is C$_1$-C$_3$alkyl, and R$_4$ is hydrogen. In some embodiments is a compound of Formula (II), wherein R$_2$ is —C(O)N(R$_4$)(CH$_2$CH$_2$O)$_n$R$_3$, R$_3$ is C$_1$-C$_3$alkyl, and R$_4$ is C$_1$-C$_6$alkyl. In some embodiments is a compound of Formula (II), wherein R$_2$ is —C(O)N(R$_4$)(CH$_2$CH$_2$O)$_n$R$_3$ and R$_3$ is —CH$_3$. In some embodiments is a compound of Formula (II), wherein R$_2$ is —C(O)N(R$_4$)(CH$_2$CH$_2$O)$_n$R$_3$, R$_3$ is —CH$_3$, and R$_4$ is hydrogen. In some embodiments is a compound of Formula (II), wherein R$_2$ is —C(O)N(R$_4$)(CH$_2$CH$_2$O)$_n$R$_3$, R$_3$ is —CH$_3$, and R$_4$ is C$_1$-C$_6$alkyl. In some embodiments is a compound of Formula (II), wherein R$_2$ is —C(O)N(R$_4$)(CH$_2$CH$_2$O)$_n$R$_3$ and R$_3$ is —CH$_2$CH$_3$. In some embodiments is a compound of Formula (II), wherein R$_2$ is —C(O)N(R$_4$)(CH$_2$CH$_2$O)$_n$R$_3$, R$_3$ is —CH$_2$CH$_3$, and R$_4$ is hydrogen. In some embodiments is a compound of Formula (II), wherein R$_2$ is —C(O)N(R$_4$)(CH$_2$CH$_2$O)$_n$R$_3$, R$_3$ is —CH$_2$CH$_3$, and R$_4$ is C$_1$-C$_6$alkyl.

In some embodiments is a compound of Formula (II), wherein R$_2$ is —C(O)R$_5$. In some embodiments is a compound of Formula (II), wherein R$_2$ is —C(O)R$_5$ and R$_5$ is C$_1$-C$_{45}$alkyl. In some embodiments is a compound of Formula (II), wherein R$_2$ is —C(O)R$_5$ and R$_5$ is C$_1$-C$_{40}$alkyl. In some embodiments is a compound of Formula (II), wherein R$_2$ is —C(O)R$_5$ and R$_5$ is C$_1$-C$_{35}$alkyl. In some embodiments is a compound of Formula (II), wherein R$_2$ is —C(O)R$_5$ and R$_5$ is C$_1$-C$_{30}$alkyl. In some embodiments is a compound of Formula (II), wherein R$_2$ is —C(O)R$_5$ and R$_5$ is C$_1$-C$_{25}$alkyl. In some embodiments is a compound of Formula (II), wherein R$_2$ is —C(O)R$_5$ and R$_5$ is C$_1$-C$_{20}$alkyl. In some embodiments is a compound of Formula (II), wherein R$_2$ is —C(O)R$_5$ and R$_5$ is C$_1$-C$_{15}$alkyl. In some embodiments is a compound of Formula (II), wherein R$_2$ is —C(O)R$_5$ and R$_5$ is C$_1$-C$_{10}$alkyl. In some embodiments is a compound of Formula (II), wherein R$_2$ is —C(O)R$_5$ and R$_5$ is C$_1$-C$_5$alkyl. In some embodiments is a compound of Formula (II), wherein R$_2$ is —C(O)R$_5$ and R$_5$ is —CH$_2$CH$_3$. In some embodiments is a compound of Formula (II), wherein R$_2$ is —C(O)R$_5$ and R$_5$ is —CH$_3$.

In some embodiments is a compound of Formula (II), wherein R$_2$ is —C(O)OR$_5$. In some embodiments is a compound of Formula (II), wherein R$_2$ is —C(O)OR$_5$ and R$_5$ is C$_1$-C$_{45}$alkyl. In some embodiments is a compound of Formula (II), wherein R$_2$ is —C(O)OR$_5$ and R$_5$ is C$_1$-C$_{40}$alkyl. In some embodiments is a compound of Formula (II), wherein R$_2$ is —C(O)OR$_5$ and R$_5$ is C$_1$-C$_{35}$alkyl. In some embodiments is a compound of Formula (II), wherein $R_2$ is —C(O)O$R_5$ and $R_5$ is $C_1$-$C_{30}$alkyl. In some embodiments is a compound of Formula (II), wherein $R_2$ is —C(O)O$R_5$ and $R_5$ is $C_1$-$C_{25}$alkyl. In some embodiments is a compound of Formula (II), wherein $R_2$ is —C(O)O$R_5$ and $R_5$ is $C_1$-$C_{20}$alkyl. In some embodiments is a compound of Formula (II), wherein $R_2$ is —C(O)O$R_5$ and $R_5$ is $C_1$-$C_{15}$alkyl. In some embodiments is a compound of Formula (II), wherein $R_2$ is —C(O)O$R_5$ and $R_5$ is $C_1$-$C_{10}$alkyl. In some embodiments is a compound of Formula (II), wherein $R_2$ is —C(O)O$R_5$ and $R_5$ is $C_1$-$C_5$alkyl. In some embodiments is a compound of Formula (II), wherein $R_2$ is —C(O)O$R_5$ and $R_5$ is —CH$_2$CH$_3$. In some embodiments is a compound of Formula (II), wherein $R_2$ is —C(O)O$R_5$ and $R_5$ is —CH$_3$.

In some embodiments is a compound of Formula (II), wherein $R_2$ is —C(O)N($R_4$)($R_5$). In some embodiments is a compound of Formula (II), wherein $R_2$ is —C(O)N($R_4$)($R_5$), $R_4$ is H, and $R_5$ is $C_1$-$C_{45}$alkyl. In some embodiments is a compound of Formula (II), wherein $R_2$ is —C(O)N($R_4$)($R_5$), $R_4$ is H, and $R_5$ is $C_1$-$C_{40}$alkyl. In some embodiments is a compound of Formula (II), wherein $R_2$ is —C(O)N($R_4$)($R_5$), $R_4$ is H, and $R_5$ is $C_1$-$C_{35}$alkyl. In some embodiments is a compound of Formula (II), wherein $R_2$ is —C(O)N($R_4$)($R_5$), $R_4$ is H, and $R_5$ is $C_1$-$C_{30}$alkyl. In some embodiments is a compound of Formula (II), wherein $R_2$ is-C(O)N($R_4$)($R_5$), $R_4$ is H, and $R_5$ is $C_1$-$C_{25}$alkyl. In some embodiments is a compound of Formula (II), wherein $R_2$ is —C(O)N($R_4$)($R_5$), $R_4$ is H, and $R_5$ is $C_1$-$C_{20}$alkyl. In some embodiments is a compound of Formula (II), wherein $R_2$ is —C(O)N($R_4$)($R_5$), $R_4$ is H, and $R_5$ is $C_1$-$C_{15}$alkyl. In some embodiments is a compound of Formula (II), wherein $R_2$ is —C(O)N($R_4$)($R_5$), $R_4$ is H, and $R_5$ is $C_1$-$C_{10}$alkyl. In some embodiments is a compound of Formula (II), wherein $R_2$ is —C(O)N($R_4$)($R_5$), $R_4$ is H, and $R_5$ is $C_1$-$C_5$alkyl. In some embodiments is a compound of Formula (II), wherein $R_2$ is —C(O)N($R_4$)($R_5$), $R_4$ is H, and $R_5$ is —CH$_2$CH$_3$. In some embodiments is a compound of Formula (II), wherein $R_2$ is —C(O)N($R_4$)($R_5$), $R_4$ is H, and $R_5$ is —CH$_3$.

In some embodiments is a compound of Formula (II), wherein $R_2$ is —C(O)N($R_4$)($R_5$), $R_4$ is $C_1$-$C_6$alkyl, and $R_5$ is $C_1$-$C_{45}$alkyl. In some embodiments is a compound of Formula (II), wherein $R_2$ is —C(O)N($R_4$)($R_5$), $R_4$ is $C_1$-$C_6$alkyl, and $R_5$ is $C_1$-$C_{40}$alkyl. In some embodiments is a compound of Formula (II), wherein $R_2$ is —C(O)N($R_4$)($R_5$), $R_4$ is $C_1$-$C_6$alkyl, and $R_5$ is $C_1$-$C_{35}$alkyl. In some embodiments is a compound of Formula (II), wherein $R_2$ is —C(O)N($R_4$)($R_5$), $R_4$ is $C_1$-$C_6$alkyl, and $R_5$ is $C_1$-$C_{30}$alkyl. In some embodiments is a compound of Formula (II), wherein $R_2$ is-C(O)N($R_4$)($R_5$), $R_4$ is $C_1$-$C_6$alkyl, and $R_5$ is $C_1$-$C_{25}$alkyl. In some embodiments is a compound of Formula (II), wherein $R_2$ is —C(O)N($R_4$)($R_5$), $R_4$ is $C_1$-$C_6$alkyl, and $R_5$ is $C_1$-$C_{20}$alkyl. In some embodiments is a compound of Formula (II), wherein $R_2$ is —C(O)N($R_4$)($R_5$), $R_4$ is $C_1$-$C_6$alkyl, and $R_5$ is $C_1$-$C_{15}$alkyl. In some embodiments is a compound of Formula (II), wherein $R_2$ is —C(O)N($R_4$)($R_5$), $R_4$ is $C_1$-$C_6$alkyl, and $R_5$ is $C_1$-$C_{10}$alkyl. In some embodiments is a compound of Formula (II), wherein $R_2$ is —C(O)N($R_4$)($R_5$), $R_4$ is $C_1$-$C_6$alkyl, and $R_5$ is $C_1$-$C_5$alkyl. In some embodiments is a compound of Formula (II), wherein $R_2$ is —C(O)N($R_4$)($R_5$), $R_4$ is $C_1$-$C_6$alkyl, and $R_5$ is —CH$_2$CH$_3$. In some embodiments is a compound of Formula (II), wherein $R_2$ is —C(O)N($R_4$)($R_5$), $R_4$ is $C_1$-$C_6$alkyl, and $R_5$ is —CH$_3$. In some embodiments is a compound of Formula (II), wherein $R_2$ is —C(O)N($R_4$)($R_5$), $R_4$ is —CH$_3$, and $R_5$ is —CH$_2$CH$_3$. In some embodiments is a compound of Formula (II), wherein $R_2$ is —C(O)N($R_4$)($R_5$), $R_4$ is —CH$_3$, and $R_5$ is —CH$_3$.

In some embodiments is a compound of Formula (II), wherein m is 1-5. In some embodiments is a compound of Formula (II), wherein m is 2-10. In some embodiments is a compound of Formula (II), wherein m is 4-10. In some embodiments is a compound of Formula (II), wherein m is 2-8. In some embodiments is a compound of Formula (II), wherein m is 2-6. In some embodiments is a compound of Formula (II), wherein m is 2-4. In some embodiments is a compound of Formula (II), wherein m is 1. In some embodiments is a compound of Formula (II), wherein m is 2. In some embodiments is a compound of Formula (II), wherein m is 3. In some embodiments is a compound of Formula (II), wherein m is 4. In some embodiments is a compound of Formula (II), wherein m is 5. In some embodiments is a compound of Formula (II), wherein m is 6. In some embodiments is a compound of Formula (II), wherein m is 7. In some embodiments is a compound of Formula (II), wherein m is 8. In some embodiments is a compound of Formula (II), wherein m is 9. In some embodiments is a compound of Formula (II), wherein m is 10.

In some embodiments is a compound of Formula (II), wherein n is 1-45. In some embodiments is a compound of Formula (II), wherein n is 1-40. In some embodiments is a compound of Formula (II), wherein n is 1-35. In some embodiments is a compound of Formula (II), wherein n is 1-30. In some embodiments is a compound of Formula (II), wherein n is 1-25. In some embodiments is a compound of Formula (II), wherein n is 1-20. In some embodiments is a compound of Formula (II), wherein n is 2-20. In some embodiments is a compound of Formula (II), wherein n is 2-16. In some embodiments is a compound of Formula (II), wherein n is 2-12. In some embodiments is a compound of Formula (II), wherein n is 2-10. In some embodiments is a compound of Formula (II), wherein n is 4-10. In some embodiments is a compound of Formula (II), wherein n is 1. In some embodiments is a compound of Formula (II), wherein n is 2. In some embodiments is a compound of Formula (II), wherein n is 3. In some embodiments is a compound of Formula (II), wherein n is 4. In some embodiments is a compound of Formula (II), wherein n is 5. In some embodiments is a compound of Formula (II), wherein n is 6. In some embodiments is a compound of Formula (II), wherein n is 7. In some embodiments is a compound of Formula (II), wherein n is 8. In some embodiments is a compound of Formula (II), wherein p is 9. In some embodiments is a compound of Formula (II), wherein n is 10. In some embodiments is a compound of Formula (II), wherein n is 11. In some embodiments is a compound of Formula (II), wherein p is 12. In some embodiments is a compound of Formula (II), wherein n is 13. In some embodiments is a compound of Formula (II), wherein n is 14. In some embodiments is a compound of Formula (II), wherein p is 15. In some embodiments is a compound of Formula (II), wherein n is 16.

In some embodiments is a compound of Formula (II), wherein p is 1. In some embodiments is a compound of Formula (II), wherein p is 2. In some embodiments is a compound of Formula (II), wherein p is 3. In some embodiments is a compound of Formula (II), wherein p is 4. In some embodiments is a compound of Formula (II), wherein p is 5. In some embodiments is a compound of Formula (II), wherein p is 6. In some embodiments is a compound of Formula (II), wherein p is 7. In some embodiments is a compound of Formula (II), wherein p is 8. In some embodiments is a compound of Formula (II), wherein p is 9.

In some embodiments is a compound of Formula (II), wherein $R_1$ is hydrogen. In some embodiments is a compound of Formula (II), wherein $R_1$ is $C_1$-$C_6$alkyl. In some embodiments is a compound of Formula (II), wherein $R_1$ is $C_1$-$C_3$alkyl. In some embodiments is a compound of Formula (II), wherein $R_1$ is —$CH_3$. In some embodiments is a compound of Formula (II), wherein $R_1$ is —$CH_2CH_3$.

In some embodiments is a compound of Formula (II), wherein p is 1 and $R_1$ is hydrogen. In some embodiments is a compound of Formula (II), wherein p is 1 and $R_1$ is $C_1$-$C_6$alkyl. In some embodiments is a compound of Formula (II), wherein p is 1 and $R_1$ is $C_1$-$C_3$alkyl. In some embodiments is a compound of Formula (II), wherein p is 1 and $R_1$ is —$CH_3$. In some embodiments is a compound of Formula (II), wherein p is 1 and $R_1$ is —$CH_2CH_3$. In some embodiments is a compound of Formula (II), wherein p is 2 and $R_1$ is hydrogen. In some embodiments is a compound of Formula (II), wherein p is 2 and $R_1$ is $C_1$-$C_6$alkyl. In some embodiments is a compound of Formula (II), wherein p is 2 and $R_1$ is $C_1$-$C_3$alkyl. In some embodiments is a compound of Formula (II), wherein p is 2 and $R_1$ is —$CH_3$. In some embodiments is a compound of Formula (II), wherein p is 2 and $R_1$ is —$CH_2CH_3$.

In another embodiment is a compound selected from:

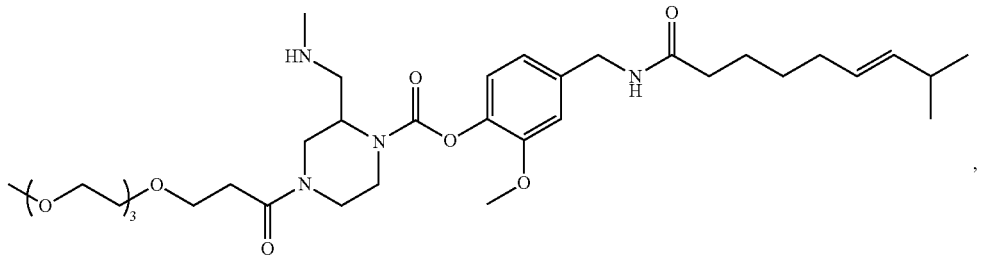
,

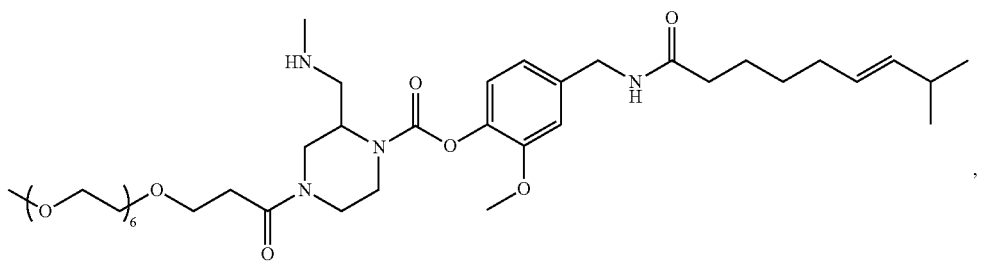
,

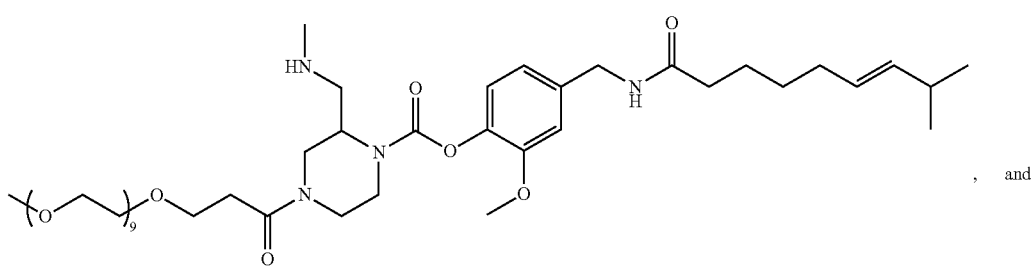
, and

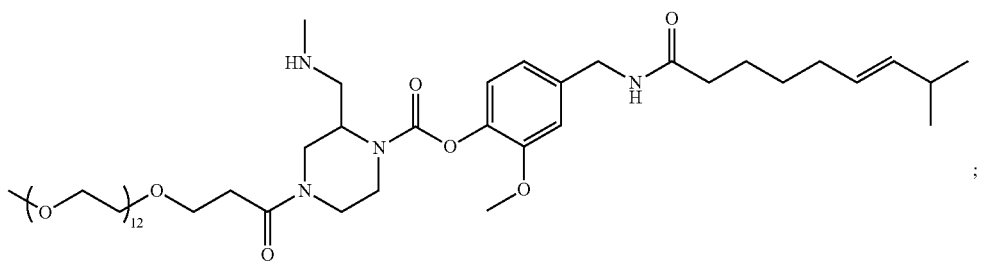
;

or a pharmaceutically acceptable salt, pharmaceutically acceptable solvate, or hydrate thereof.

In another embodiment is a compound selected from:

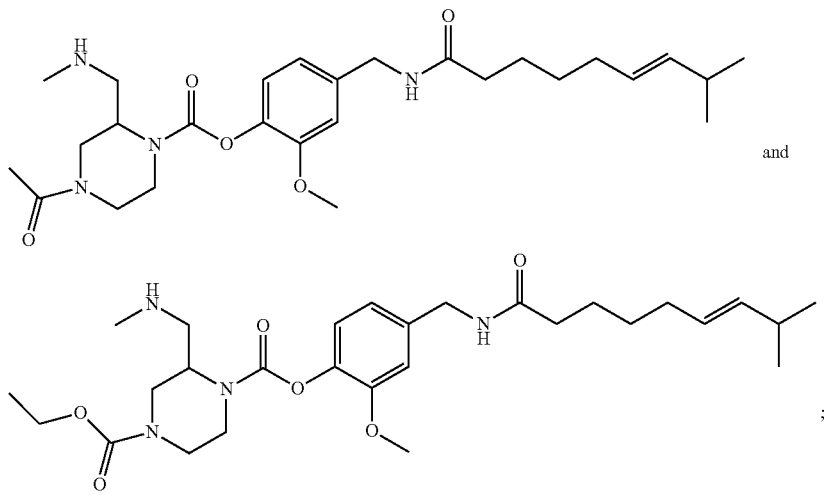

or a pharmaceutically acceptable salt, pharmaceutically acceptable solvate, or hydrate thereof.

Synthesis of Compounds

In some embodiments, the synthesis of compounds described herein is accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich Corp., Fisher Scientific (Fisher Chemicals), and Acros Organics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein.

Further Forms of Compounds

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by the forming diastereomeric and separation by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In some situations, compounds may exist as tautomers. All tautomers are included within the formulas described herein.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

The compounds of Formula (I) or (II), or pharmaceutically acceptable salt, pharmaceutically acceptable solvate, or hydrate thereof, described herein are prodrugs of TRPV1 agonists. A "prodrug" refers to an agent that is converted into the parent drug in vivo. The compounds of Formula (I) or (II), or pharmaceutically acceptable salt, pharmaceutically acceptable solvate, or hydrate thereof, described herein are directed to novel water-soluble prodrugs of TRPV1 agonists and their methods of synthesis and use. In addition to specifically identified compounds, these derivatives are capable of chemical reverting to the active parent compound when exposed to physiological conditions. These derivatives have significantly higher hydrophilicity/water solubility than their parent drugs and are hence better able to be incorporated into commonly used aqueous formulations. Further described herein is a method of increasing the water solubility of capsaicin, its analogs and other TRPV1 agonists, by modifying the prodrug's chemical structure with hydrophilic moieties. In embodiments described herein, the introduction of basic moieties capable of being protonated under acidic conditions increases the solubility of a TRPV1 agonist prodrug. The prodrugs described herein are designed such that the parent drug is released under well-defined rates after its structural derivative has been delivered to the body and/or is exposed to specific physiological conditions.

The compounds described herein may be labeled isotopically (e.g. with a radioisotope) or by other means, including, but not limited to, the use of chromophores or fluorescent moieties, bioluminescent labels, photoactivatable or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, 2H, 3H, 13C, 14C, 15N, 18O, 17O, 35S, 18F, 36Cl, respectively. Certain isotopically-labeled compounds described herein, for example those into which radioactive isotopes such as 3H and 14C are incorporated, are useful in drug and/or substrate tissue distribution assays. Further, substitution with isotopes such as deuterium, i.e., 2H, can afford certain therapeutic advantages resulting from greater metabolic stability, such as, for example, increased in vivo half-life or reduced dosage requirements.

Compounds described herein may be formed as, and/or used as, pharmaceutically acceptable salts. The type of pharmaceutical acceptable salts, include, but are not limited to acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like. In other cases, compounds described herein may form salts with amino acids such as, but not limited to, arginine, lysine, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

In some embodiments, compounds described herein, such as compounds of Formula (I) or (II), are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravimetric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Use of Protecting Groups (PG)

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a $Pd^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

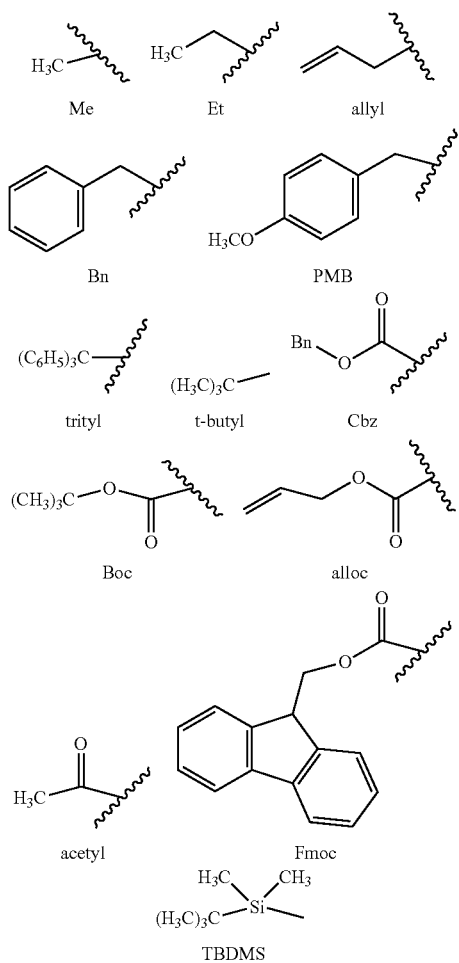

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Diseases, Disorders or Conditions

In another aspect is a method of treating pain in a subject, comprising administering to the subject a therapeutically effective amount of a compound of Formula (I) or (II), or a pharmaceutically acceptable salt, pharmaceutically acceptable solvate, or hydrate thereof. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with post-operative pain. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with chronic post-surgical pain. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with neuropathic pain. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with postherpetic neuralgia. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with diabetic neuropathy. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with HIV-associated neuropathy. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with complex regional pain syndrome. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with cancer. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with cancer chemotherapy. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with nerve injury. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with vulvodynia. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with trauma. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with surgery. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with chronic musculoskeletal pain. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with lower back pain. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with osteoarthritis or rheumatoid arthritis. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with osteoarthritis arthritis. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with rheumatoid arthritis. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with bursitis, tendonitis, epicondylitis. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with Carpal tunnel syndrome. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with Morton's neuroma. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with Compartment syndrome. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with spinal cord injury. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with post-amputation. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with phantom limb pain. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with terminal cancer pain. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with peripheral neuropathy. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with visceral pain. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with interstitial cystitis. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with overactive bladder. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with radiculopathy. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the pain is associated with rib and long bone fracture.

In some embodiments is a method of treating psoriasis, pruritus, itch, or cancer in a subject, comprising administering to the subject a therapeutically effective amount of a compound of Formula (I) or (II), or a pharmaceutically acceptable salt, pharmaceutically acceptable solvate, or hydrate thereof. In some embodiments is a method of treating psoriasis in a subject, comprising administering to the subject a therapeutically effective amount of a compound of Formula (I) or (II), or a pharmaceutically acceptable salt, pharmaceutically acceptable solvate, or hydrate thereof. In some embodiments is a method of treating pruritus in a subject, comprising administering to the subject a therapeutically effective amount of a compound of Formula (I) or (II), or a pharmaceutically acceptable salt, pharmaceutically acceptable solvate, or hydrate thereof. In some embodiments is a method of treating itch in a subject, comprising administering to the subject a therapeutically effective amount of a compound of Formula (I) or (II), or a pharmaceutically acceptable salt, pharmaceutically acceptable solvate, or hydrate thereof. In some embodiments is a method of treating cancer in a subject, comprising administering to the subject a therapeutically effective amount of a compound of Formula (I) or (II), or a pharmaceutically acceptable salt, pharmaceutically acceptable solvate, or hydrate thereof.

In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the compound is administered locally. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the compound is administered dermally. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the compound is administered transdermally. In some embodiments is a method of treating pain in a subject, comprising administering to the subject a therapeutically effective amount of a compound of Formula (I) or (II), or a pharmaceutically acceptable salt, pharmaceutically acceptable solvate, or hydrate thereof, wherein the compound is administered systemically.

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, C1-Cx includes C1-C2, C1-C3 . . . C1-Cx. C1-Cx refers to the number of carbon atoms that make up the moiety to which it designates (excluding optional substituents).

An "alkyl" group refers to an aliphatic hydrocarbon group, wherein an sp3-hybridized carbon of the alkyl residue is attached to the rest of the molecule by a single bond. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl.

Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)=CR2, wherein R refers to the remaining portions of the alkenyl group, which may be the same or different. Non-limiting examples of an alkenyl group include —CH=CH2, —C(CH3)=CH2, —CH=CHCH3, —CH=C(CH3)2 and —C(CH3)=CHCH3. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH₃, —C≡CCH₂CH₃ and —≡CCCH₂CH₂CH₃. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH2 group.

The term "alkylamine" or "alkylamino" refers to the —N(alkyl)xHy group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)₂ group, where alkyl is as defined herein.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

As used herein, the term "acyl" refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, heterocycloalkyl, heteroaryl group or the like.

"Carboxy" refers to —CO₂H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

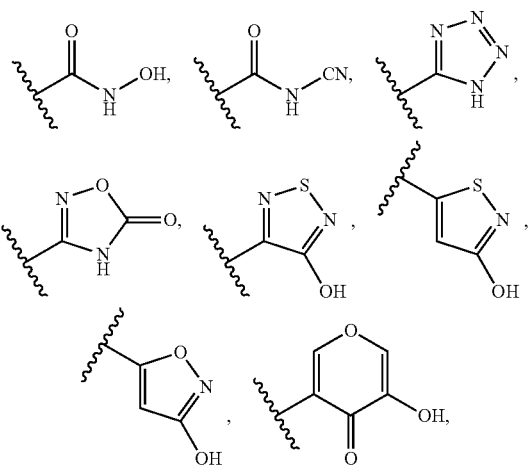

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

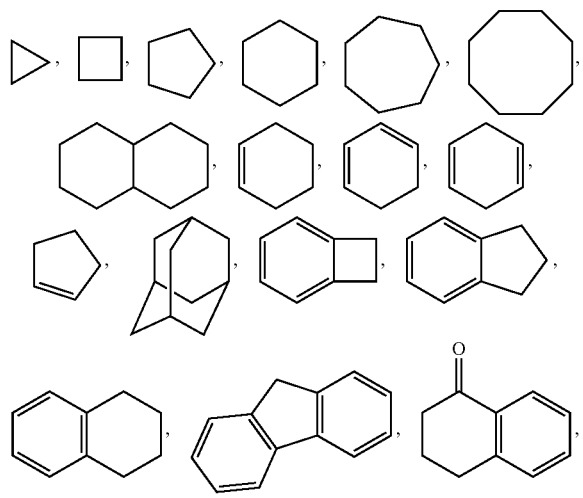

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

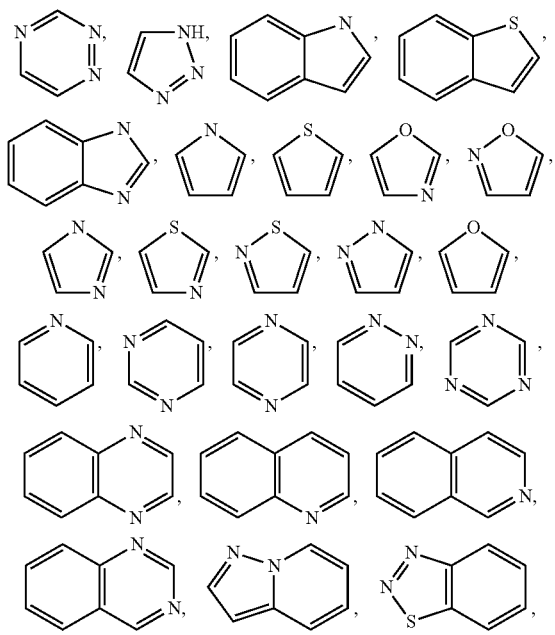

and the like.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. Illustrative examples of heterocycloalkyl groups, also referred to as non-aromatic heterocycles, include:

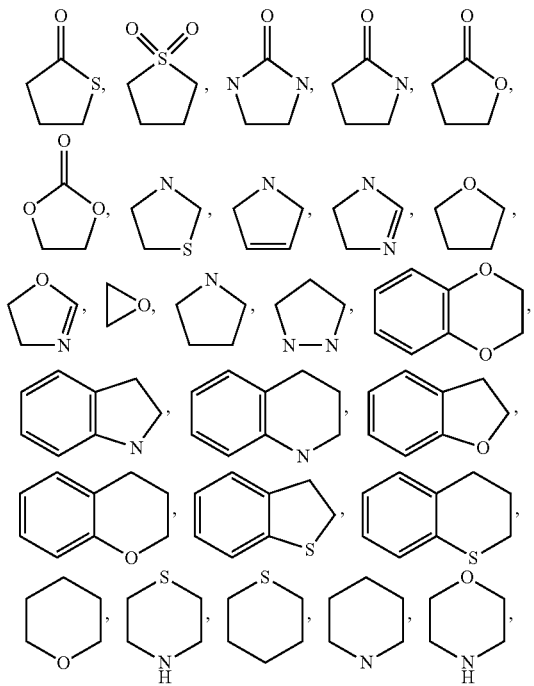

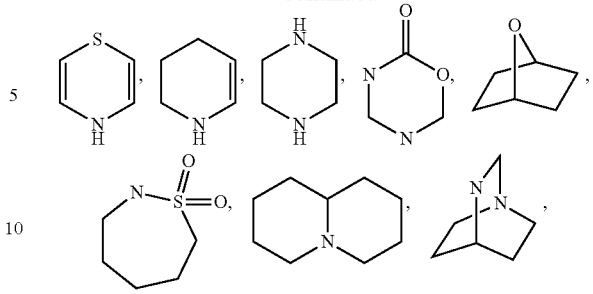

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" or "haloalkoxy" refers to an alkyl group or alkoxy group that is substituted with one or more halogens. The halogens may the same or they may be different. Non-limiting examples of haloalkyls include —CH$_2$Cl, —CF$_3$, —CHF$_2$, —CH$_2$CF$_3$, —CF$_2$CF$_3$, —CF(CH$_3$)$_2$, and the like. Non-limiting examples of haloalkoxys include —OCH$_2$Cl, —OCF$_3$, —OCHF$_2$, —OCH$_2$CF$_3$, —OCF$_2$CF$_3$, —OCF(CH$_3$)$_2$, and the like.

The terms "fluoroalkyl" and "fluoroalkoxy" include alkyl and alkoxy groups, respectively, that are substituted with one or more fluorine atoms. Non-limiting examples of fluoroalkyls include —CF$_3$, —CHF$_2$, —CH$_2$F, —CH$_2$CF$_3$, —CF$_2$CF$_3$, —CF$_2$CF$_2$CF$_3$, —CF(CH$_3$)$_3$, and the like. Non-limiting examples of fluoroalkoxy groups, include —OCF$_3$, —OCHF$_2$, —OCH$_2$F, —OCH$_2$CF$_3$, —OCF$_2$CF$_3$, —OCF$_2$CF$_2$CF$_3$, —OCF(CH$_3$)$_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH$_2$—NH—OCH$_3$, —CH$_2$—O—Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2$H, —$CO_2$-alkyl, nitro, haloalkyl, fluoroalkyl, fluoroalkoxy, and amino, including mono- and di-substituted amino groups (e.g. —$NH_2$, —NHR, —$N(R)_2$), and the protected derivatives thereof. In some embodiments, optional substituents are independently selected from halogen, —CN, —$NH_2$, —$NH(CH_3)$, —$N(CH_3)_2$, —OH, —$CO_2$H, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —$NH_2$, —OH, —$NH(CH_3)$, —$N(CH_3)_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

"Counterion" refers to an ion that accompanies an ionic species in order to maintain electric neutrality. Examples of counterions include, but are not limited to, $Cl^-$, $Br^-$, $I^-$, and $CF_3CO_2^-$.

The methods and formulations described herein include the use of crystalline forms (also known as polymorphs), or pharmaceutically acceptable salts of compounds having the structure of Formula (I) or (II), as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target. For example, a modulator can cause an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

The term "acceptable" with respect to a formulation, composition or ingredient, as used herein, means having no persistent detrimental effect on the general health of the subject being treated.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that one active ingredient, e.g. a compound of Formula (I) or (II), and a co-agent, are both administered to a patient simultaneously in the form of a single entity or dosage. The term "non-fixed combination" means that one active ingredient, e.g. a compound of Formula (I) or (II), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound of Formula (I) or (II) described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "capsaicinoid or capsaicin analog" is meant to include any compound that produces a selective, highly-localized destruction or incapacitation of C-fiber and/or A-delta-fiber in discrete localized areas responsible for the initiation of pain for the purpose of eliminating pain arising from that locus, while minimizing potential adverse consequences of C-fiber and/or A-delta-fiber activation and/or damage outside of the locus of pain such as (E)-capsaicin, resiniferatoxin, AM-404 (N-(4-Hydroxyphenyl)-5Z,8Z,11Z, 14Z-eicosatetraenamide), Anandamide, Arvanil, 6′-Iodoresiniferatoxin, NADA (N-arachidonyldopamine), OLDA (N-oleoyldopamine), olvanil, and PPAHV (phorbol 12-phenylacetate 13-acetate 20-homovanillate). Other suitable capsaicinoids for use described herein include, but are not limited to, N-vanillylnonanamides, N-vanillylsulfonamides, N-vanillylureas, N-vanillylcarbamates, N-[(substituted phenyl)methyl]alkylamides, methylene substituted N-[(substituted phenyl)methyl]alkanamides, N-[(substituted phenyl)methyl]-cis-monosaturated alkenamides, N-[(substituted phenyl)methyl]di-unsaturated amides, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civainde, nonivamide, N-oleylhomovanillamidia, isovelleral, scalaradial, ancistrodial, β-acaridial, merulidial, scutigeral and any combinations or mixtures thereof.

The term "TRPV1 agonist", as used herein, refers to a compound or composition that activates the transient receptor potential vanilloid 1 receptor (TRPV1). TRPV1 agonists include, but are not limited to, capsaicin, dihydrocapsaicin, nordihydrocapsaicin, homodihydrocapsaicin, homocapsaicin, dihydrocapsaicin, nonivamide, and resiniferatoxin.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition that includes a compound of Formula (I) or (II) described herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "co-administration" or the like, as used herein, are meant to encompass administration of the selected therapeutic agents to a single patient, and are intended to include treatment regimens in which the agents are administered by the same or different route of administration or at the same or different time.

The term "carrier," as used herein, refers to relatively nontoxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds.

"Bioavailability" refers to the percentage of the weight of the compound disclosed herein (e.g. compound of Formula (I) or (II)), that is delivered into the general circulation of the animal or human being studied. The total exposure))(AUC (0-∞)) of a drug when administered intravenously is usually defined as 100% bioavailable (F %). "Oral bioavailability" refers to the extent to which a compound disclosed herein, is absorbed into the general circulation when the pharmaceutical composition is taken orally as compared to intravenous injection.

"Blood plasma concentration" refers to the concentration of a compound of Formula (I) or (II) disclosed herein, in the plasma component of blood of a subject. It is understood that the plasma concentration of compounds described herein may vary significantly between subjects, due to variability with respect to metabolism and/or possible interactions with other therapeutic agents. In accordance with one embodiment disclosed herein, the blood plasma concentration of the compounds disclosed herein may vary from subject to subject. Likewise, values such as maximum plasma concentration (Cmax) or time to reach maximum plasma concentration (Tmax), or total area under the plasma concentration time curve (AUC(0-∞)) may vary from subject to subject. Due to this variability, the amount necessary to constitute "a therapeutically effective amount" of a compound may vary from subject to subject.

As used herein, "amelioration" refers to an improvement in a disease or condition or at least a partial relief of symptoms associated with a disease or condition.

Pharmaceutical Compositions and Methods of Administration

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999), herein incorporated by reference for such disclosure.

A pharmaceutical composition, as used herein, refers to a mixture of a compound of Formula (I) or (II) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a subject having a disease, disorder, or condition to be treated. In some embodiments, the subject is a human. A therapeutically effective amount can vary widely depending on the severity of the disease, the age and relative health of the subject, the potency of the compound used and other factors. The compounds of Formula (I) or (II) can be used singly or in combination with one or more therapeutic agents as components of mixtures (as in combination therapy).

The pharmaceutical formulations described herein can be administered to a subject by multiple administration routes, including but not limited to, oral, parenteral (e.g., epidural, intravenous, subcutaneous, intramuscular), intranasal, buccal, topical, rectal, or transdermal administration routes. Moreover, the pharmaceutical compositions described herein, which include a compound of Formula (I) or (II) described herein, can be formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

One may administer the compounds and/or compositions in a local rather than systemic manner, for example, via injection of the compound directly into an organ or tissue, often in a depot preparation. Such formulations may be administered by implantation (for example subcutaneously or intramuscularly) or by intramuscular injection. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I) or (II) described herein, as an active ingredient in free-acid or free-base form, or in a pharmaceutically acceptable salt form. In addition, the methods and pharmaceutical compositions described herein include the use of crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Pharmaceutical preparations for oral use can be obtained by mixing one or more solid excipient with one or more of the compounds described herein (e.g. compounds of Formula (I) or (II)), optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of Formula (I) or (II) described herein, with one or more pharmaceutical excipients to form a bulk blend composition. When referring to these bulk blend compositions as homogeneous, it is meant that the particles of the compound of Formula (I) or (II) described herein, are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

The pharmaceutical solid dosage forms described herein can include a compound of Formula (I) or (II) described herein, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of Formula (I) or (II) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compounds of Formula (I) or (II) described herein from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of Formula (I) or (II) described herein and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds described herein, which sufficiently isolate the compound from other non-compatible excipients. Materials compatible with compounds described herein are those that delay the release of the compounds of Formula (I) or (II) in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit L30D-55, Eudragit® FS 30D Eudragit® L100-55, Eudragit® L100, Eudragit® 5100, Eudragit® RD100, Eudragit® E100, Eudragit® L12.5, Eudragit® 512.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds described herein may be formulated by methods that include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound described herein, are solid dispersions. Methods of producing such solid dispersions include, but are not limited to, for example, U.S. Pat. Nos. 4,343,789, 5,340,591, 5,456,923, 5,700,485, 5,723,269, and U.S. patent publication no. 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions include, but are not limited to, for example, U.S. Pat. Nos. 4,151,273, 5,281,420, and 6,083,518.

The pharmaceutical solid oral dosage forms including formulations described herein, which include a compounds described herein, can be further formulated to provide a controlled release of the compound of Formula (I) or (II). Controlled release refers to the release of the compounds described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "rapid release" or "delayed release" as used herein refers to the delivery so that the release can be accomplished at some generally predictable rate. In some embodiments the method for delay of release is either the tuning of the intramolecular cyclization-release reaction or via the addition of buffers to modify the initiation of the intramolecular cyclization-release reaction.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include a compound of Formula (I) or (II) described herein, are delivered using a pulsatile dosage form. A pulsatile dosage form is capable of providing one or more immediate release pulses at predetermined time points after a controlled lag time or at specific sites. Pulsatile dosage forms may be administered using a variety of pulsatile formulations including, but are not limited to, those described in U.S. Pat. Nos. 5,011,692; 5,017,381; 5,229,135; 5,840,329; 4,871,549; 5,260,068; 5,260,069; 5,508,040; 5,567,441 and 5,837,284.

Many other types of controlled release systems are suitable for use with the formulations described herein. Examples of such delivery systems include, e.g., polymer-based systems, such as polylactic and polyglycolic acid, polyanhydrides and polycaprolactone; porous matrices, non-polymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983.

In some embodiments, pharmaceutical formulations are provided that include particles of the compounds described herein, e.g. compounds of Formula (I) or (II), and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960,563.

There is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein.

Potential excipients for intranasal formulations include, for example, U.S. Pat. Nos. 4,476,116, 5,116,817 and 6,391,452. Formulations solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include compounds described herein may be administered using a variety of formulations which include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound is provided essentially throughout. Buccal drug delivery avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, virtually any such carrier can be used, so long as the desired drug release profile is not compromised, and the carrier is compatible with the compounds described herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal formulations described herein may be administered using a variety of devices including but not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound of Formula (I) or (II); (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or nonaqueous solutions, preferably with physiologically compatible buffers or excipients. Such excipients are generally recognized in the field.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and are formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Generally, an agent, such as a compound of Formula (I) or (II) is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

The particular delivery system used can depend on a number of factors, including, for example, the intended target and the route of administration, e.g., local or systemic. Targets for delivery can be specific cells which are causing or contributing to a disease or disorder. For example, a target cell can be resident or infiltrating cells in the nervous system contributing to a neurological, neurodegenerative or demyelinating disease or disorder. Administration of an agent can be directed to one or more cell types or subsets of a cell type by methods recognized in the field. For example, an agent can be coupled to an antibody, ligand to a cell surface receptor or a toxin, or can be contained in a particle that is selectively internalized into cells, e.g., liposomes or a virus in which the viral receptor binds specifically to a certain cell type, or a viral particle lacking the viral nucleic acid, or can be administered locally.

Methods of Dosing and Treatment Regimens

The compounds described herein can be used in the preparation of medicaments for the modulation of TRPV1, or for the treatment of diseases or conditions that would benefit, at least in part, from modulation of TRPV1. In addition, a method for treating any of the diseases or conditions described herein in a subject in need of such treatment, involves administration of pharmaceutical compositions containing at least one compound described herein, or a pharmaceutically acceptable salt, or pharmaceutically acceptable solvate or hydrate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

Upon the doctor's discretion the administration of the compounds may be administered chronically, that is, for an extended period of time, including throughout the duration of the patient's life in order to ameliorate or otherwise control or limit the symptoms of the patient's disease or condition.

Upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.001 mg per day to about 5000 mg per day, in some embodiments, about 1 mg per day to about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to, ampoules, or in multi-dose containers, with an added preservative.

The daily dosages appropriate for the compounds described herein described herein are from about 0.001 mg/kg to about 30 mg/kg. In one embodiment, the daily dosages are from about 0.01 mg/kg to about 10 mg/kg. An indicated daily dosage in the larger mammal, including, but not limited to, humans, is in the range from about 0.1 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The compounds of Formula (I) or (II), and compositions thereof, may also be used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as a compound of Formula (I) or (II), is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

In certain instances, the combination with another therapeutic agent is with a local anesthetic agent. As used herein, the term "local anesthetic" means a drug which provides local numbness or pain relief. Exemplary examples of local anesthetic agents which can be used in combination with the present invention include: bupivacaine, levobupivaine, ropivacaine, dibucaine, procaine, chloroprocaine, priolocaine, mepivacaine, etidocaine, tetracaine and lidocaine.

In certain instances, the combination with another therapeutic agent is with a vasoconstrictor. Vasoconstrictors are useful are those acting locally to restrict blood flow, and thereby retain the injected drugs in the region in which they are administered. This has the effect of substantially decreasing systemic toxicity. Preferred vasoconstrictors are those acting on alpha adrenergic receptors, such as epinephrine and phenylepinephrine.

In certain instances, the combination with another therapeutic agent is with a glucocorticoid. The glucocorticoid is selected from the group consisting of dexamethasone, cortisone, hydrocortisone, prednisone, beclomethasone, betamethasone, flunisolide, methyl prednisone, para methasone, prednisolone, triamcinolome, alclometasone, amcinonide, clobetasol, fludrocortisone, diflurosone diacetate, fluocinolone acetonide, fluoromethalone, flurandrenolide, halcinonide, medrysone, mometasone, and pharmaceutically acceptable salts and mixtures thereof.

In some embodiments, a compound of Formula (I) or (II), or a pharmaceutically acceptable salt, pharmaceutically acceptable solvate, or hydrate thereof, is used in combination with a local anesthetic.

In some embodiments, a compound of Formula (I) or (II), or a pharmaceutically acceptable salt, pharmaceutically acceptable solvate, or hydrate thereof, is used in combination with a non-opioid analgesic.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I) or (II) described herein) may be administered in any order or even simultaneously. If simultaneously, the multiple therapeutic agents may be provided in a single, unified form, or in multiple forms (by way of example only, either as a single injection or as two separate injections). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

limited to, Sigma-Aldrich Corp., Acros Organics, Fluka, Fisher Scientific, Arkpharm, Enamine Store, and Oakwood Chemicals.

EXAMPLES

These examples are provided for illustrative purposes only and not to limit the scope of the claims provided herein. The starting materials and reagents used for the synthesis of the compounds described herein may be synthesized or can be obtained from commercial sources, such as, but not

Synthetic Examples

Example 1: Synthesis of (E)-2-methoxy-4-((8-methylnon-6-enamido)methyl)phenyl 2-((methylamino)methyl)-4-(2,5,8,11-tetraoxatetradecan-14-oyl)piperazine-1-carboxylate (Compound 1)

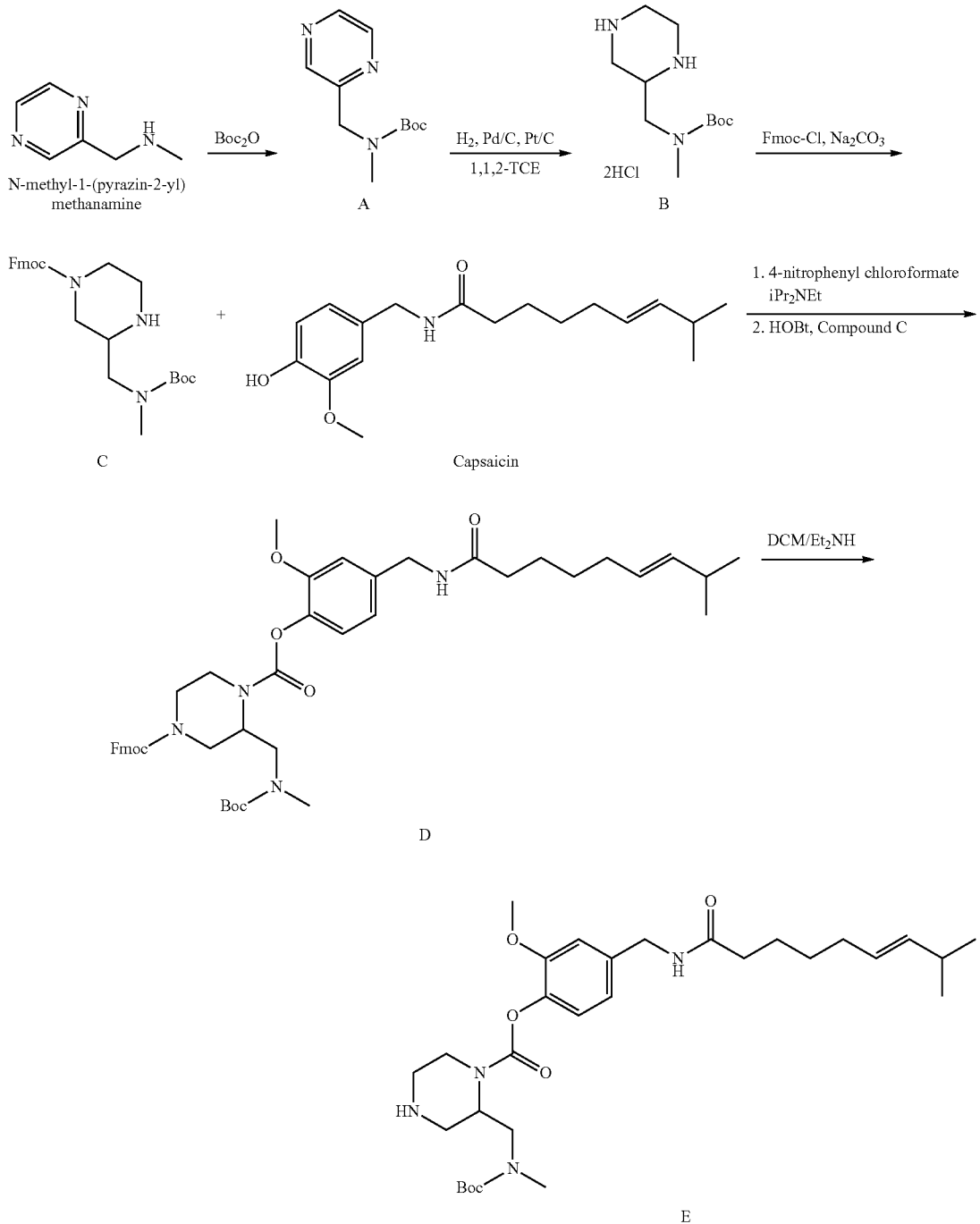

General Procedure 1 (Boc Protection)

An Ar purged, 500 mL 3-neck RBF equipped with a stir bar, condenser, and Ar inlet was charged with amine containing starting material and iPrOH. After cooling to 0° C., a solution of $Boc_2O$ in iPrOH was added over 1 hour. The reaction was allowed to warm to room temperature and stirred for 18 h. The reaction mixture was diluted with EtOAc (250 mL), and the organic phase was washed with a saturated solution of $Na_2CO_3$ (3×250 mL), brine (3×250 mL), dried over $MgSO_4$ (10 g), filtered with Whatman #4 filter paper, and concentrated in vacuo to afford the desired product.

Preparation of Compound A:

Following general procedure 1, methyl(pyrazin-2-ylmethyl)amine (15.0 g, 121.8 mmol) in iPrOH (125 mL) was reacted with a solution of $Boc_2O$ (31.9 g, 146.2 mmol) in iPrOH (25 mL) to afford compound A as a brown oil (29.2 g). $^1H$ NMR (500 MHz, $CDCl_3$) δ 8.69-8.35 (m, 3H), 4.56 (apparent d, J=29.3 Hz, 2H), 2.96 (apparent d, J=31.3 Hz, 3H), 1.45 (apparent d, J=35.9 Hz, 9H). LC-MS: m/z calcd for $C_{11}H_{18}N_3O_2$ $[M+H]^+$ 224.1, observed 224.1.

General Procedure 2 (Hydrogenation):

A 2-liter hydrogenation flask was charged with starting material, 1,1,2-trichloroethane, methanol and sparged with Ar for 1 h. Pd/C (10 wt %) and Pt/C (10 wt %,) were suspended in $H_2O$ and carefully added to the hydrogenation flask under a flow of Ar. The reaction flask was shaken on a Parr shaker hydrogenation apparatus with 70 psi $H_2$ for 72 h. The catalyst was filtered off with Celite and the filtrate was concentrated to yield crude desired product. The crude solid was suspended in iPrOH and re-concentrated. The resulting product was collected and then dried under high vacuum for 48 h to furnish the desired product.

Preparation of Compound B:

Following general procedure 2, compound A (27.2 g, 121.9 mmol) and 1,1,2-trichloroethane (35.8 g, 24.8 mL, 268.1 mmol) in methanol (800 mL) was shaken on a Parr shaker hydrogenation apparatus with Pd/C (10 wt %, 1.30 g, 1.22 mmol), Pt/C (10 wt %, 2.38 g, 1.22 mmol) in 30 mL $H_2O$ under 70 psi $H_2$ to produce compound B as a sticky light yellow solid (31.3 g, 97% over two steps). $^1H$ NMR (500 MHz, $CD_3OD$) δ 3.92-3.83 (m, 1H), 3.76-3.40 (m, 7H), 3.32-3.18 (m, 1H), 2.99 (s, 3H), 1.52 (s, 9H); LC-MS: m/z calcd for $C_{11}H_{23}N_3O_2$ $[M+H]^+$ 230.3, observed 230.2.

Preparation of Compound C:

An Ar purged, 5 L RBF equipped with a stir bar and 500 mL addition funnel was charged with compound B (23.4 g, 87.8 mmol), $Na_2CO_3$ (8.1 g, 82.4 mmol), and EtOH (2.0 L). The resulting solution was stirred for 1 h at rt. A solution of Fmoc-Chloride (25.0 g, 4.76 mmol) in EtOH (700 mL) and added drop wise over 3 hours. The resultant solution was stirred for 18 h at rt. The reaction was quenched with a saturated $Na_2CO_3$ solution (2.0 L) and brine (1.0 L). The aqueous layer was extracted with ethyl acetate (3×2.0 L), and the organic extract was washed with brine (3×1.0 L) dried over $MgSO_4$ and concentrated in vacuo. The crude yellow oil was purified via flash chromatography and then dried overnight under vacuum to yield compound C as a white solid (24.5 g, 62%). $^1H$ NMR (500 MHz, $CDCl_3$) δ 7.77 (d, J=7.6 Hz, 2H), 7.57 (d, J=7.5 Hz, 2H), 7.40 (t, J=7.5 Hz, 2H), 7.32 (t, J=7.5 Hz, 2H), 4.48-4.39 (m, 2H), 4.24 (t, J=6.9 Hz, 1H), 4.07-3.82 (m, 2H), 3.43-2.79 (m, 9H), 2.79-2.54 (m, 2H), 1.46 (s, 9H); LC-MS: m/z calcd for $C_{26}H_{33}N_3O_4$ $[M+H]^+$ 452.6, observed 452.2.

Preparation of Compound D:

An Ar purged 250 mL round bottomed flask equipped with a stir bar and Ar inlet was charged with capsaicin (2.82 g, 9.2 mmol), 4-nitrophenyl chloroformate (1.95 g, 9.7 mmol) and acetonitrile (75 mL). This mixture was cooled to 0° C., N,N-diisopropylethylamine (4.8 mL, 27.6 mmol) was added, and the mixture was stirred at 0° C. for 2 h. Compound C (5.0 g, 11.1 mmol) and hydroxybenzotriazole.$3H_2O$ (0.179 g, 0.92 mmol) were added to the reaction and the resultant solution was stirred at rt for 18 h. The reaction was then diluted with 100 mL of ethyl acetate and washed with a saturated $NH_4Cl$ solution (5×100 mL), brine (3×100 mL), dried with $MgSO_4$ and concentrated in vacuo. The crude bright yellow oil was purified via flash chromatography to yield compound D as a pure white solid (3.89 g, 54%). $^1H$ NMR (500 MHz, $CDCl_3$) δ 7.77 (d, J=7.5 Hz, 2H), 7.58 (d, J=7.5 Hz, 2H), 7.41 (t, J=7.4 Hz, 2H), 7.33 (t, J=7.5 Hz, 2H), 7.09-6.94 (m, 1H), 6.90-6.73 (m, 2H), 5.81-5.63 (m, 1H), 5.42-5.27 (m, 2H), 4.71-4.18 (m, 6H), 4.19-2.66 (m, 14H), 2.29-2.15 (m, 3H), 1.99 (q, J=7.0 Hz, 2H), 1.65 (q, J=7.5 Hz, 2H), 1.54-1.33 (m, 11H), 0.95 (d, J=6.8 Hz, 6H); LC-MS: m/z calcd for $C_{40}H_{51}N_4O_6$ $[M-Boc+H]^+$ 683.4, observed 683.3.

General Procedure 3 (FMOC Deprotection):

A RBF equipped with a stir bar was charged with FMOC protected intermediate and $CH_2Cl_2$. Diethylamine was added and the reaction was stirred at rt for 2 h. The reaction mixture was concentrated in vacuo and the crude light yellow oil was purified via flash chromatography to furnish the desired product.

Preparation of Compound E:

Following general procedure 3, reacting compound D (3.89 g, 4.97 mmol), in $CH_2Cl_2$ (65 mL) and diethylamine (65 mL) furnished compound E as a foamy white solid (1.78 g, 64%). $^1H$ NMR (500 MHz, $CDCl_3$) δ 7.08-6.97 (m, 1H), 6.87 (s, 1H), 6.82 (d, J=8.1 Hz, 1H), 5.73 (s, 1H), 5.43-5.25 (m, 2H), 4.45-4.17 (m, 3H), 4.08-3.65 (m, 5H), 3.49-3.12 (m, 2H), 3.06-2.76 (m, 7H), 2.27-2.15 (m, 3H), 1.99 (q, J=7.1 Hz, 2H), 1.82 (s, 1H), 1.65 (p, J=7.7 Hz, 2H), 1.52-1.35 (m, 11H), 0.95 (d, J=6.8, 1.9 Hz, 6H); LC-MS: m/z calcd for $C_{30}H_{49}N_4O_6$ $[M+H]^+$ 560.4, observed 561.3.

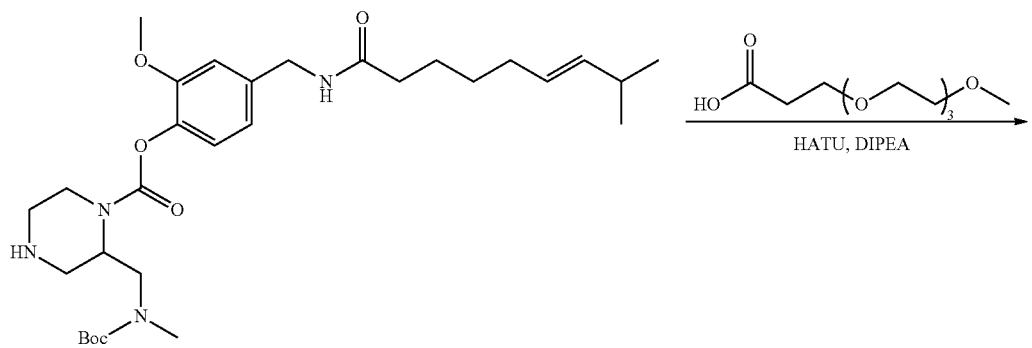

E

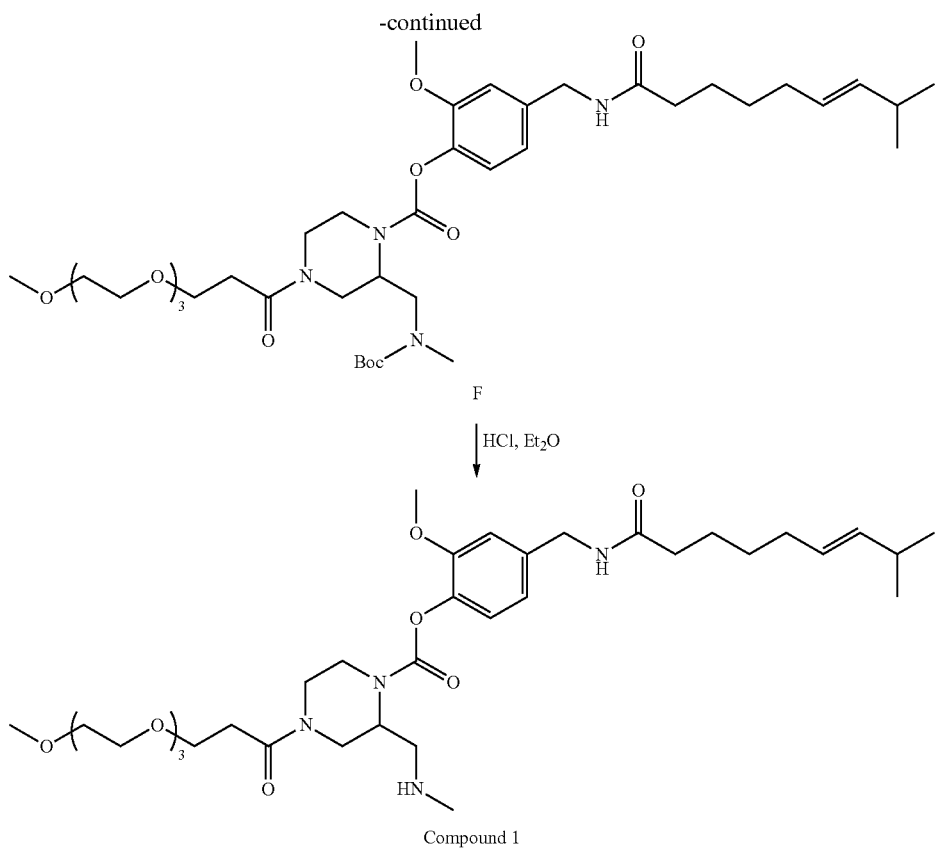

Compound 1

General Procedure 4 (Amide Bond Coupling with PEG-Carboxylic Acids):

An Ar purged flame dried 100 mL RBF equipped with a stir bar and Ar inlet was charged with PEG-Carboxylic acid, HATU (1-[Bis(dimethylamino)methylene]-1H-1,2,3-triazolo[4,5-b]pyridinium 3-oxid hexafluorophosphate), and THF (50 mL). The solution was cooled to 0° C. in an ice bath and Ar was bubbled through the solution for 10 minutes. Diisopropylethylamine (DIPEA) was then added and the reaction mixture was stirred at 0° C. After 2 hours, amine starting material was added and the reaction mixture was stirred for 18 h at rt. The reaction mixture was diluted with 75 mL EtOAc and washed with a saturated solution of $NaHCO_3$ (3×100 mL), a saturated solution of $NH_4Cl$ (3×100 mL), brine (3×100 mL) dried with $MgSO_4$ and concentrated in vacuo. The resulting crude material was purified via flash chromatography or preparative HPLC to furnish the desired product.

Preparation of Compound F:

Following general procedure 4, COOH-CM-PEG[3]-OMe (274 mg, 1.16 mmol), HATU (474 mg, 1.25 mmol), DIPEA (484 mg, 0.65 mL, 3.74 mmol) was reacted with compound E (500 mg, 0.89 mmol) to produce crude compound F. This was purified via flash chromatography to afford compound F as a clear viscous oil (493 mg, 71%). $^1H$ NMR (500 MHz, $CDCl_3$) δ 7.04 (s, 1H), 6.87 (s, 1H), 6.82 (d, J=8.0 Hz, 1H), 5.67 (s, 1H), 5.42-5.28 (m, 2H), 4.70-4.45 (m, 2H), 4.40 (d, J=5.5 Hz, 2H), 4.24-3.85 (m, 2H), 3.81 (s, 6H), 3.72-3.58 (m, 10H), 3.58-3.42 (m, 3H), 3.37 (s, 3H), 3.31-2.59 (m, 8H), 2.30-2.11 (m, 3H), 1.99 (q, J=6.9 Hz, 2H), 1.73-1.62 (m, 2H), 1.52-1.30 (m, 11H), 0.95 (d, J=6.7 Hz, 6H); LC-MS: m/z calcd for $C_{40}H_{67}N_4O_{11}$ $[M+H]^+$ 779.5, observed 779.4.

General Procedure 5 (Boc Deprotection):

An Ar purged flame dried RBF equipped with a stir bar and Ar inlet was charged with Boc protected prodrug and $Et_2O$ (20 mL). The solution was cooled to 0° C. in an ice bath and Ar was bubbled through the stirring solution. After purging the solution with Ar for 20 minutes, HCl in $Et_2O$ (2.0 M, 20 mL) was transferred via syringe to the stirring solution. Upon addition of ethereal HCl, the solution instantly turned an opaque white color which slowly cleared as the material deposited on the sides of the flask. The reaction mixture was concentrated in vacuo and placed under high vacuum for 12 h. The crude product was then dissolved in a minimum amount of $CH_2Cl_2$ and slowly added into centrifuge tubes containing hexanes/$Et_2O$ (50 mL, 1:1). The resultant highly vicious off white precipitate was centrifuged to a pellet and the supernatant was decanted. The product was dissolved and precipitated an additional three times to yield pure prodrug.

Preparation of Compound 1:

Following general procedure 5, compound F (442 mg, 0.57 mmol) was converted to Compound 1 (free flowing off white powder, 388 mg, 96%). $^1H$ NMR (500 MHz, $CD_3OD$) δ 7.10 (s, 1H), 7.05 (s, 1H), 6.90 (d, J=7.9 Hz, 1H), 5.43-5.32 (m, 2H), 4.86-4.02 (m, 6H), 3.91-3.75 (m, 5H), 3.73-3.48 (m, 13H), 3.48-3.34 (m, 5H), 3.29-2.89 (m, 3H), 2.87-2.75 (m, 3H), 2.61-2.45 (m, 1H), 2.29-2.17 (m, 3H), 2.01 (q, J=6.8 Hz, 2H), 1.65 (p, J=7.5 Hz, 2H), 1.39 (p, J=7.5 Hz, 2H), 0.97 (d, J=6.7 Hz, 6H); LC-MS: m/z calcd for $C_{35}H_{59}N_4O_9$ $[M+H]^+$ 679.4, observed 679.4.

Example 2: Synthesis of (E)-2-methoxy-4-((8-methylnon-6-enamido)methyl)phenyl 2-((methylamino)methyl)-4-(2,5,8,11,14,17,20-hetaoxatricosan-23-oyl)piperazine-1-carboxylate (Compound 2)

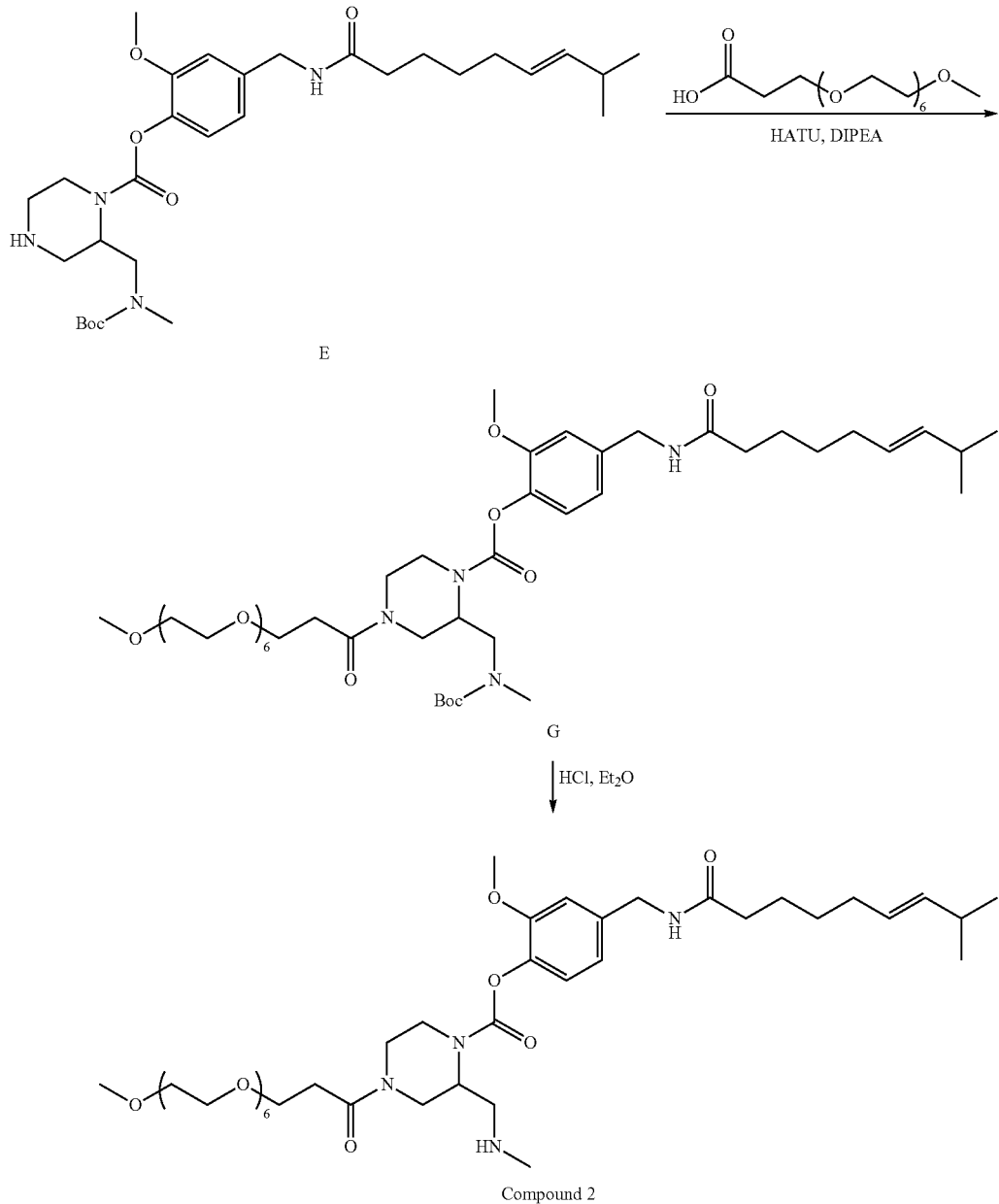

Preparation of Compound G:

Following general procedure 4, COOH-CM-PEG[6]-OMe (400 mg, 1.09 mmol), HATU (445 mg, 1.17 mmol), DIEA (466 mg, 0.63 mL, 3.60 mmol) was reacted with compound E (507 mg, 0.90 mmol) to produce crude compound G. This was purified flash chromatography to yield compound G as a clear viscous oil (716 mg, 87%). $^1$H NMR (500 MHz, CDCl$_3$) δ 7.09-6.95 (m, 1H), 6.87 (s, 1H), 6.82 (d, J=7.9 Hz, 1H), 5.70 (s, 1H), 5.41-5.27 (m, 2H), 4.70-4.43 (m, 2H), 4.40 (d, J=5.5 Hz, 2H), 4.19-3.86 (m, 2H), 3.86-3.71 (m, 6H), 3.65 (s, 22H), 3.57-3.44 (m, 3H), 3.37 (s, 3H), 3.31-2.62 (m, 8H), 2.26-2.18 (m, 3H), 1.99 (q, J=7.0 Hz, 2H), 1.65 (t, J=7.8 Hz, 2H), 1.52-1.32 (m, 11H), 0.94 (d, J=6.8 Hz, 6H); LC-MS: m/z calcd for C$_{46}$H$_{79}$N$_4$O$_{14}$ [M+H]$^+$ 911.6, observed 911.5.

Preparation of Compound 2:

Following general procedure 5, compound G (665 mg, 0.73 mmol) was converted to compound 2 (viscous light yellow oil, 553 mg, 89%). $^1$H NMR (500 MHz, CD$_3$OD) δ 7.15-7.01 (m, 2H), 6.94-6.86 (m, 1H), 5.44-5.32 (m, 2H), 4.84-4.44 (m, 2H), 4.38 (s, 2H), 4.33-4.08 (m, 2H), 3.90-3.36 (m, 35H), 3.31-2.94 (m, 3H), 2.91-2.77 (m, 3H), 2.45-2.30 (m, 1H), 2.30-2.15 (m, 3H), 2.02 (q, J=6.8 Hz, 2H), 1.65 (p, J=7.5 Hz, 2H), 1.40 (p, J=7.6 Hz, 2H), 0.97 (d, J=6.8 Hz, 6H); LC-MS: m/z calcd for C$_{41}$H$_{71}$N$_4$O$_{12}$ [M+H]$^+$ 811.5, observed 811.4.

Example 3: Synthesis of (E)-2-methoxy-4-((8-methylnon-6-enamido)methyl)phenyl 4-(2,5,8,11,14,17,20,23,26,29-decaoxadotriacontan-32-oyl)-2-((methylamino)methyl)piperazine-1-carboxylate (Compound 3)

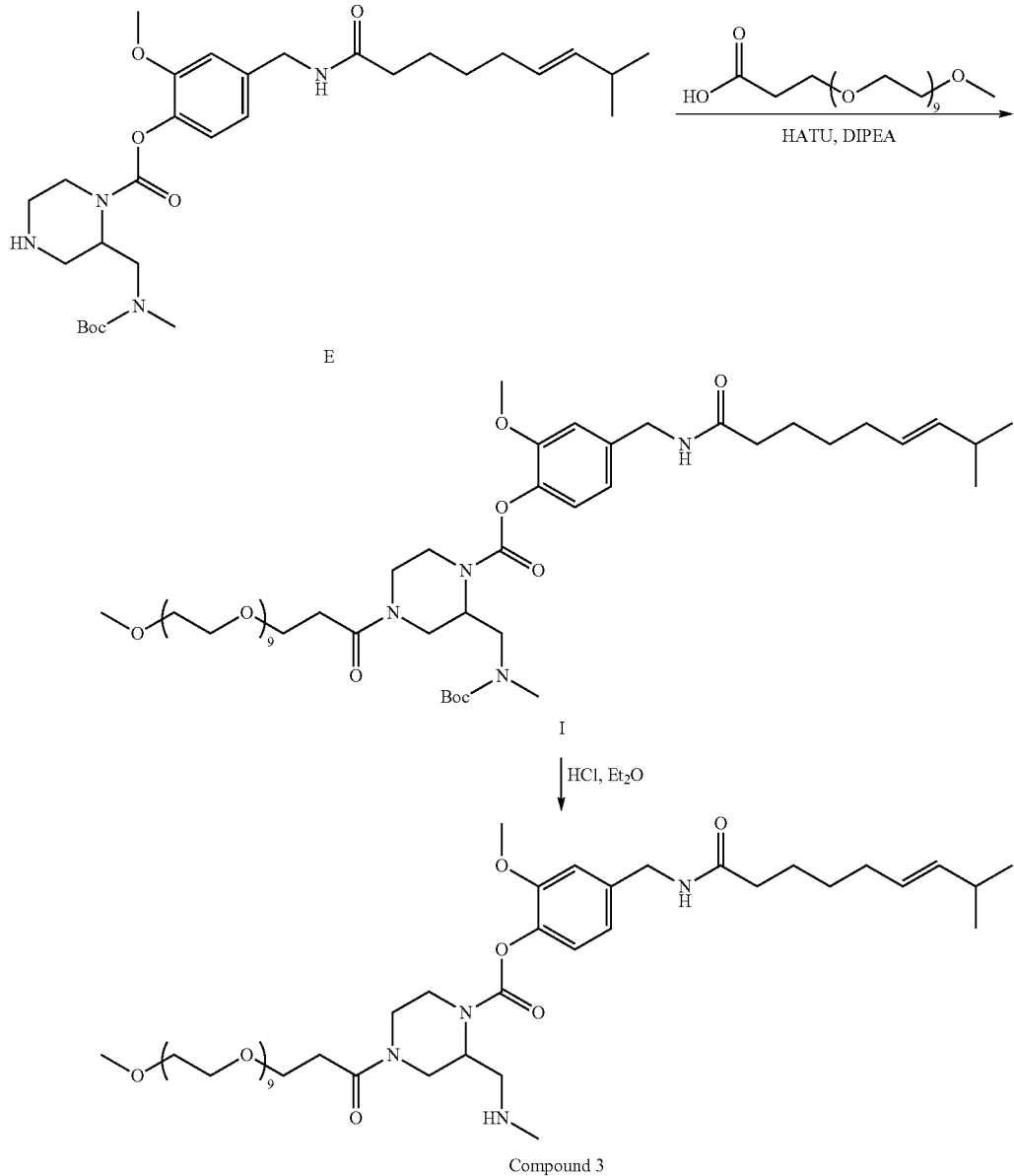

Preparation of Compound G:

Following general procedure 4, COOH-CM-PEG[9]-OMe (400 mg, 0.80 mmol), HATU (331 mg, 0.87 mmol), DIPEA (347 mg, 0.47 mL, 2.68 mmol) was reacted with compound E (373 mg, 0.67 mmol) to produce crude compound H. This was purified via HPLC to produce compound H as a clear viscous oil (519 mg, 74%). $^1$H NMR (500 MHz, CDCl$_3$) δ 7.08-6.91 (m, 1H), 6.86 (s, 1H), 6.81 (d, J=7.6 Hz, 1H), 5.83 (s, 1H), 5.40-5.24 (m, 2H), 4.71-4.42 (m, 2H), 4.37 (d, J=5.6 Hz, 2H), 4.19-3.84 (m, 2H), 3.79 (s, 6H), 3.63 (s, 34H), 3.55-3.40 (m, 3H), 3.35 (s, 3H), 3.32-2.53 (m, 8H), 2.25-2.15 (m, 3H), 1.97 (q, J=7.0 Hz, 2H), 1.63 (p, J=7.7 Hz, 2H), 1.48-1.33 (m, 11H), 0.93 (d, J=6.7 Hz, 6H); LC-MS: m/z calcd for C$_{52}$H$_{91}$N$_4$O$_{17}$ [M+H]$^+$ 1043.6, observed 1043.5.

Preparation of Compound 3:

An Ar purged flame dried 100 mL RBF equipped with a stir bar and Ar inlet was charged with compound H (463 mg, 0.44 mmol) and methanolic HCl (3M, 50 mL). The solution was heated to 40° C. in an oil bath and stirred for 2 h. The reaction mixture was concentrated in vacuo and placed under high vacuum for 12 h. The crude product was then dissolved in a minimum amount of CH$_2$Cl$_2$ and slowly added into centrifuge tubes containing hexanes/Et$_2$O (50 mL, 1:1). The resultant highly vicious off white precipitate was centrifuged to a pellet and the supernatant was decanted. The product was dissolved and precipitated an additional three times to yield Compound 3 as a viscous yellow oil (391 mg, 91%). $^1$H NMR (600 MHz, CD$_3$OD) δ 7.13-7.01 (m, 2H), 6.94-6.86 (m, 1H), 5.43-5.32 (m, 2H), 4.80-4.53 (m, 2H), 4.37 (s, 2H), 4.31-4.07 (m, 2H), 4.01-3.40 (m, 44H), 3.36 (s, 3H), 3.29-3.02 (m, 3H), 2.92-2.79 (m, 3H), 2.44-2.30 (m, 1H), 2.30-2.18 (m, 3H), 2.01 (q, J=6.9 Hz, 2H), 1.64 (p, J=7.6 Hz, 2H), 1.39 (p, J=7.5 Hz, 2H), 0.97 (d, J=6.7 Hz, 6H); LC-MS: m/z calcd for $C_{47}H_{83}N_4O_{15}$ $[M+H]^+$ 943.6, observed 943.4.
Example 4: Synthesis of (E)-2-methoxy-4-((8-methylnon-6-enamido)methyl)phenyl 4-(2,5,8,11,14,17,20,23,26,29,32,35,38-tridecaoxahentetracontan-41-oyl)-2-((methylamino)methyl)piperazine-1-carboxylate (Compound 4)
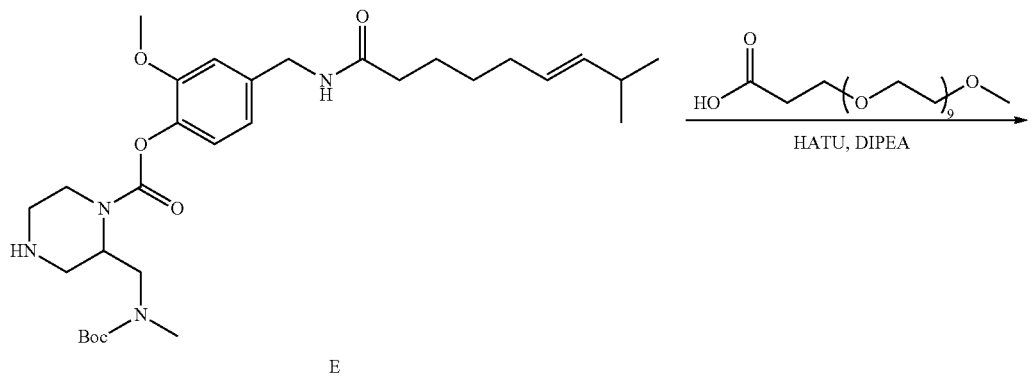
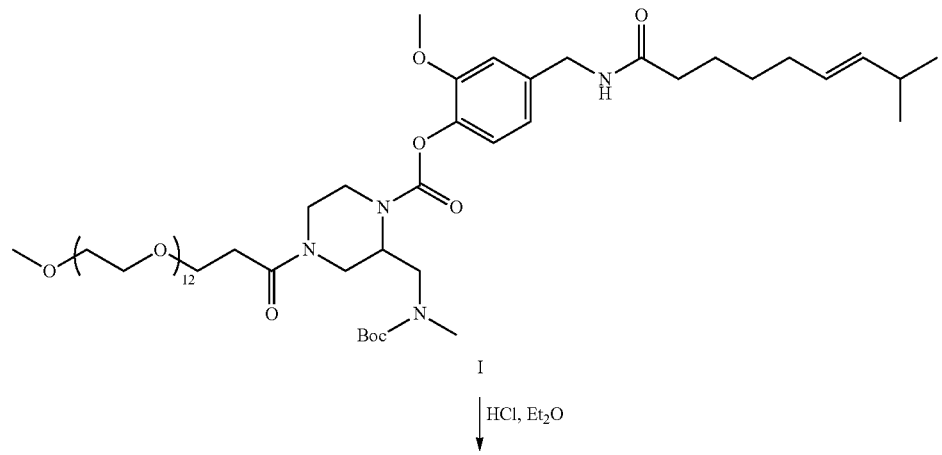
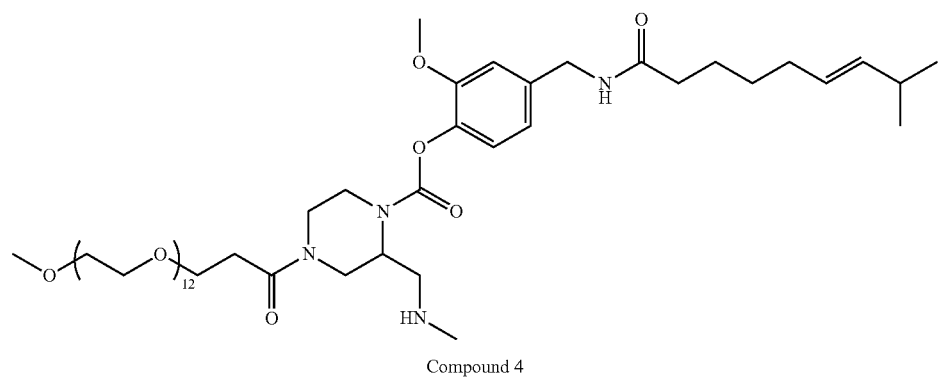
Compound 4

Preparation of Compound I:

Following general procedure 4, COOH-CM-PEG[12]-OMe (400 mg, 0.63 mmol), HATU (262 mg, 0.69 mmol), DIEA (274 mg, 0.37 mL, 2.12 mmol) was reacted with compound E (295 mg, 0.53 mmol) to produce crude compound I. This was purified via HPLC to furnish compound I as a clear viscous oil (338 mg, 54%). $^1$H NMR (500 MHz, CDCl$_3$) δ 7.09-6.95 (m, 1H), 6.87 (s, 1H), 6.82 (d, J=7.7 Hz, 1H), 6.10 (s, 1H), 5.41-5.25 (m, 2H), 4.76-4.46 (m, 2H), 4.41 (s, 2H), 4.27-3.90 (m, 2H), 3.81 (s, 6H), 3.64 (s, 46H), 3.58-3.47 (m, 3H), 3.37 (s, 3H), 3.36-2.60 (m, 8H), 2.27 (t, J=7.7 Hz, 2H), 2.25-2.16 (m, 1H), 1.98 (q, J=7.1 Hz, 2H), 1.64 (p, J=7.7 Hz, 2H), 1.52-1.33 (m, 11H), 0.94 (d, J=6.8 Hz, 6H); LC-MS: m/z calcd for C$_{53}$H$_{95}$N$_4$O$_{18}$ [M−Boc+2H]$^+$ 1075.7, observed 1075.6.

Preparation of Compound 4:

Following general procedure 5, compound I (303.5 mg, 0.26 mmol) was converted to compound 4 (viscous yellow oil, 214 mg, 75%). $^1$H NMR (600 MHz, CD$_3$OD) δ 7.14-7.02 (m, 2H), 6.94-6.87 (m, 1H), 5.43-5.33 (m, 2H), 4.76-4.58 (m, 2H), 4.38 (s, 2H), 4.33-4.16 (m, 2H), 4.16-3.40 (m, 56H), 3.37 (s, 3H), 3.29-3.08 (m, 3H), 2.91-2.80 (m, 3H), 2.45-2.32 (m, 1H), 2.29-2.20 (m, 3H), 2.01 (q, J=6.8 Hz, 2H), 1.65 (p, J=7.5 Hz, 2H), 1.40 (p, J=7.5 Hz, 2H), 0.97 (d, J=6.7 Hz, 6H); LC-MS: m/z calcd for C$_{53}$H$_{95}$N$_4$O$_{18}$ [M+H]$^+$ 1075.7, observed 1075.4.

Example 5: Synthesis of (E)-2-methoxy-4-((8-methylnon-6-enamido)methyl)phenyl 2-((methylamino)methyl)piperazine-1-carboxylate (Compound 5)

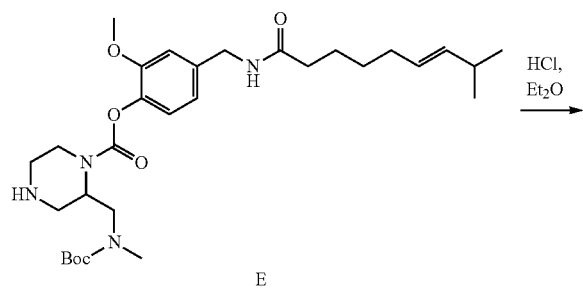

E

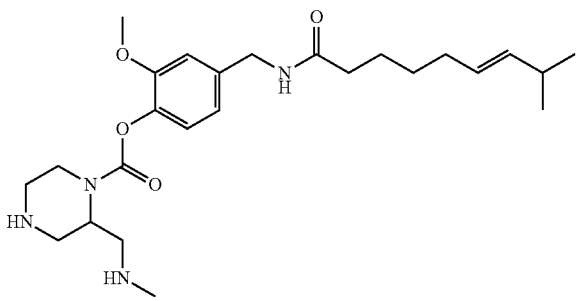

Compound 5

An Ar purged flame dried 50 mL RBF equipped with a stir bar and Ar inlet was charged with compound E (150 mg, 0.27 mmol) and methanolic HCl (3M, 20 mL). The solution was heated to 40° C. in an oil bath and stirred for 5 h. The reaction mixture was concentrated in vacuo and placed under high vacuum for 12 h. The crude product was then dissolved in a minimum amount of CH$_2$Cl$_2$ and slowly added into centrifuge tubes containing Et$_2$O (50 mL). The resultant off white precipitate was centrifuged to a pellet and the supernatant was decanted. The product was dissolved and precipitated an additional three times to yield compound 5 as an off white solid (103 mg, 77%). $^1$H NMR (500 MHz, CD$_3$OD) δ 7.15 (d, J=7.5 Hz, 1H), 7.07 (s, 1H), 6.92 (d, J=8.1 Hz, 1H), 5.44-5.33 (m, 2H), 5.13-4.96 (m, 1H), 4.63-4.21 (m, 4H), 3.89 (s, 4H), 3.66-3.42 (m, 4H), 3.38-3.35 (m, 1H), 3.31-3.20 (m, 1H), 2.85 (s, 3H), 2.30-2.19 (m, 3H), 2.02 (q, J=6.8 Hz, 2H), 1.65 (p, J=7.6 Hz, 2H), 1.40 (p, J=7.5 Hz, 2H), 0.98 (d, J=6.8 Hz, 6H); LC-MS: m/z calcd for C$_{25}$H$_{41}$N$_4$O$_4$ [M+H]$^+$ 461.3, observed 461.3.

Example 6: Synthesis of (E)-2-methoxy-4-((8-methylnon-6-enamido)methyl)phenyl 4-methyl-2-((methylamino)methyl)piperazine-1-carboxylate (Compound 6)

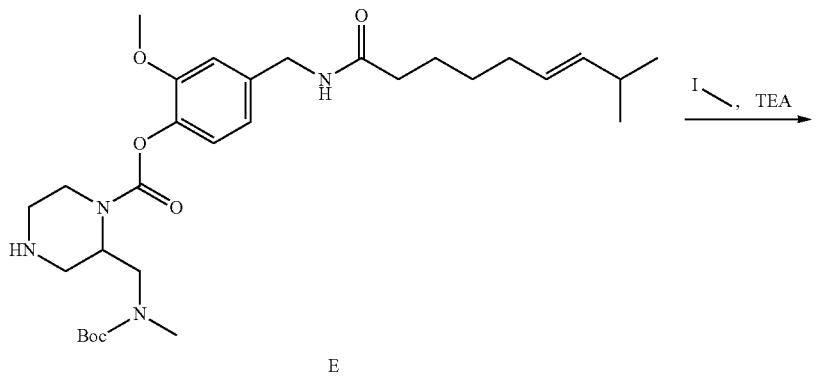

E

-continued

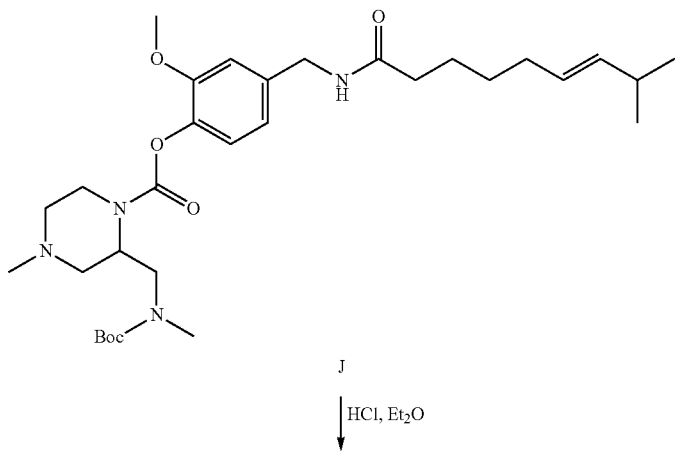

J

↓ HCl, Et₂O

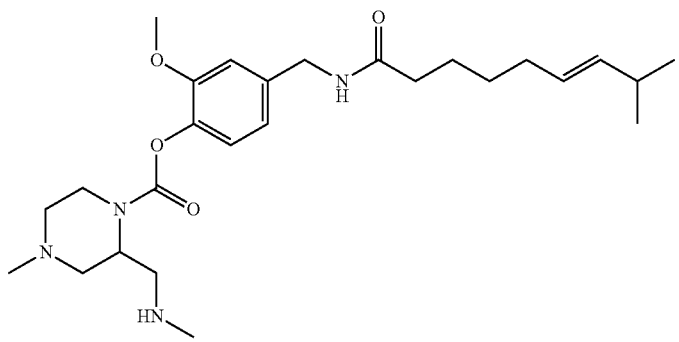

Compound 6

Preparation of Intermediate J:

An Ar purged 50 mL round bottomed flask equipped with a stir bar and Ar inlet was charged with compound E (200 mg, 0.36 mmol), triethylamine (44 mg, 0.06 mL, 0.43 mmol), CH₂Cl₂ (20 mL), and cooled to 0° C. in an ice bath. After stirring for 10 min, iodomethane (511 mg, 0.22 mL, 3.60 mmol) was then added and the resultant solution was stirred at rt for 18 hours. The reaction mixture was concentrated in vacuo and the crude material was purified via flash chromatography to furnish intermediate J as an off white solid. LC-MS: m/z calcd for $C_{31}H_{51}N_4O_6$ [M+H]⁺ 575.4, observed 575.4.

Preparation of Compound 6:

An Ar purged flame dried 50 mL RBF equipped with a stir bar and Ar inlet was charged with intermediate J (206.6 mg, 0.36 mmol) and methanolic HCL (3M, 20 mL). The solution was heated to 40° C. in an oil bath and stirred for 18 h. The reaction mixture was concentrated in vacuo and placed under high vacuum for 12 h. The crude product was then dissolved in a minimum amount of EtOH and slowly added into centrifuge tubes containing Et₂O/hexanes (50 mL, 1:1). The resultant off white precipitate was centrifuged to a pellet and the supernatant was decanted. The product was dissolved and precipitated an additional three times to yield compound 6 as an off white solid (89.7 mg, 52% over 2 steps). ¹H NMR (500 MHz, CD₃OD) δ 7.14 (d, J=8.1 Hz, 1H), 7.07 (s, 1H), 6.92 (d, J=8.0 Hz, 1H), 5.44-5.33 (m, 2H), 5.18-4.93 (m, 1H), 4.62-4.40 (m, 2H), 4.38 (s, 2H), 4.00-3.81 (m, 4H), 3.66 (dd, J=50.3, 13.1 Hz, 3H), 3.52-3.44 (m, 1H), 3.30-3.14 (m, 3H), 2.99 (s, 3H), 2.86 (d, J=24.7 Hz, 3H), 2.31-2.18 (m, 3H), 2.02 (q, J=6.8 Hz, 2H), 1.65 (p, J=7.7 Hz, 2H), 1.40 (p, J=7.5 Hz, 2H), 0.98 (dd, J=6.8, 1.8 Hz, 6H); LC-MS: m/z calcd for $C_{26}H_{43}N_4O_4$ [M+H]⁺ 475.3, observed 475.3.

Example 7: Synthesis of (E)-2-methoxy-4-((8-methylnon-6-enamido)methyl)phenyl 4-acetyl-2-((methylamino)methyl)piperazine-1-carboxylate (compound 7)

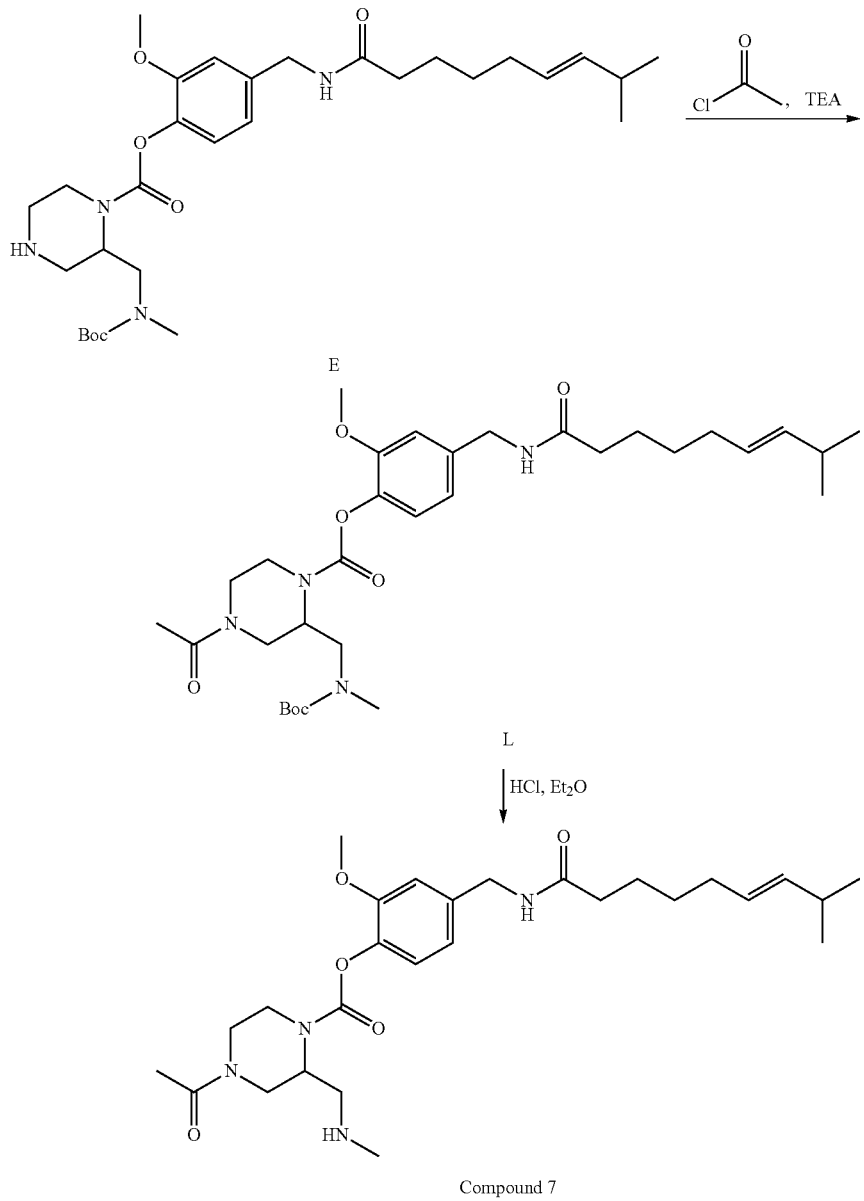

Preparation of Compound L:

An Ar purged 100 mL round bottomed flask equipped with a stir bar and Ar inlet was charged with compound E (500 mg, 0.89 mmol), $CH_2Cl_2$ (40 mL) and cooled to 0° C. in an ice bath. Triethylamine (99.3 mg, 0.14 mL, 0.98 mmol) was added and the resultant solution was stirred for 10 min. Acetyl chloride (84.0 mg, 0.076 mL, 1.07 mmol) was then added and stirred at 0° C. for 1 h. The reaction mixture was concentrated in vacuo and the crude off white solid was purified via flash chromatography to furnish compound L as a white solid (464 mg, 87%). $^1$H NMR (500 MHz, $CDCl_3$) δ 7.08-6.94 (m, 1H), 6.87 (s, 1H), 6.81 (d, J=7.7 Hz, 1H), 5.82 (s, 1H), 5.41-5.26 (m, 2H), 4.72-4.42 (m, 2H), 4.38 (d, J=5.5 Hz, 2H), 4.21-4.02 (m, 1H), 3.88-3.57 (m, 5H), 3.56-2.73 (m, 7H), 2.25-2.09 (m, 6H), 1.98 (q, J=7.0 Hz, 2H), 1.64 (p, J=7.7 Hz, 2H), 1.50-1.34 (m, 11H), 0.94 (d, J=6.8, 1.6 Hz, 6H); LC-MS: m/z calcd for $C_{32}H_{51}N_4O_7$ $[M+H]^+$ 603.4, observed 603.4.

Preparation of Compound 7:

Following general procedure E, compound L (414 mg, 0.69 mmol) was converted to compound 7 (free flowing white powder, 362 mg, 98%). $^1$H NMR (500 MHz, $CD_3OD$) δ 7.10 (d, J=8.1 Hz, 1H), 7.04 (s, 1H), 6.89 (d, J=8.0 Hz, 1H), 5.42-5.31 (m, 2H), 4.85-4.55 (m, 1H), 4.53-4.40 (m, 1H), 4.37 (s, 2H), 4.32-4.11 (m, 1H), 3.96 (s, 1H), 3.91-3.77 (m, 3H), 3.69-3.34 (m, 3H), 3.15 (td, J=13.2, 12.7, 4.3 Hz, 2H), 2.86-2.69 (m, 3H), 2.31-2.11 (m, 6H), 2.00 (q, J=6.8 Hz, 2H), 1.64 (p, J=7.7 Hz, 2H), 1.38 (p, J=7.5 Hz, 2H), 0.96 (d, J=6.8 Hz, 6H); LC-MS: m/z calcd for $C_{27}H_{43}N_4O_5$ $[M+H]^+$ 503.3, observed 503.3.

Example 8: Synthesis of (E)-4-ethyl 1-(2-methoxy-4-((8-methylnon-6-enamido)methyl)phenyl) 2-((methylamino)methyl)piperazine-1,4-dicarboxylate (Compound 8)

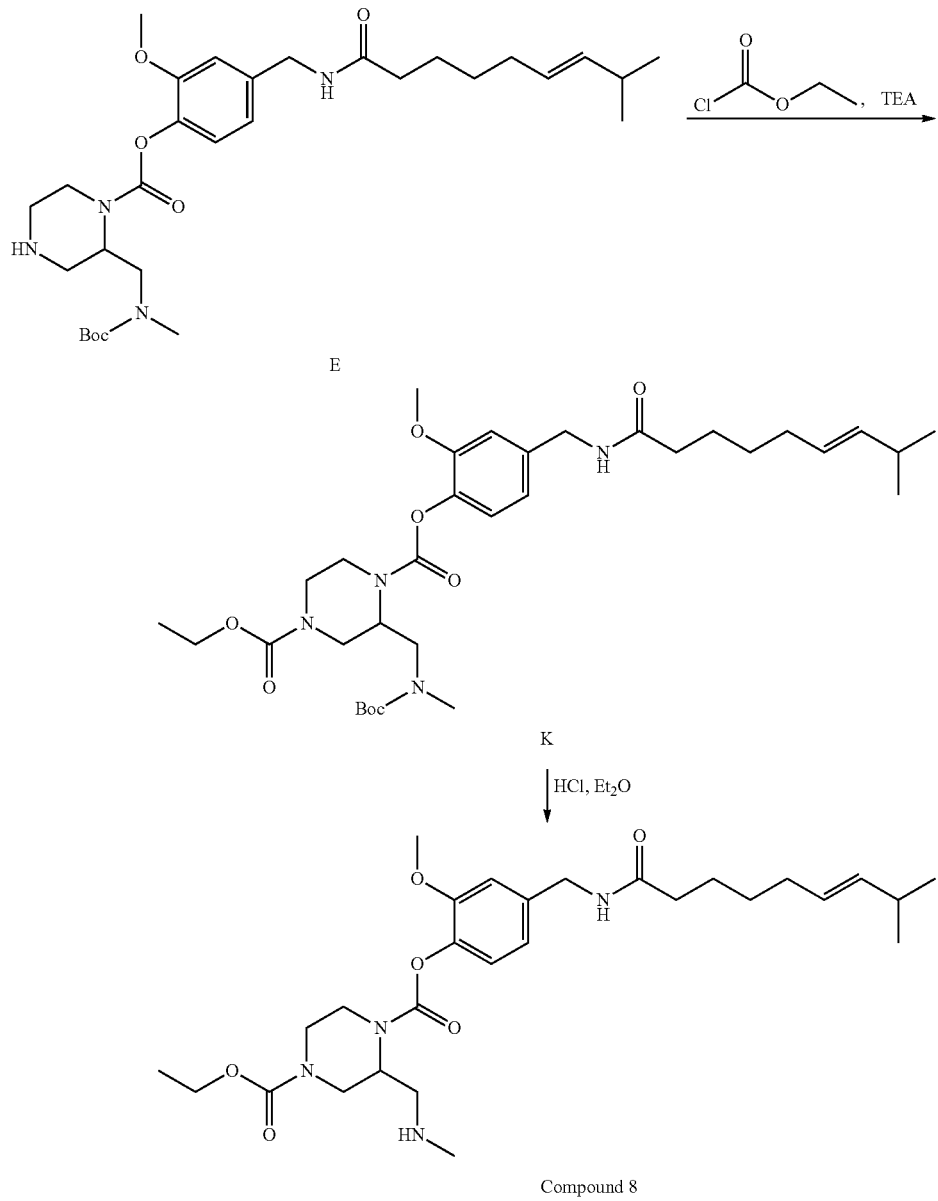

Preparation of Intermediate K:

An Ar purged 25 mL round bottomed flask equipped with a stir bar and Ar inlet was charged with compound E (150 mg, 0.27 mmol), CH$_2$Cl$_2$ (15 mL) and cooled to 0° C. in an ice bath. Triethylamine (32 mg, 45 μL, 0.32 mmol) was added and the resultant solution was stirred for 10 min. Ethyl chloroformate (32 mg, 28 μL, 0.30 mmol) was then added and stirred at 0° C. for 1 h. The reaction mixture was concentrated in vacuo and compound K, as a fluffy off white solid, was carried on without further purification.

Preparation of Compound 8:

An Ar purged flame dried 25 mL RBF equipped with a stir bar and Ar inlet was charged with compound K (170.9 mg, 0.27 mmol) and methanolic HCl (3M, 10 mL). The solution was heated to 40° C. in an oil bath and stirred for 1 h. The reaction mixture was concentrated in vacuo and placed under high vacuum for 12 h. The crude product was then dissolved in a minimum amount of EtOH and slowly added into centrifuge tubes containing Et$_2$O/hexanes (50 mL, 1:1). The resultant white precipitate was centrifuged to a pellet and the supernatant was decanted. The product was dissolved and precipitated an additional three times to yield compound 8 as a white solid (155 mg, <99% over 2 steps). $^1$H NMR (500 MHz, CD$_3$OD) δ 7.11 (d, J=8.0 Hz, 1H), 7.06 (s, 1H), 6.96-6.87 (m, 1H), 5.46-5.33 (m, 2H), 4.65 (s, 1H), 4.38 (s, 2H), 4.32-4.02 (m, 5H), 3.92-3.83 (m, 3H), 3.57 (s, 2H), 3.29-3.17 (m, 3H), 2.91-2.71 (m, 3H), 2.31-2.19 (m, 3H), 2.02 (q, J=6.9 Hz, 2H), 1.66 (p, J=7.6 Hz, 2H), 1.45-1.38 (m, 2H), 1.33 (dt, J=10.9, 7.1 Hz, 3H), 0.98 (d, J=6.6 Hz, 6H); LC-MS: m/z calcd for C$_{28}$H$_{45}$N$_4$O$_6$ [M+H]$^+$ 533.3, observed 533.3.

In Vitro Assays

Example 9: Solubility Assay

In order to determine the aqueous solubility of the compounds described herein, the HCl salts of the following compounds are incubated at either 50 or 100 mg/mL in DI water followed by shaking for 24 hours. The solutions are then centrifuged and visually inspected for insoluble material.

Example 10: In Vitro (pH Stability) Assay

The release of parent drug (e.g. capsaicin) from the compounds described herein is demonstrated by the stability testing of several compounds. The compounds described herein are examples of pH activated prodrugs whereby upon exposure to a specific pH, the half-life of the intramolecular cyclization-release reaction is determined. The intramolecular cyclization-release reaction results in the concomitant formation of a cyclic urea with the release of the parent drug.

Compounds were incubated in the buffer/biological media indicated. The reactions were conducted at either room temperature or 37° C. In some embodiments, additional common ingredients/formulations which may be used in buffers for the testing of the cyclization-release of the compounds described herein include but are not limited to: N-(2-Acetamido)-2-aminoethanesulfonic acid, N-(2-Acetamido)iminodiacetic acid, 2-Amino-2-methyl-1,3-propanediol, salts of bicarbonate, N,N-Bis(2-hydroxyethyl)glycine, 2-Bis(2-hydroxyethyl)amino-2-(hydroxymethyl)-1,3-propanediol, 3-(Cyclohexylamino)-1-propanesulfonic acid, 2-(Cyclohexylamino)ethanesulfonic acid, salts of carbonate, salts of citrate, 4-(2-Hydroxyethyl)-1-piperazinepropanesulfonic acid, salts of glycine, salts of Glycyl-glycine, 4-(2-Hydroxyethyl)piperazine-1-ethanesulfonic acid, 4-Morpholineethanesulfonic acid, 4-Morpholinepropanesulfonic acid, 1,4-Piperazinediethanesulfonic acid, salts of phosphate, salts of tartrate, 2-[(2-Hydroxy-1,1-bis(hydroxymethyl)ethyl)amino]ethanesulfonic acid, Tris(2-hydroxyethyl)amine, and salts of EDTA.

Samples were collected at specific time points, quenched with a 1.0% TFA in acetonitrile solution to stop the cyclization-release reaction and analyzed by HPLC for formation of released capsaicin, cyclic urea by-product, and consumption of starting compound in plasma and cerebrospinal fluid (CSF). As shown in Table 1, both acylated prodrugs (compound 1, compound 2, compound 3, compound 4, compound 7, and compound 8) and non-acylated prodrugs (compound 5 and compound 6) demonstrated rapid intramolecular cyclization-release under simulated physiological conditions (i.e. all prodrugs demonstrated half-life of conversion to capsaicin <5 min at pH 7.4 & 37° C.). However, as shown in Table 1, acylated piperazine prodrugs (compound 1, compound 2, compound 3, compound 7, and compound 8) demonstrated a significant and unexpected increase in stability at pH 4.5 at room temperature (RT) in comparison to the non-acylated prodrug (compound 6). Thus, since the acylated piperazine prodrugs described herein demonstrated increased solution state stability at pH 4.5, these prodrugs should provide a reasonable time window for the holding/manipulation of dose formulations of the prodrugs prior to administration (e.g. 0-4 hours) without substantial conversion to the active drug (i.e. capsaicin).

TABLE 1

Cyclization release data for Compounds 1-8

| Compound | Intramolecular Cyclization-Release Half-life ($T_{1/2}$) at pH 4.5 & RT[a] | Intramolecular Cyclization-Release Half-life ($T_{1/2}$) at pH 7.4 & 37° C[b] |
| --- | --- | --- |
| 01 | 43.3 hours | ~0.8 min |
| 02 | 40.8 hours | ~0.7 min |
| 03 | 51.0 hours | ~0.8 min |
| 04 | NT | ~0.6 min |
| 05 | NT | ~0.4 min |
| 06 | 1.3 hours | ~0.8 min |
| 07 | 115.5 hours | ~0.9 min |
| 08 | 46.2 hours | ~1.3 min |

Figure 2:
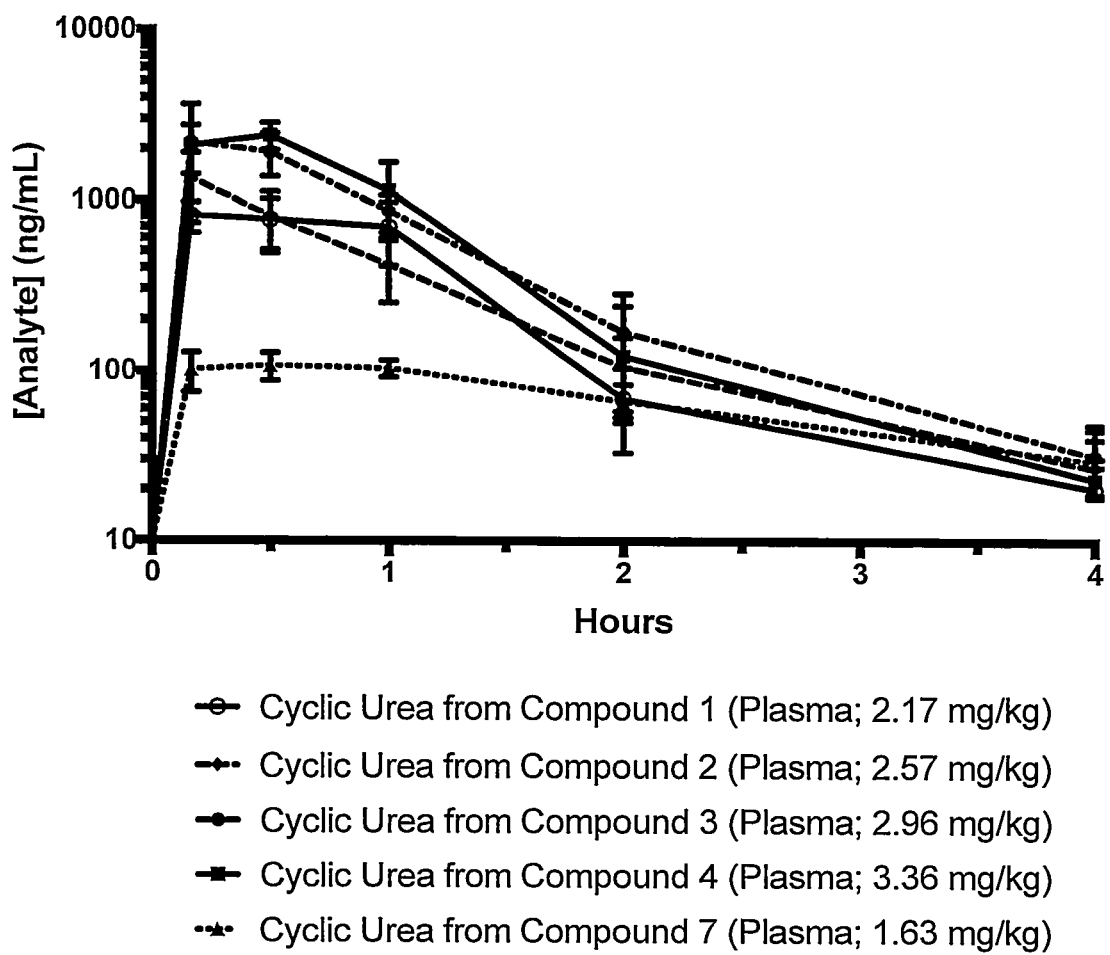
FIG. 2 shows the plasma concentration (ng/mL) time course of the resultant cyclic ureas of compounds 1, 2, 3, 4, and 7 in rats.
Figure 3:
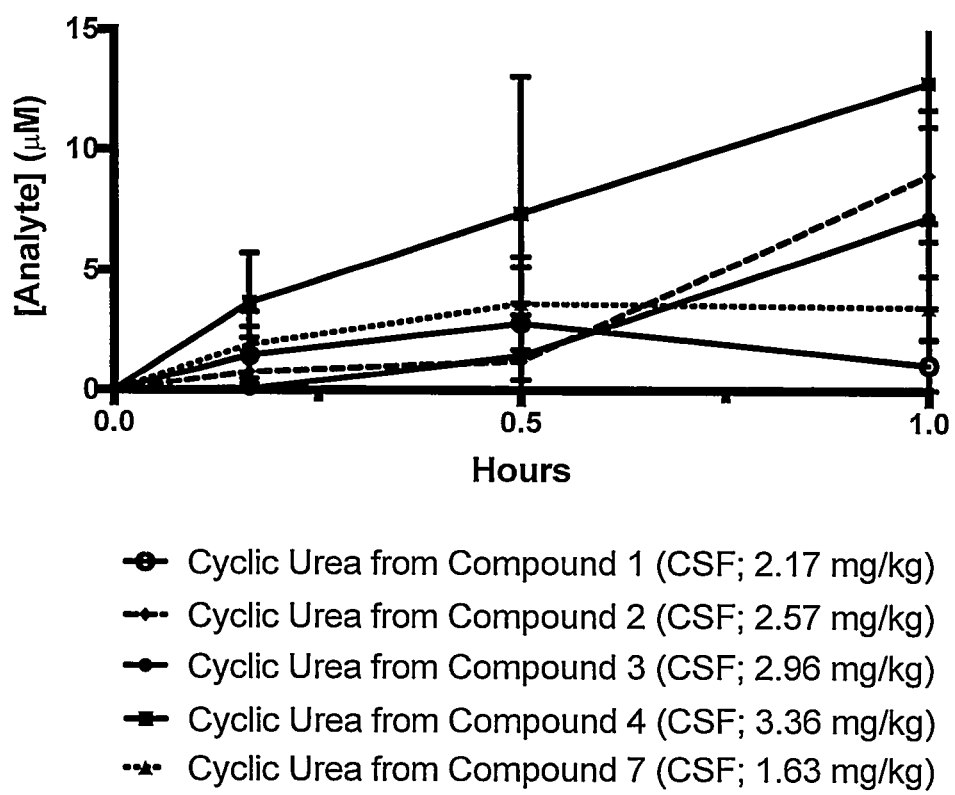
FIG. 3 shows the cerebrospinal fluid (CSF) concentration (µM) time course of the resultant cyclic ureas of compounds 1, 2, 3, 4, and 7 in rats.

[a]Conditions: pH = 4.5 (0.1M aqueous sodium acetate buffer), RT
[b]Conditions: pH = 7.4 (0.2M aqueous tris buffer), 37° C.
NT = not tested Pharmacokinetic Assay Example 11: Plasma & CSF Time Course of Test Compounds Following Epidural Administration to Rat Epidural dosing: Compound 1 through compound 4 and compound 7 were dissolved in sterile water for injection, pH adjusted to 4.5 and then dosed via epidural injection into male Sprague-Dawley rats. Compounds 1 through compound 4 and compound 7 were dosed as mg/kg body weight and are molar corrected to be equimolar. At specific time points, blood samples (0.25 mL) were collected from a jugular vein cannula into tubes containing $K_2$EDTA as anticoagulant and 10 µL of 2.5 M citrate buffer (pH 3.0) as a stabilizer to prevent conversion of the prodrug ex vivo and processed for plasma. The plasma samples were collected from each rat pre-dose and at 10 and 30 minutes, and 1 hour, 2 hour and 4 hours post-dose. At specific time points, CSF samples (0.05 mL) were collected via CM tap into tubes containing $K_2$EDTA as anticoagulant and 10 µL of 2.5 M citrate buffer (pH 3.0) as a stabilizer to prevent conversion of the prodrug ex vivo. The CSF samples were collected from each rat pre-dose and at 10 and 30 minutes, and 1 hour post-dose. Plasma and CSF concentration of capsaicin and/or resulting cyclic ureas from test compounds were determined and are shown in FIG. 1, FIG. 2, and FIG. 3. As shown in FIG. 3, the resultant cyclic ureas showed differential CSF penetration over the time-course observed. The cyclic urea of compound 2 showed the least amount of CSF exposure, on a molar basis, of the resultant cyclic ureas when their corresponding prodrugs were dosed epidurally in rats at equimolar doses.

The examples and embodiments described herein are for illustrative purposes only and in some embodiments, various modifications or changes are to be included within the purview of the disclosure and scope of the appended claims.

-continued
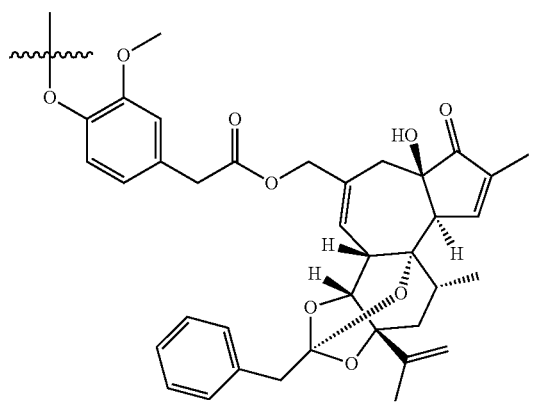
17. The method of claim 16, wherein Y is
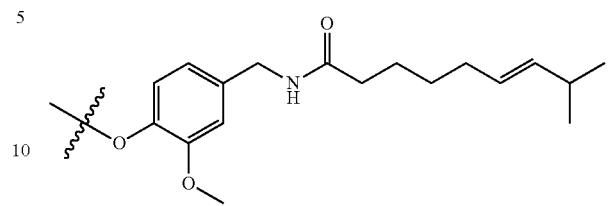
18. The method of claim 1, wherein the compound of Formula (I), or a pharmaceutically acceptable salt, pharmaceutically acceptable solvate, or hydrate thereof, is:
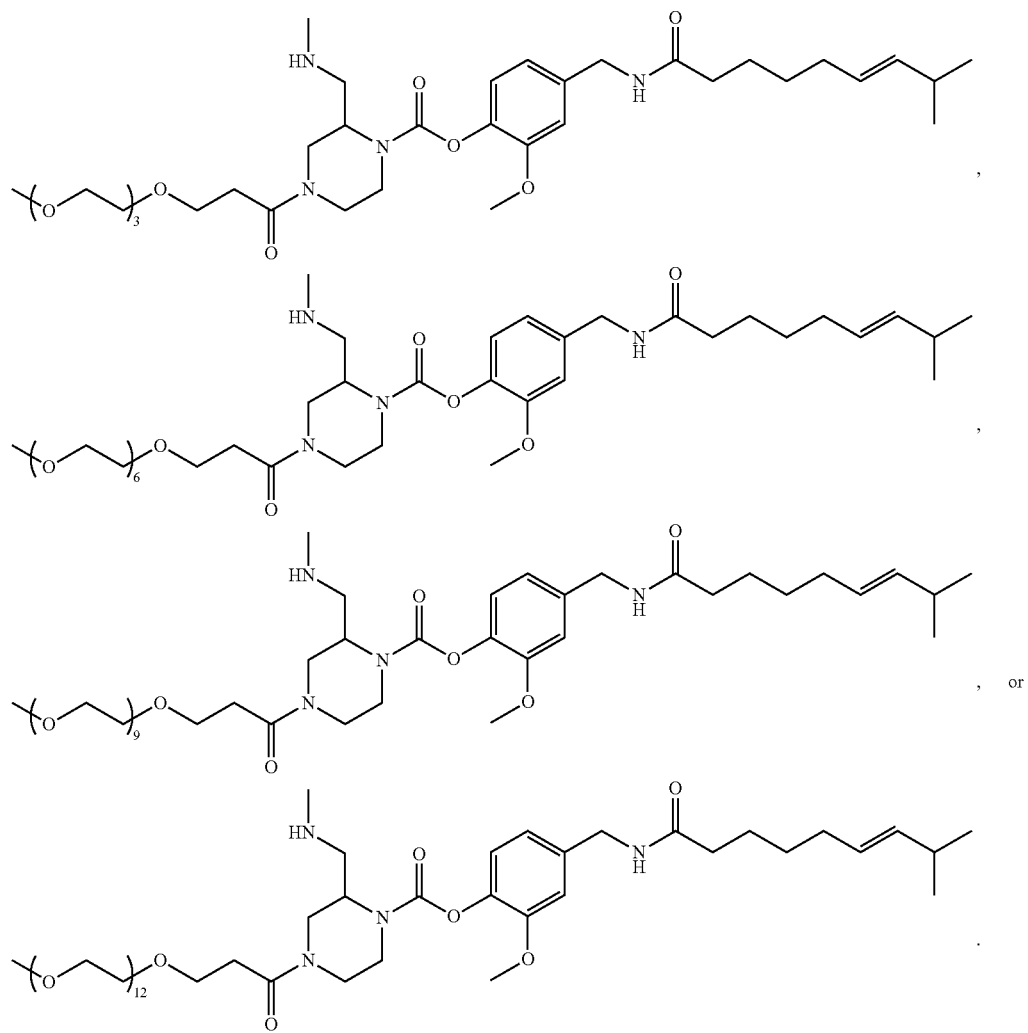

What is claimed is:

1. A method of treating pain in a subject, comprising administering to the subject a therapeutically effective amount of a compound of Formula (I), or a pharmaceutically acceptable salt, pharmaceutically acceptable solvate, or hydrate thereof:

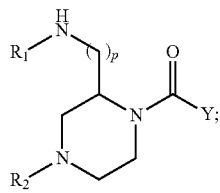

Formula (I)

wherein:

Y is a phenolic TRPV1 agonist, wherein the hydrogen atom of the phenolic hydroxyl group is replaced by a covalent bond to

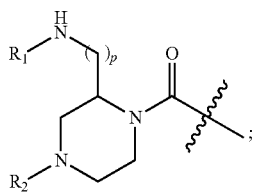

$R_1$ is hydrogen or $C_1$-$C_6$alkyl;
$R_2$ is —(CH$_2$CH$_2$O)$_n$R$_3$, —C(O)(CH$_2$)$_m$O(CH$_2$CH$_2$O)$_n$R$_3$, —C(O)O(CH$_2$CH$_2$O)$_n$R$_3$, —C(O)N(R$_4$)(CH$_2$CH$_2$O)$_n$R$_3$, —C(O)R$_5$, —C(O)OR$_5$, or —C(O)N(R$_4$)(R$_5$);
$R_3$ is hydrogen or $C_1$-$C_6$alkyl;
$R_4$ is hydrogen or $C_1$-$C_6$alkyl;
$R_5$ is $C_1$-$C_{50}$alkyl;
m is 1-10;
n is 1-50; and
p is 1-9.

2. The method of claim 1, wherein $R_2$ is —(CH$_2$CH$_2$O)$_n$R$_3$, —C(O)(CH$_2$)$_m$O(CH$_2$CH$_2$O)$_n$R$_3$, —C(O)O(CH$_2$CH$_2$O)$_n$R$_3$, or —C(O)N(R$_4$)(CH$_2$CH$_2$C)$_n$R$_3$.

3. The method of claim 2, wherein $R_2$ is —C(O)(CH$_2$)$_m$O(CH$_2$CH$_2$O)$_n$R$_3$.

4. The method of claim 3, wherein m is 1-5.

5. The method of claim 4, wherein m is 2.

6. The method of claim 3, wherein $R_3$ is hydrogen.

7. The method of claim 3, wherein $R_3$ is $C_1$-$C_6$alkyl.

8. The method of claim 7, wherein $R_3$ is —CH$_3$.

9. The method of claim 3, wherein n is 1-30.

10. The method of claim 9, wherein n is 2-20.

11. The method of claim 10, wherein n is 2-12.

12. The method of claim 1, wherein $R_1$ is $C_1$-$C_6$alkyl.

13. The method of claim 12, wherein $R_1$ is —CH$_3$.

14. The method of claim 1, wherein $R_1$ is hydrogen.

15. The method of claim 1, wherein p is 1.

16. The method of claim 1, wherein Y is

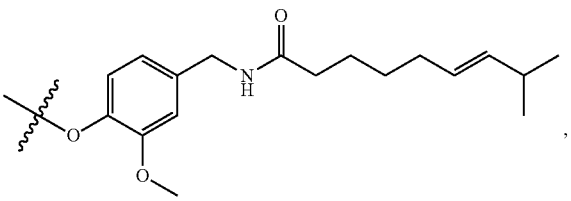 [SMILES: *Oc1ccc(CNC(=O)CCCC/C=C/C(C)C)cc1OC]

,

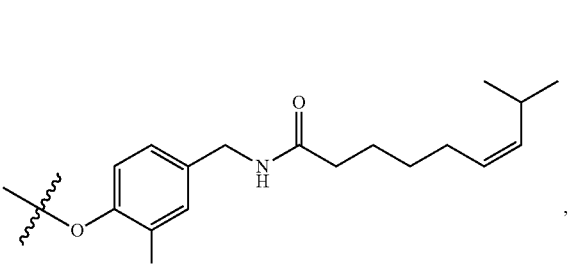

,

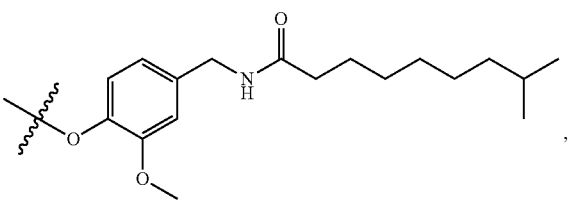

,

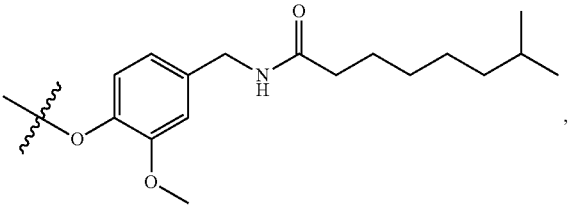

,

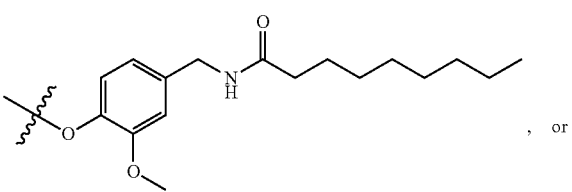

, or